US010960084B2

(12) United States Patent
Oka et al.

(10) Patent No.: US 10,960,084 B2
(45) Date of Patent: Mar. 30, 2021

(54) MODULATION OF FLUID INTAKE

(71) Applicant: California Institute of Technology, Pasadena, CA (US)

(72) Inventors: Yuki Oka, Pasadena, CA (US); Vineet Augustine, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/245,801

(22) Filed: Jan. 11, 2019

(65) Prior Publication Data

US 2019/0216948 A1 Jul. 18, 2019

Related U.S. Application Data

(60) Provisional application No. 62/616,963, filed on Jan. 12, 2018.

(51) Int. Cl.
| | |
|---|---|
| *A61K 48/00* | (2006.01) |
| *A61P 43/00* | (2006.01) |
| *A61K 31/5513* | (2006.01) |
| *C12N 15/86* | (2006.01) |
| *A61K 38/17* | (2006.01) |
| *A61P 13/12* | (2006.01) |
| *C12N 7/00* | (2006.01) |

(52) U.S. Cl.
CPC ........ *A61K 48/005* (2013.01); *A61K 31/5513* (2013.01); *A61K 38/1787* (2013.01); *A61P 13/12* (2018.01); *A61P 43/00* (2018.01); *C12N 7/00* (2013.01); *C12N 15/86* (2013.01); *C12N 2750/14143* (2013.01); *C12Y 114/13039* (2013.01)

(58) Field of Classification Search
CPC ... A61K 48/005; A61K 31/5513; C12N 15/86
See application file for complete search history.

(56) References Cited

PUBLICATIONS

Allen et al. Supplementary Materials for Thirst-associated preoptic neurons encode an aversive motidational drive. Science 357, 1149 (2017).*
Armstrong et al. Thirst and Drinking Paradigms: Evolution from Single Factor Effects to Brainwide Dynamic Networks. Nutrients 2019, 11(12), 2864; https://doi.org/10.3390/nu11122864.*
Rood, J. "Thirst Neurons Found," The Scientist, Daily News, Jan. 26, 2015, retrieved from https://www.the-scientist.com/daily-news/thirst-neurons-found-36043 on May 21, 2020.*
Ramsay et al., "Thirst: Physiological and Psychological Aspects", Chapters 5, 6, 9-12, and 19 (Springer-Verlog, 1991).
Bourque, C. W., "Central mechanisms of osmosensation and systemic osmoregulation", Nature reviews, Neuroscience, vol. 9, pp. 519-531, doi:10.1038/nrn2400 (2008).
McKinley et al., "The physiological regulation of thirst and fluid intake", News Physiol Sci, vol. 19, pp. 1-6 (2004).
Sternson et al., "Three Pillars for the Neural Control of Appetite", Annu Rev Physiol, vol. 79, pp. 401-423, doi:10.1146/annurev-physiol-021115-104948 (2017).
Seckl et al., "Oral hypertonic saline causes transient fall of vasopressin in humans", Am J Physiol, vol. 251, pp. R214-R217 (1986).
Thrasher et al., "Satiety and inhibition of vasopressin secretion after drinking in dehydrated dogs", Am J Physiol, vol. 240, pp. E394-E401 (1981).
Zimmerman et al., "Neural circuits underlying thirst and fluid homeostasis", Nature reviews, Neuroscience, vol. 18, pp. 459-469, doi:10.1038/nrn.2017.71 (2017).
Fitzsimons, J.T., "Angiotensin, thirst, and sodium appetite", Physiological reviews, vol. 78, pp. 583-686 (1998).
Wickersham et al., "Monosynaptic restriction of transsynaptic tracing from single, genetically targeted neurons", Neuron, vol. 53, pp. 639-647, doi:10.1016/j.neuron.2007.01.033 (2007).
Yang et al., "Sexually dimorphic neurons in the ventromedial hypothalamus govern mating in both sexes and aggression in males", Cell, vol. 153, pp. 896-909, doi:10.1016/j.cell.2013.04.017 (2013).
Lerner et al., "Intact-brain analyses reveal distinct information carried by SNc dopamine subcircuits", Cell, vol. 162, pp. 635-647 (2015).
Richards et al., "Identification and characterization of GLP-1 receptor-expressing cells using a new transgenic mouse model", Diabetes, vol. 63, pp. 1224-1233, doi:10.2337/db13-1440 (2014).
Petreanu et al., "Channelrhodopsin-2-assisted circuit mapping of long-range callosal projections", Nature neuroscience, vol. 10, pp. 663-668, doi:10.1038/nn1891 (2007).
Betley et al., "Parallel, redundant circuit organization for homeostatic control of feeding behavior", Cell, vol. 155, pp. 1337-1350, doi:10.1016/j.cell.2013.11.002 (2013).
Zocchi et al., "The cellular mechanism for water detection in the mammalian taste system", Nature neuroscience (2017).
Thrasher et al., "Drinking, oropharyngeal signals, and inhibition of vasopressin secretion in dogs", American Journal of Physiology—Regulatory, Integrative and Comparative Physiology, vol. 253, pp. R509-R515 (1987).
Oka et al., "High salt recruits aversive taste pathways", Nature, vol. 494, pp. 472-475 (2013).
Krashes et al., "An excitatory paraventricular nucleus to AgRP neuron circuit that drives hunger", Nature, vol. 507, pp. 238-242, doi:10.1038/nature12956 (2014).
Kahles et al., "GLP-1 secretion is increased by inflammatory stimuli in an IL-6—dependent manner, leading to hyperinsulinemia and blood glucose lowering", Diabetes, vol. 63, pp. 3221-3229, doi:10.2337/db14-0100 (2014).

(Continued)

*Primary Examiner* — Gregory S Emch
(74) *Attorney, Agent, or Firm* — Knobbe, Martens, Olson & Bear, LLP

(57) ABSTRACT

In some embodiments, methods of stimulating fluid intake in a subject in need thereof are described. The methods can comprise stimulating a nitric oxide synthase (nNOS)-positive neuron of the median preoptic nucleus (MnPO). In some embodiments, methods of inhibiting fluid intake in a subject in need thereof are described. The methods can comprise inhibiting stimulation of an nNOS-positive neuron of the MnPO.

10 Claims, 72 Drawing Sheets
Specification includes a Sequence Listing.

(56) References Cited

PUBLICATIONS

Allen et al., "Thirst-associated preoptic neurons encode an aversive motivational drive", Science, vol. 357, pp. 1149-1155, doi:10.1126/science.aan6747 (2017).

Saker et al., "Regional brain responses associated with drinking water during thirst and after its satiation", Proceedings of the National Academy of Sciences 111, 5379-5384 (2014).

Zimmerman et al., "Thirst neurons anticipate the homeostatic consequences of eating and drinking", Nature 537, 680-684 (2016).

Oka et al., "Thirst driving and suppressing signals encoded by distinct neural populations in the brain", Nature, doi:10.1038/nature14108 (2015).

Simpson et al., "A. Subfornical organ: site of drinking elicitation by angiotensin II", Science 181, 1172-1175 (1973).

Stricker et al., "Presystemic signals in the control of thirst, salt appetite, and vasopressin secretion", Physiology & behavior 91, 404-412, doi:10.1016/j.physbeh.2007.04.007 (2007).

Farrell et al., "Cortical activation and lamina terminalis functional connectivity during thirst and drinking in humans", Am J Physiol—Reg I 301, R623-R631, doi:10.1152/ajpregu.00817.2010 (2011).

Denton et al., "Hypothalamic 1 integration of body fluid regulation", Proc Natl Acad Sci U S A 93, 7397-7404 (1996).

Johnson et al., "Sensory circumventricular organs and brain homeostatic pathways", FASEB journal : official publication of the Federation of American Societies for Experimental Biology 7, 678-686 (1993).

Betley et al., "Neurons for hunger and thirst transmit a negative-valence teaching signal", Nature 521, 180-185, doi:10.1038/nature14416 (2015).

Nation et al., "DREADD—induced activation of subfornical organ neurons stimulates thirst and salt appetite", Journal of neurophysiology 115, 3123-3129 (2016).

Abbott et al., "Reciprocal Control of Drinking Behavior by Median Preoptic Neurons in Mice", J Neurosci 36, 8228-8237, doi:10.1523/jneurosci.1244-16.2016 (2016).

Matsuda et al., "Distinct neural mechanisms for the control of thirst and salt appetite in the subfornical organ", Nature neuroscience 20, 230-241, doi:10.1038/nn.4463 (2017).

Miselis et al., "Subfornical organ efferents to neural systems for control of body water", Science 205, 1022-1025 (1979).

Roth, B. L., "DREADDs for Neuroscientists", Neuron 89, 683-694, doi:10.1016/j.neuron.2016.01.040 (2016).

Cunningham et al., "The effects of ibotenate lesions of the median preoptic nucleus on experimentally-induced and circadian drinking behavior in rats", Brain research 580, 325-330 (1992).

McKinley et al., "Effect of individual or combined ablation of the nuclear groups of the lamina terminalis on water drinking in sheep", American Journal of Physiology—Regulatory, Integrative and Comparative Physiology, 276, R673-R683 (1999).

McKinley et al., "The median preoptic nucleus: 1 front and centre for the regulation of body fluid, sodium, temperature, sleep and cardiovascular homeostasis", Acta physiologica 214, 8-32, doi:10.1111/apha.12487 (2015).

Abbott, Stephen B.G. et al., "Median preoptic glutamatergic neurons promote thermoregulatory heat loss and water consumption in mice" The Journal of Physiology, 2017, pp. 6569-6583, vol. 595.

Ciura, Sorana et al., "Hypertonicity Sensing in Organum Vasculosum Lamina Terminalis Neurons: A Mechanical Process Involving TRPV1 but Not TRPV4" The Journal of Neuroscience, Oct. 2011, pp. 14669-14676, vol. 31, No. 41.

Hatzelmann, T. et al., "Functional Expression of the Apelin-12 Receptor Protein APJ in Rat Hypothalamic Nuclei (PVN and MnPO) Involved in Body Fluid Homeostasis and Temperature Regulation" Acta Physiologica, 2009, vol. 195, Supplement 669, P460, Abstract.

International Search Report for PCT/US2019/013341 dated Mar. 22, 2019.

Bedenbaugh et al., "Kisspeptin, GnRH, and ERα colocalise with nNOS neurones in prepubertal female sheep", J Neuroendocrinol., vol. 30, No. 1, Jan. 2018, pp. 1-22.

Ichiki et al., "Neural populations for maintaining body fluid balance", Curr Opin Neurobiol., vol. 57, Aug. 2019, pp. 134-140.

\* cited by examiner

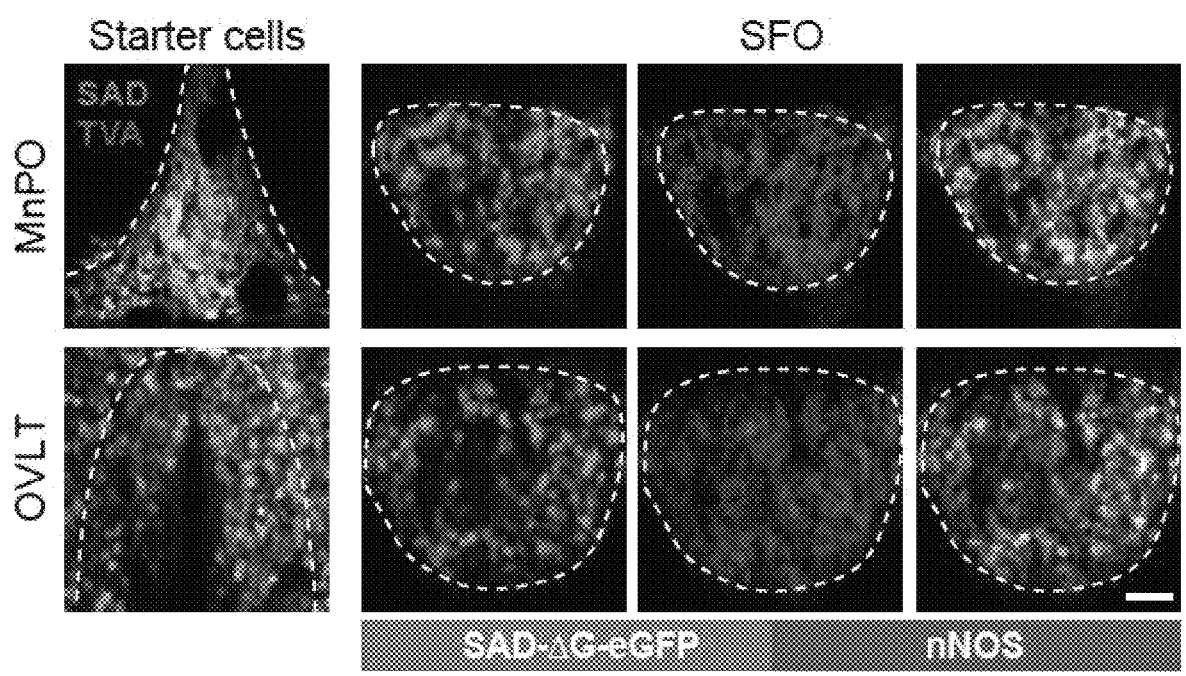
FIG. 1B                    FIG. 1C

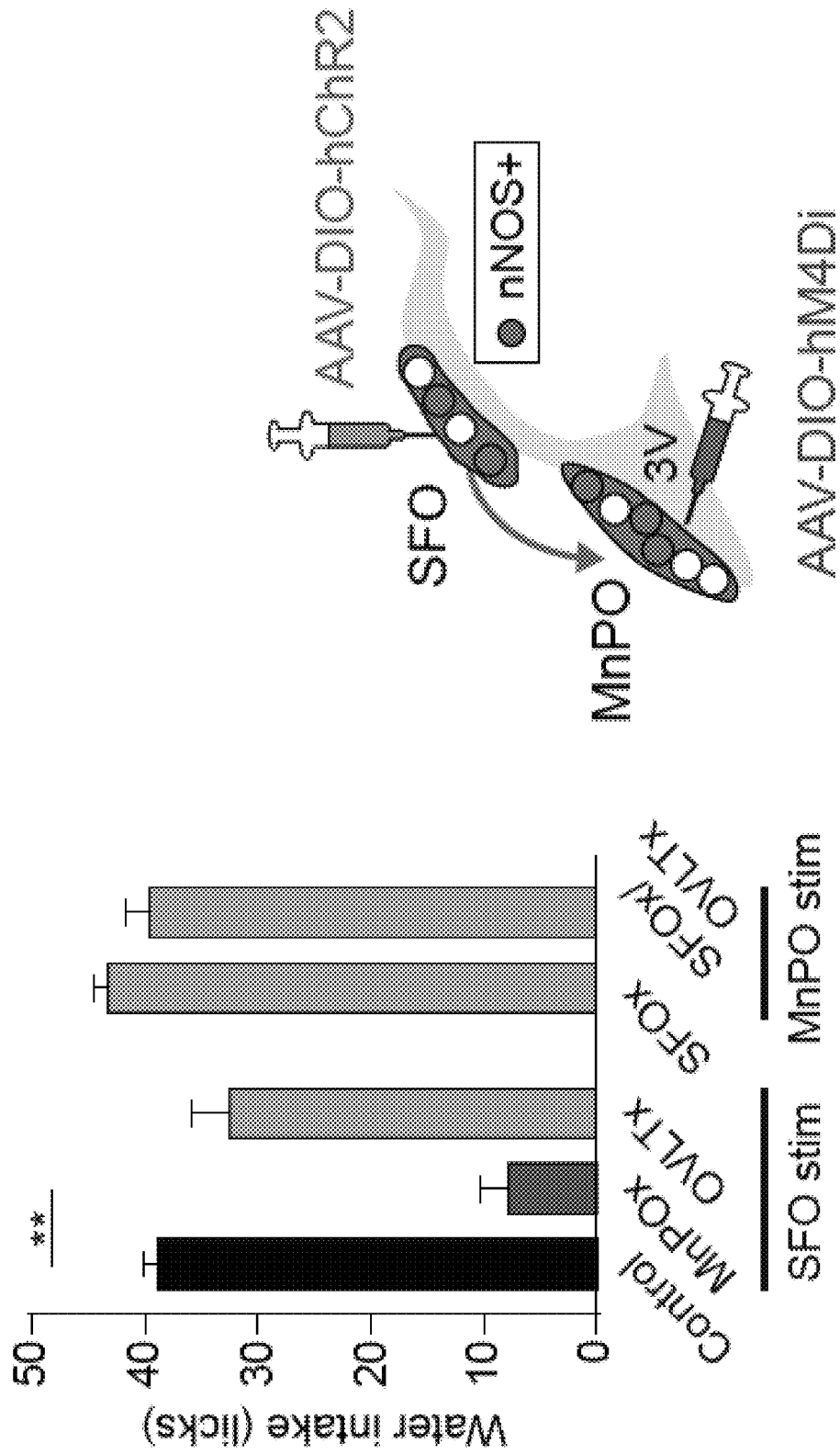

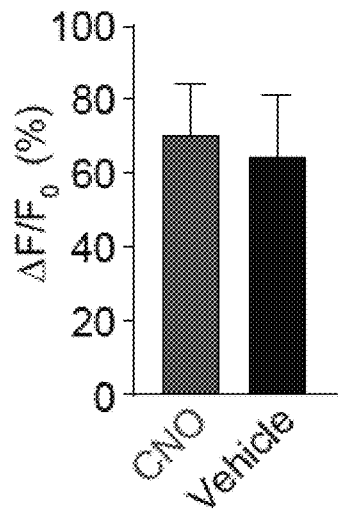
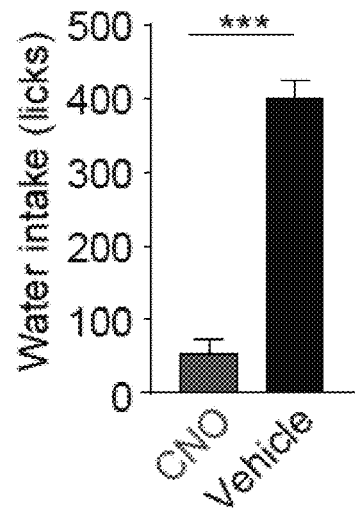
FIG. 1Q         FIG. 1R
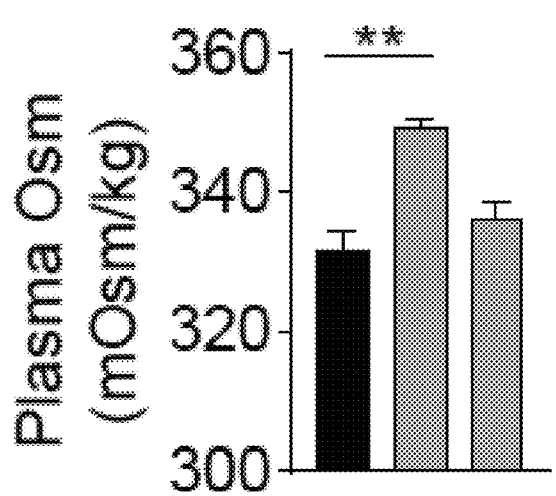
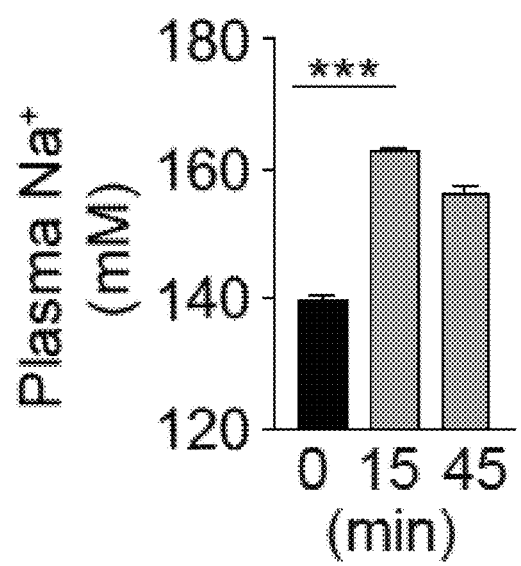
FIG. 1S         FIG. 1T

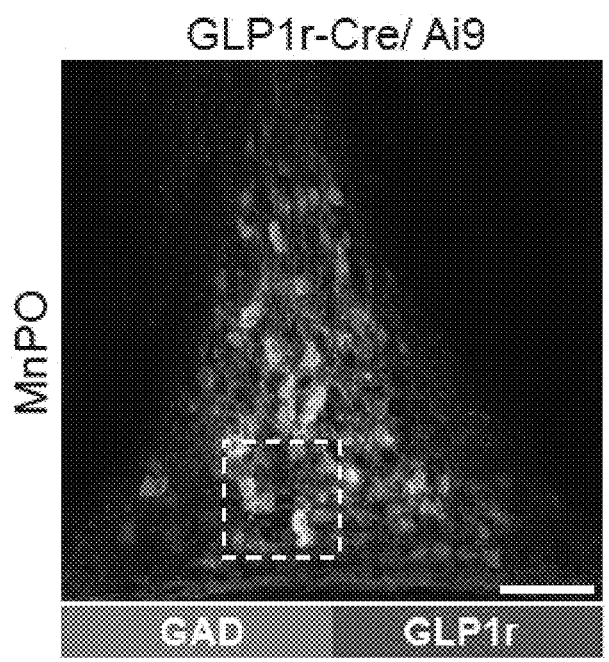
FIG. 2D
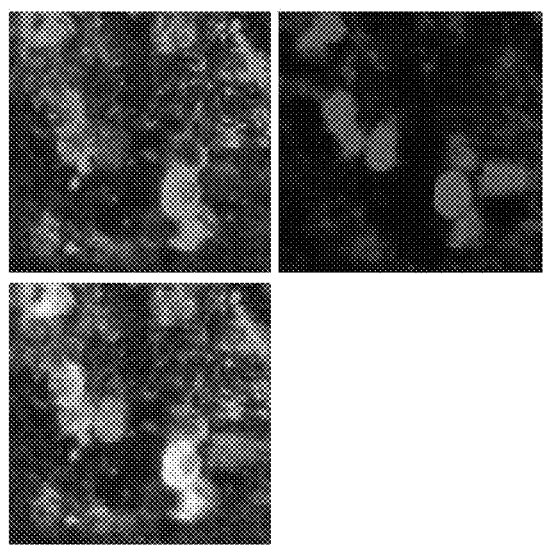
FIG. 2E  FIG. 2F
FIG. 2G

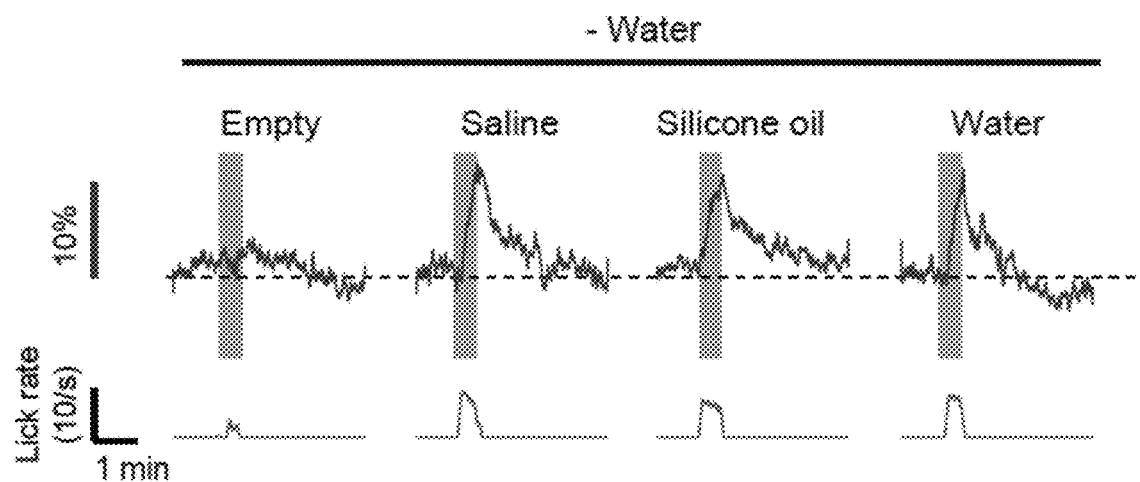
FIG. 3D
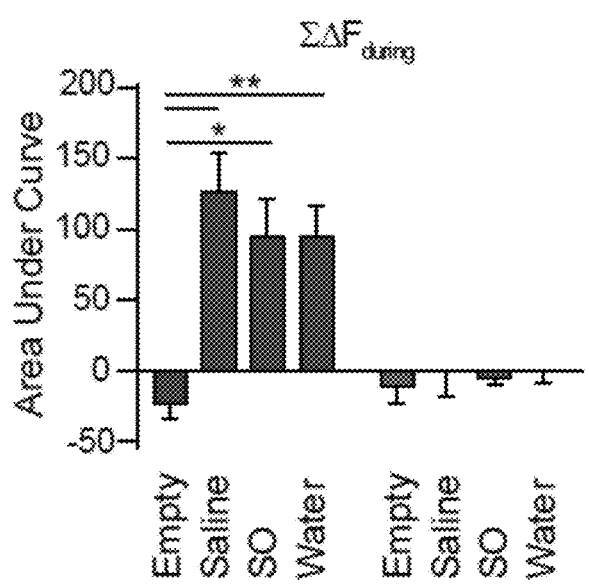 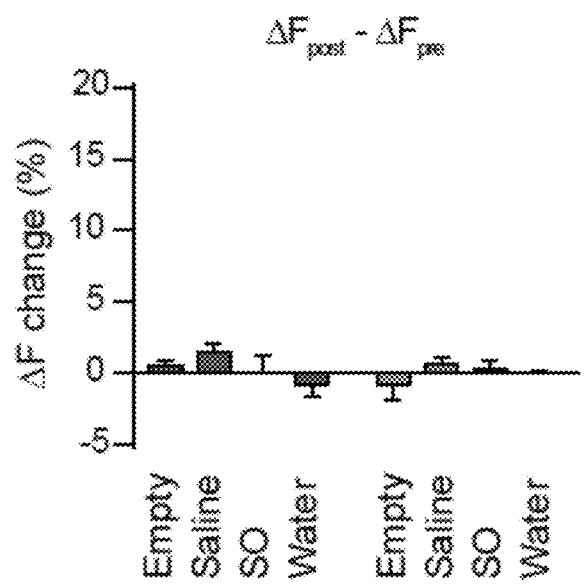
FIG. 3E  FIG. 3F

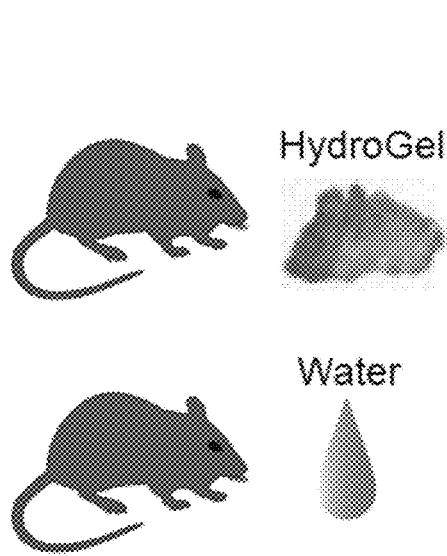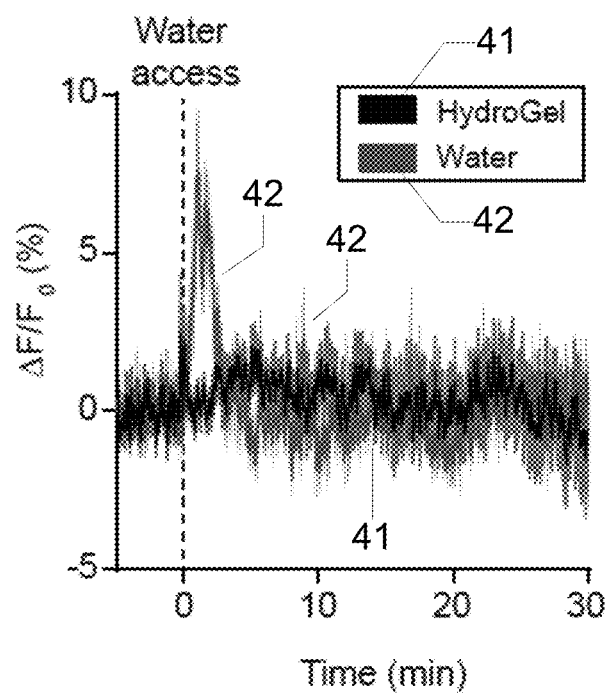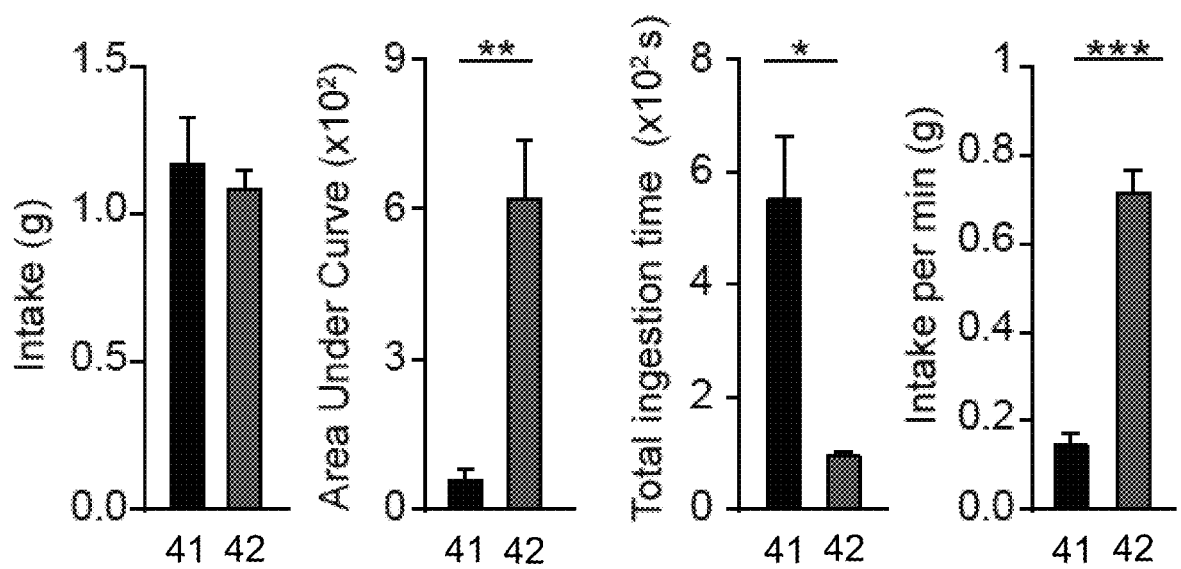
FIG. 4A  FIG. 4B
FIG. 4C  FIG. 4D  FIG. 4E  FIG. 4F

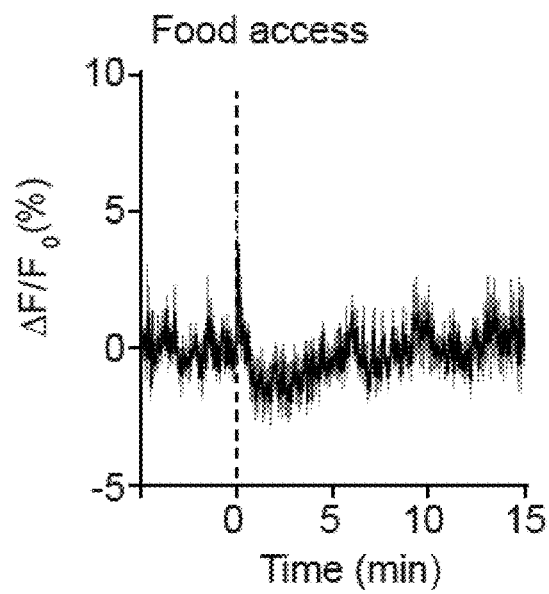
FIG. 4K
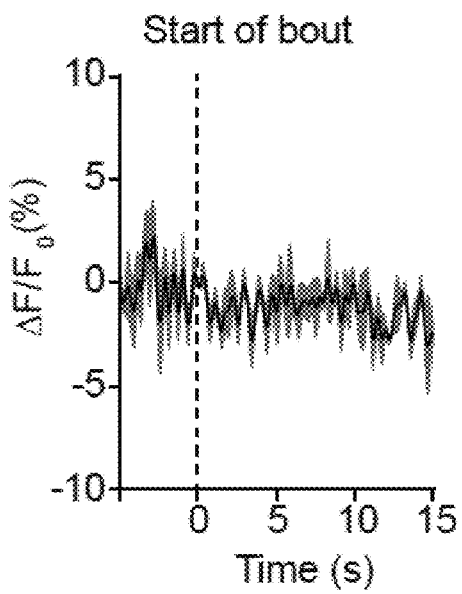
FIG. 4L
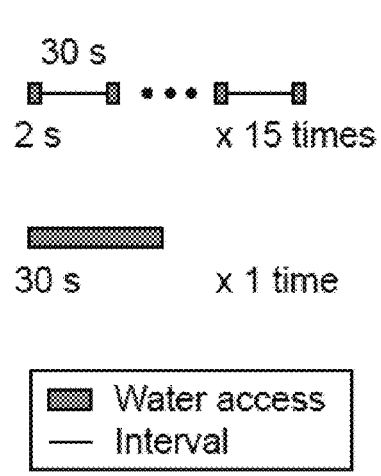
FIG 4M
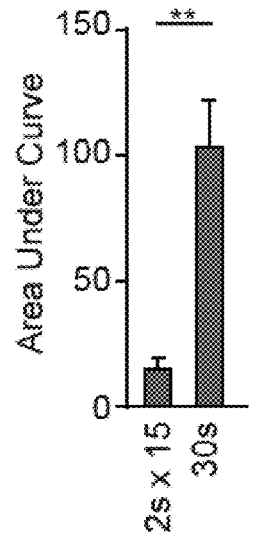
FIG. 4N
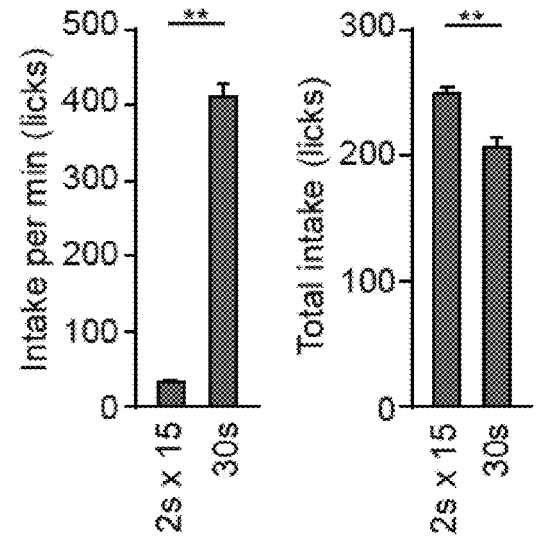
FIG. 4O   FIG. 4P

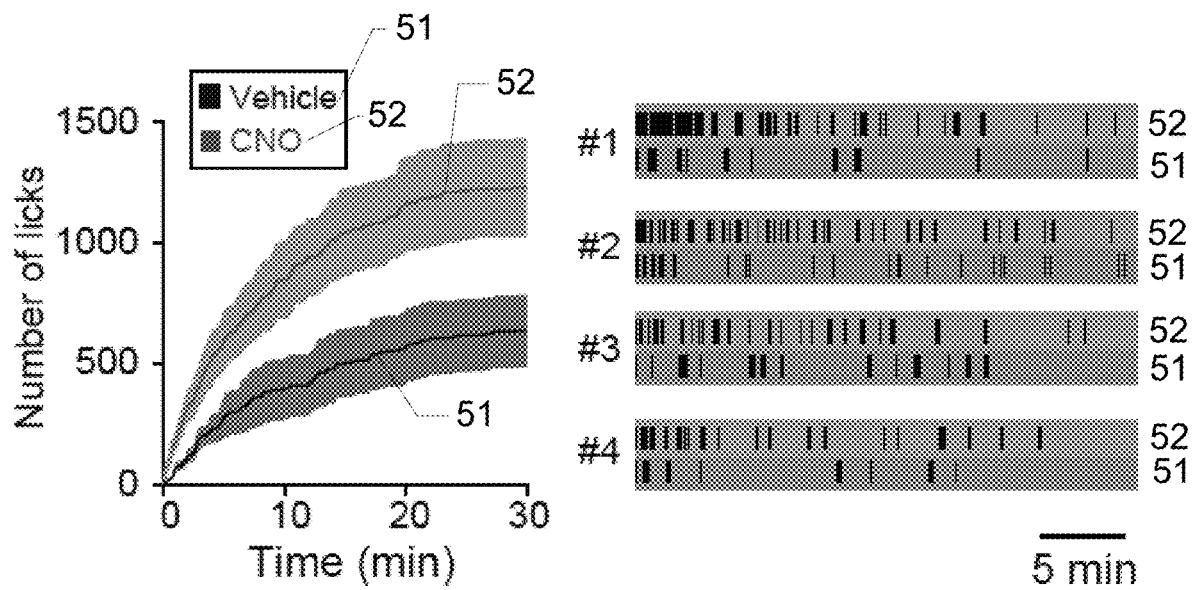
FIG. 5D  FIG. 5E
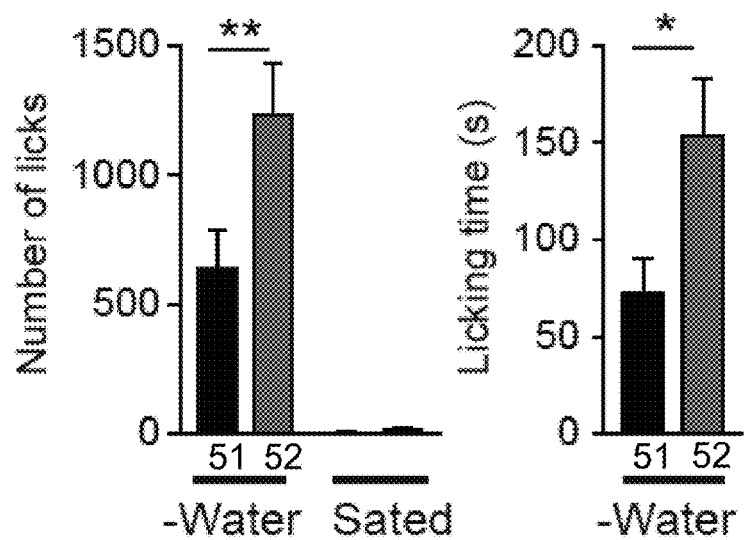
FIG. 5F  FIG. 5G

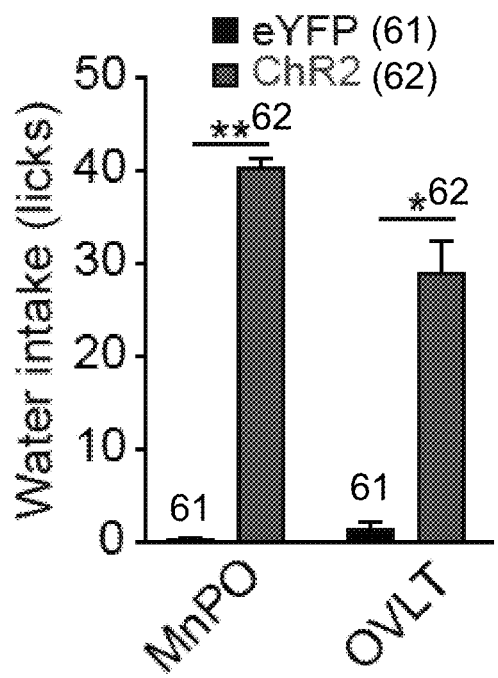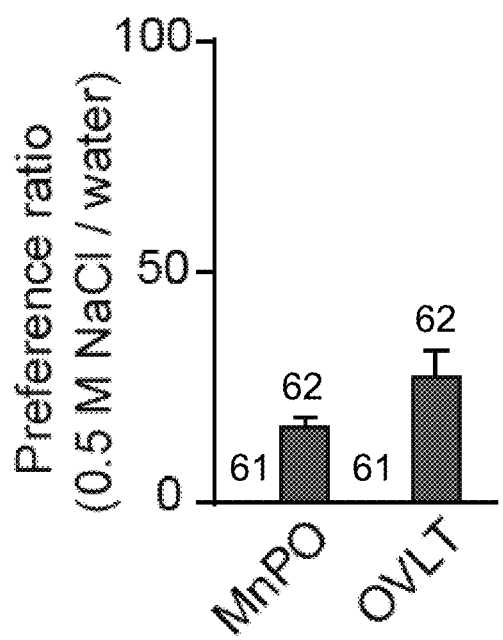
FIG. 6I
FIG. 6J
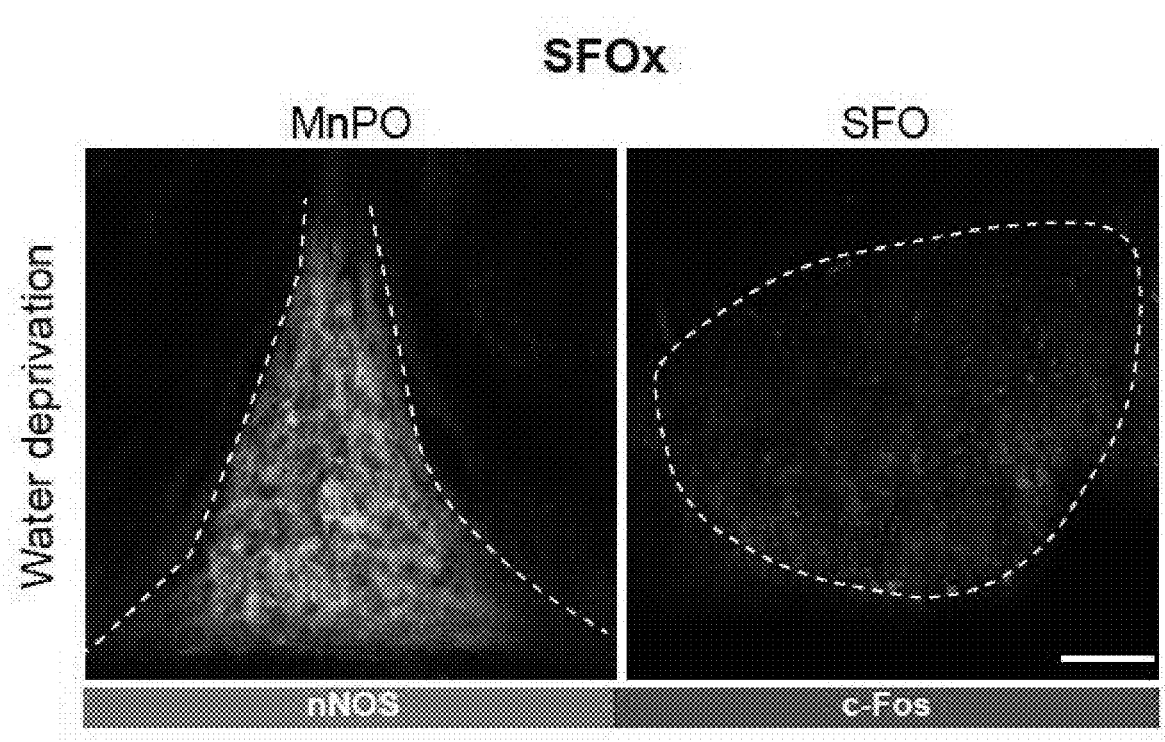
FIG. 7A
FIG. 7B

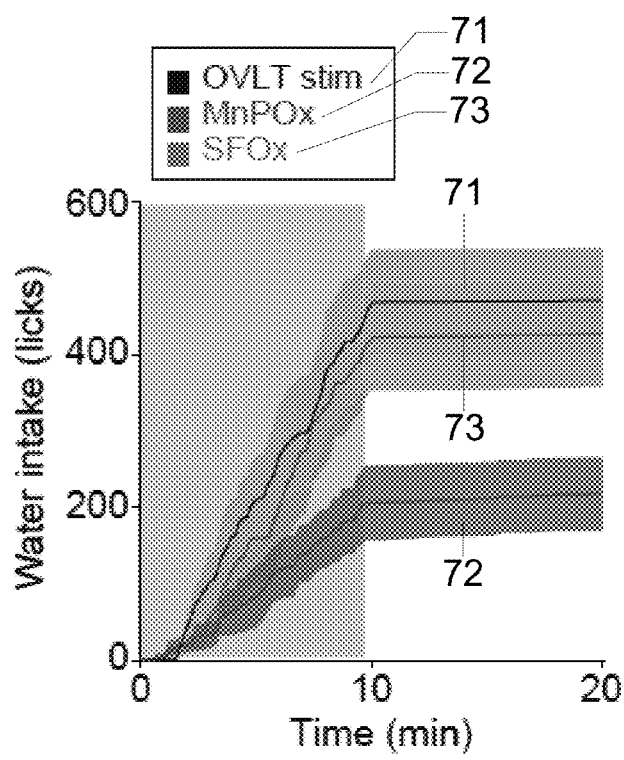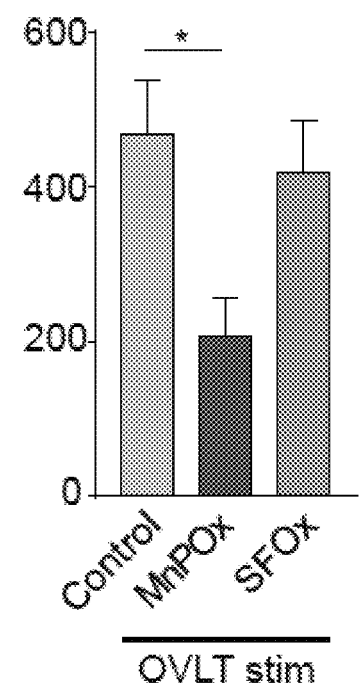
FIG. 7G  FIG. 7H

FIG. 7I  FIG. 7J  FIG. 7K

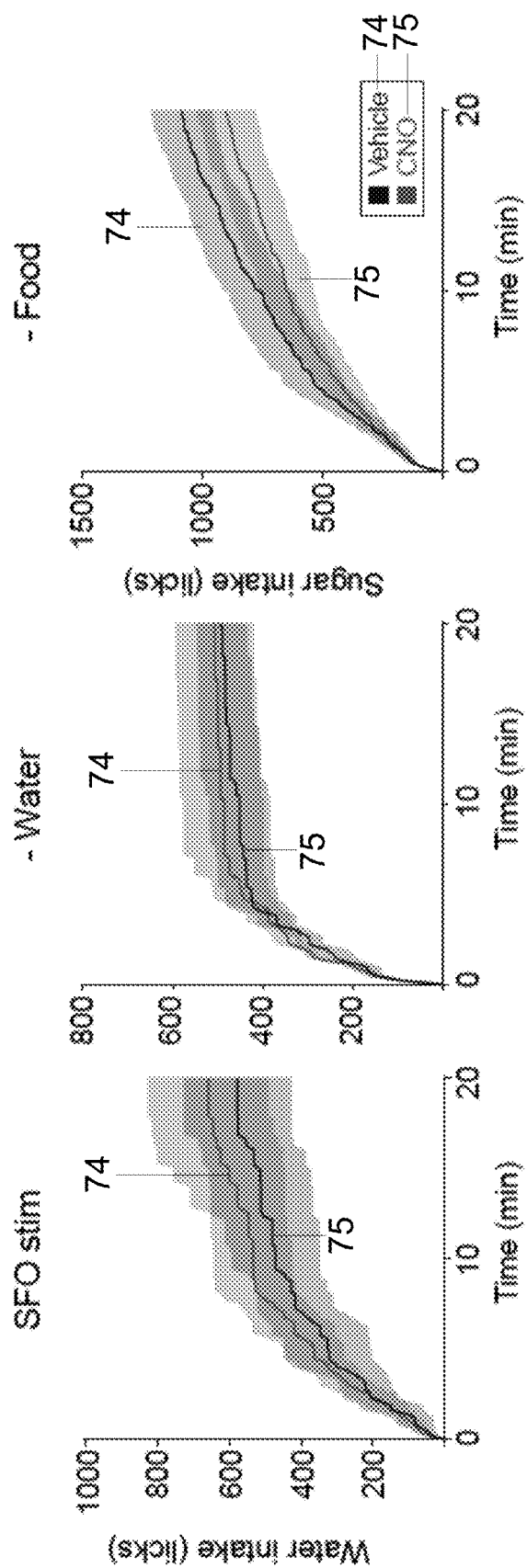

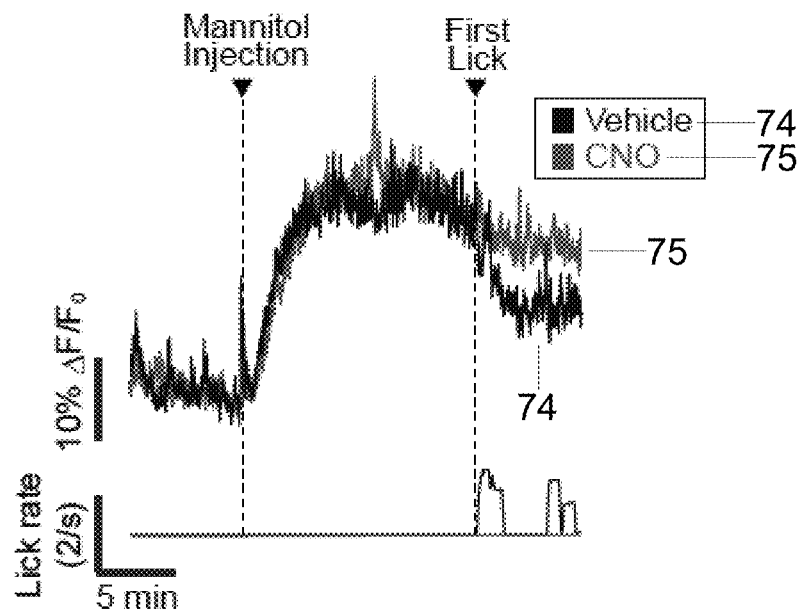
FIG. 7P
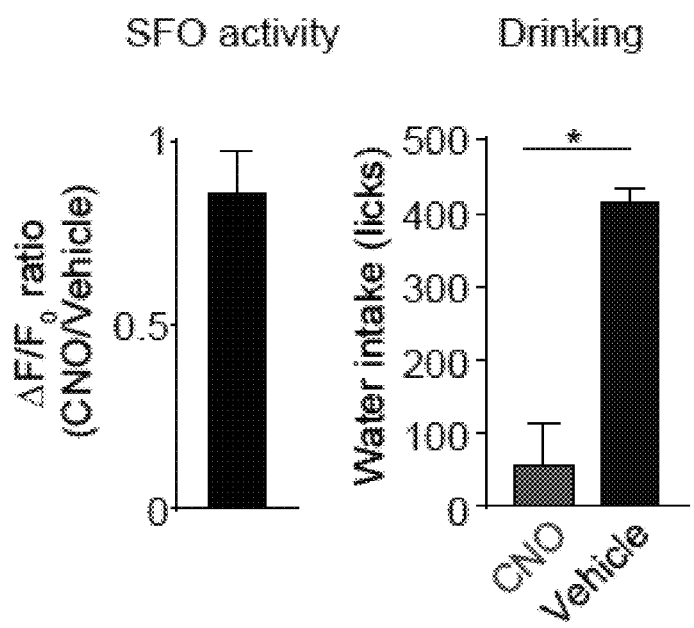
FIG. 7Q   FIG. 7R

FIG. 7S
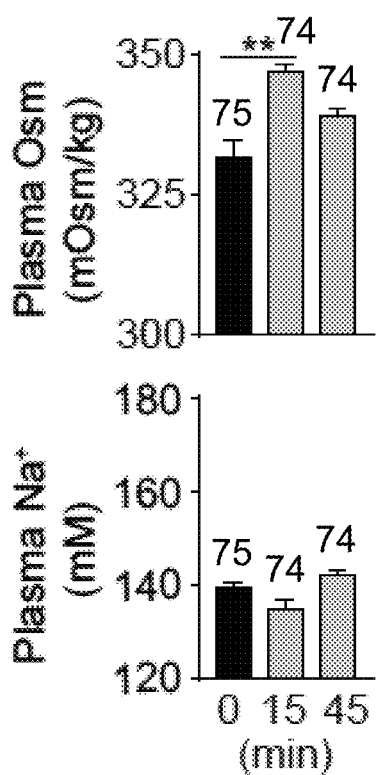
FIG. 7T
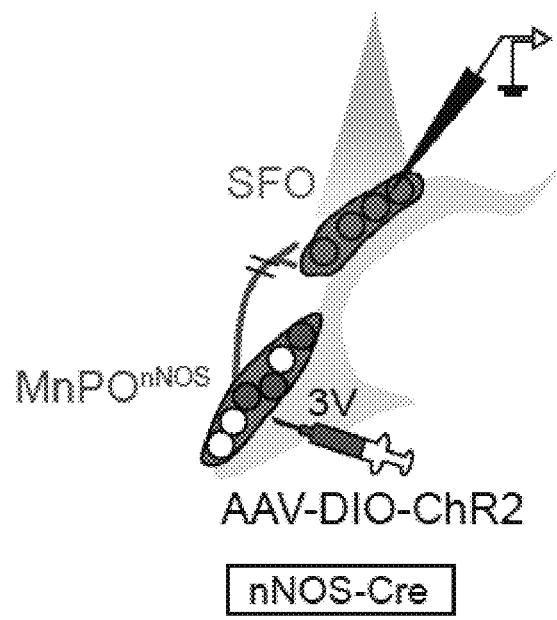
FIG. 8A

FIG. 9E
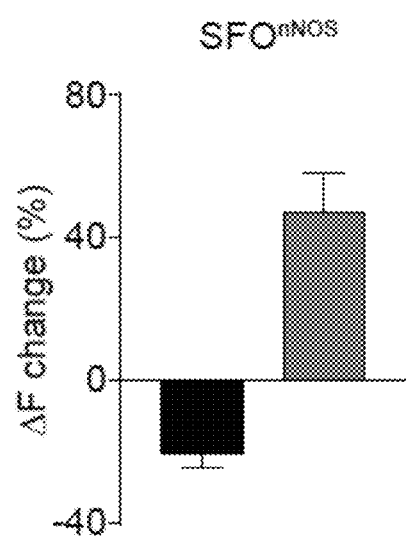
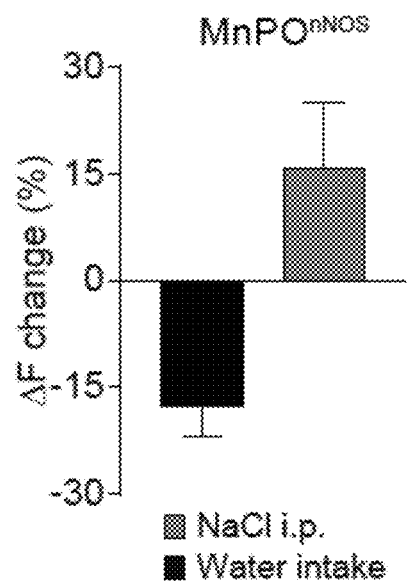
FIG. 9F

MnPO

LS

MS

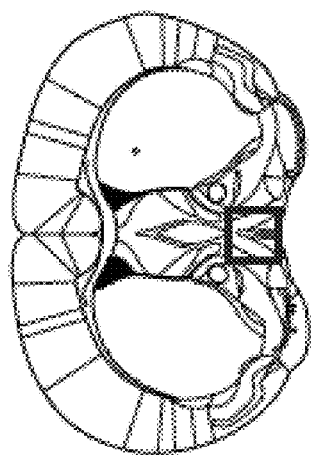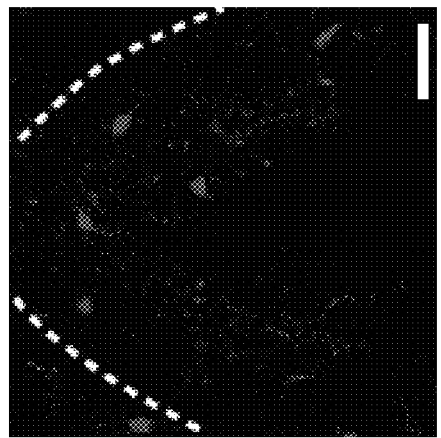
FIG. 10G OVLT
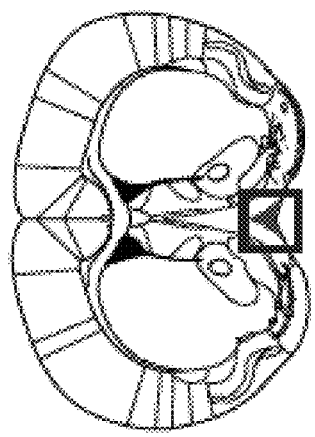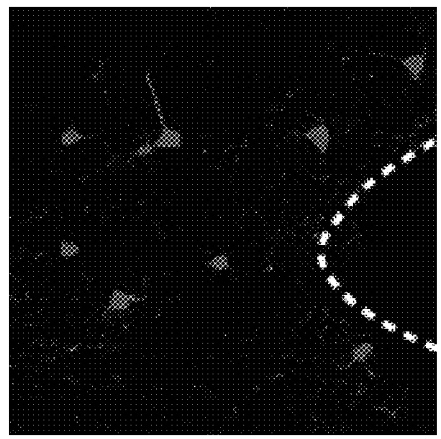
FIG. 10F MPA
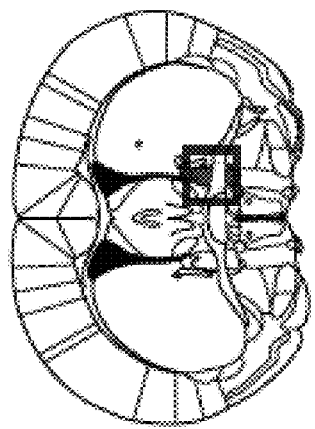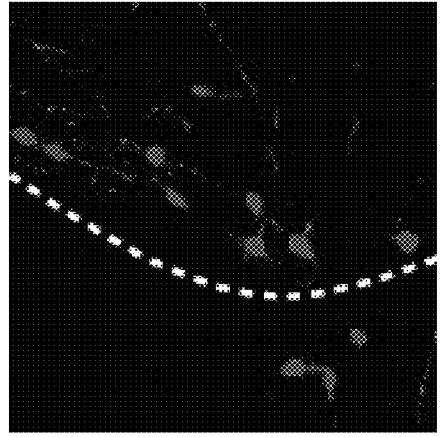
FIG. 10E BNST

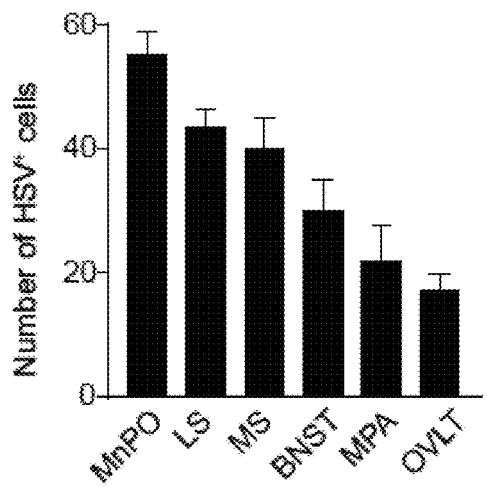
FIG. 10H
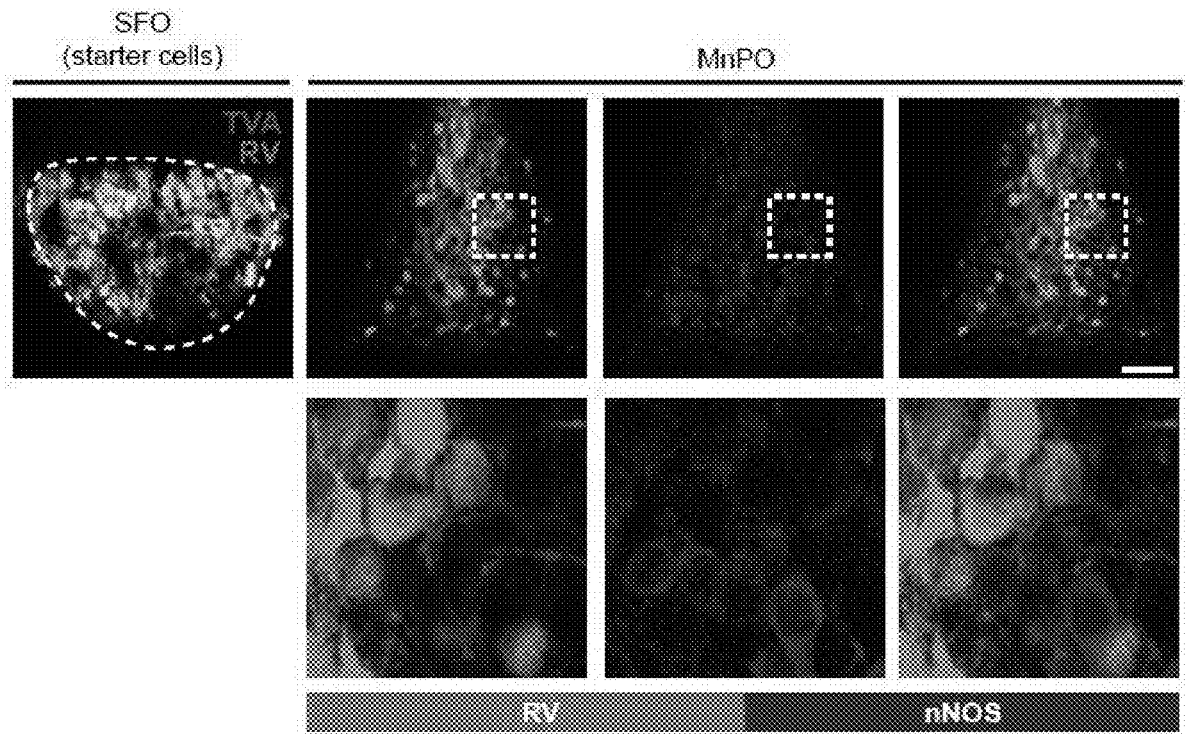
FIG. 10I　　　FIG. 10J

FIG. 11D    FIG. 11E

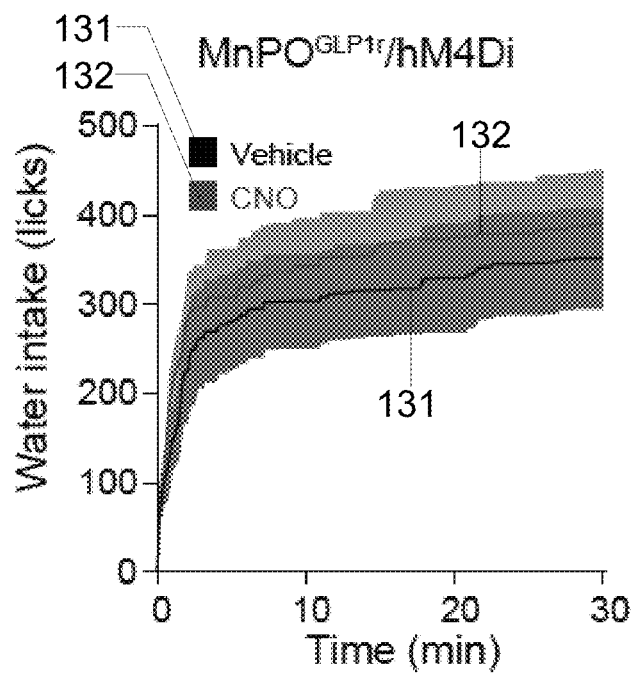
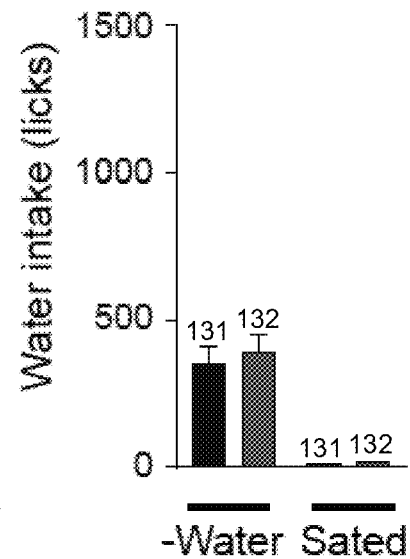
FIG. 13A          FIG. 13B
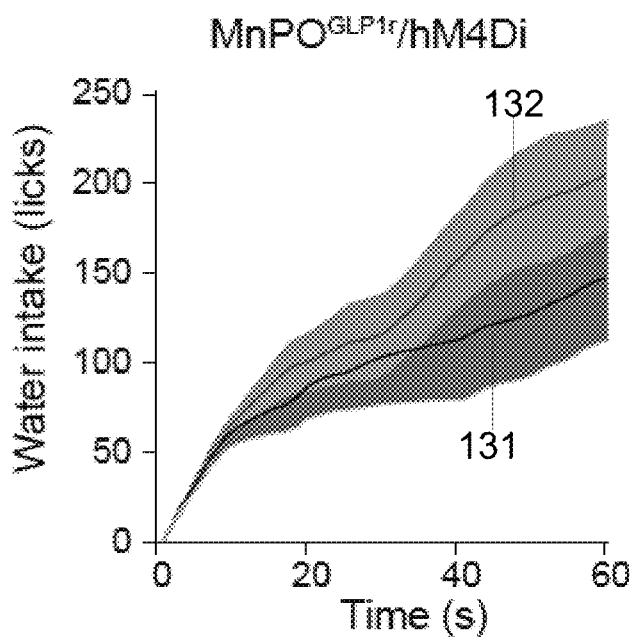
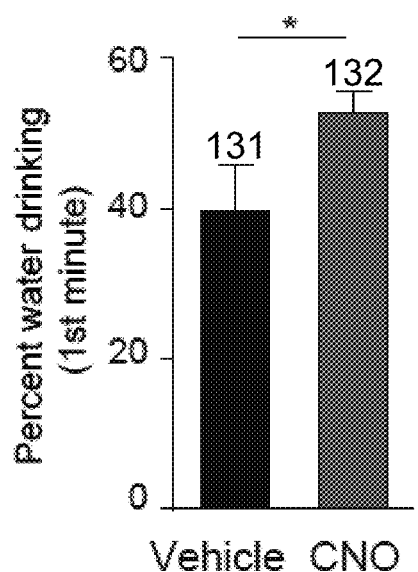
FIG. 13C          FIG. 13D

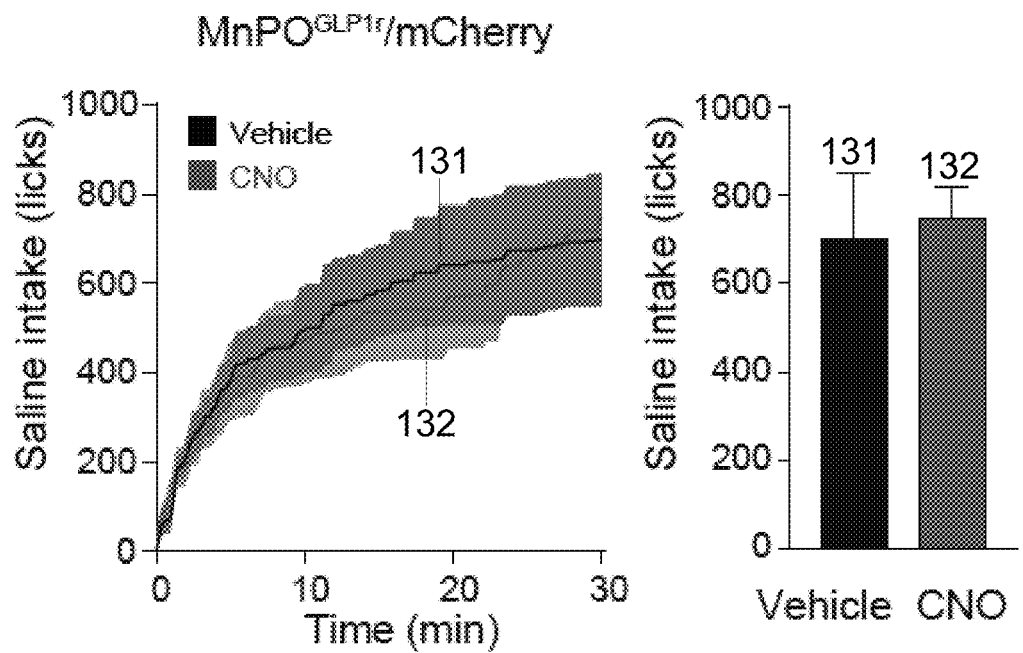
FIG. 13E  FIG. 13F
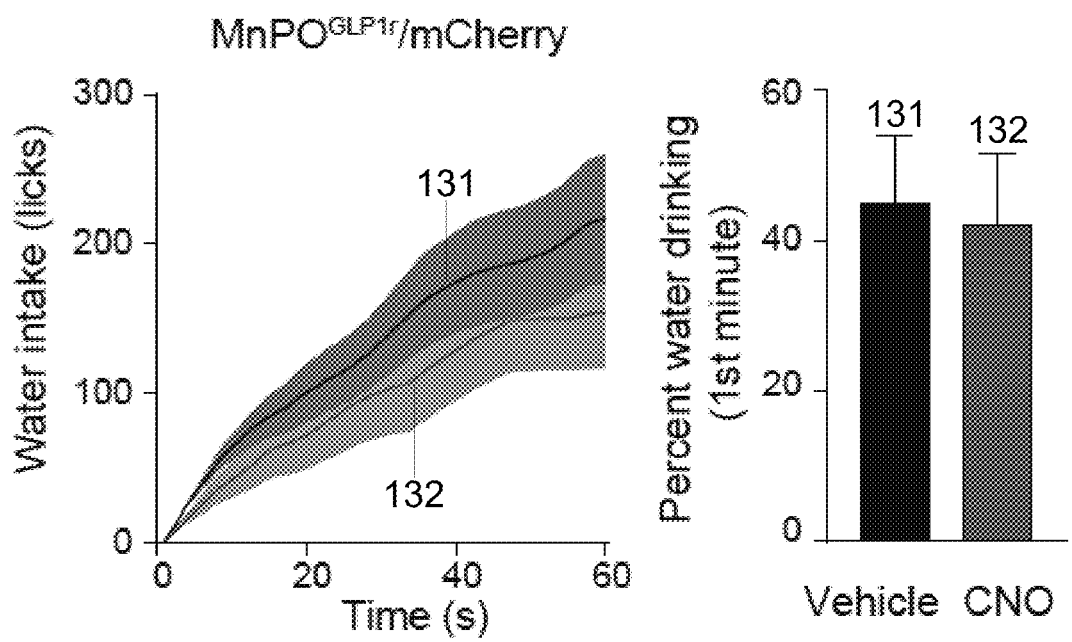
FIG. 13G  FIG. 13H

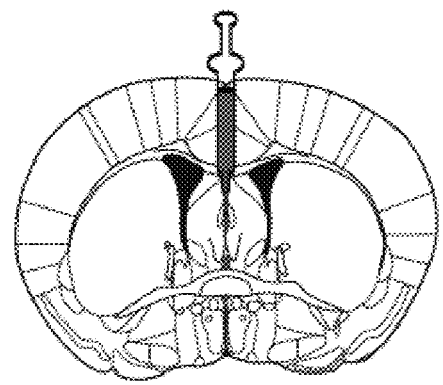
FIG. 13I
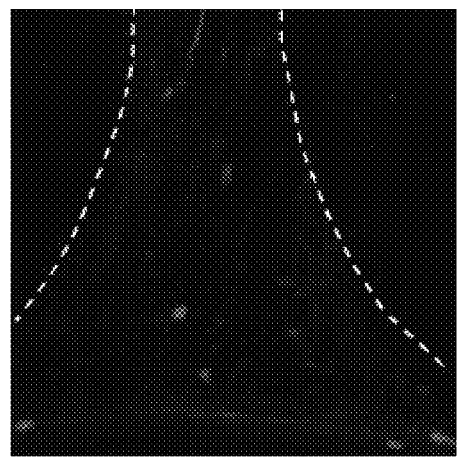 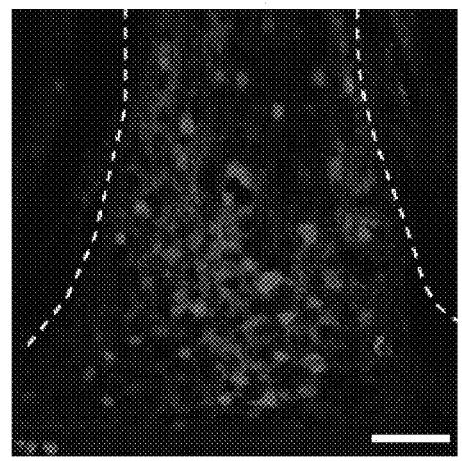
FIG. 13J      FIG. 13K

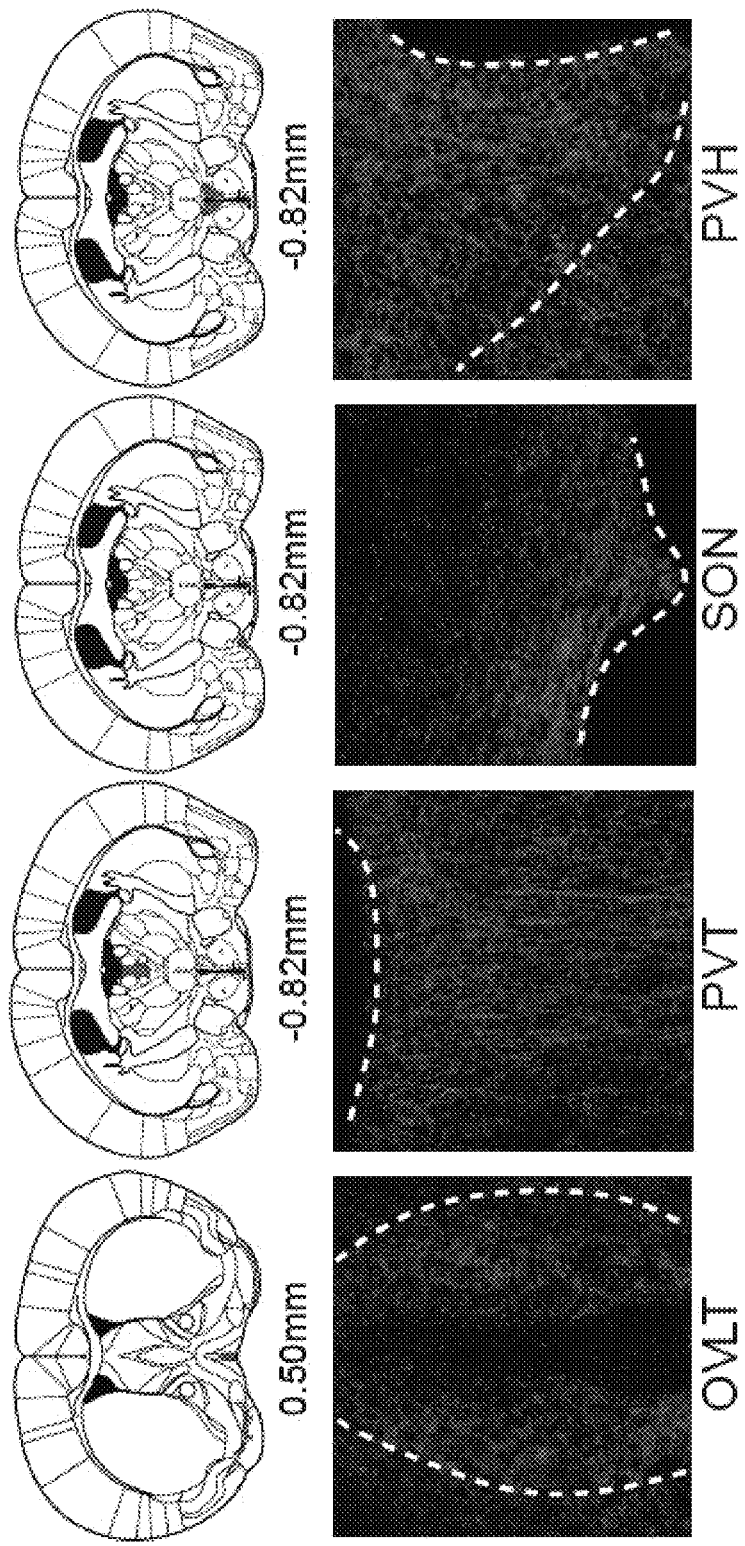

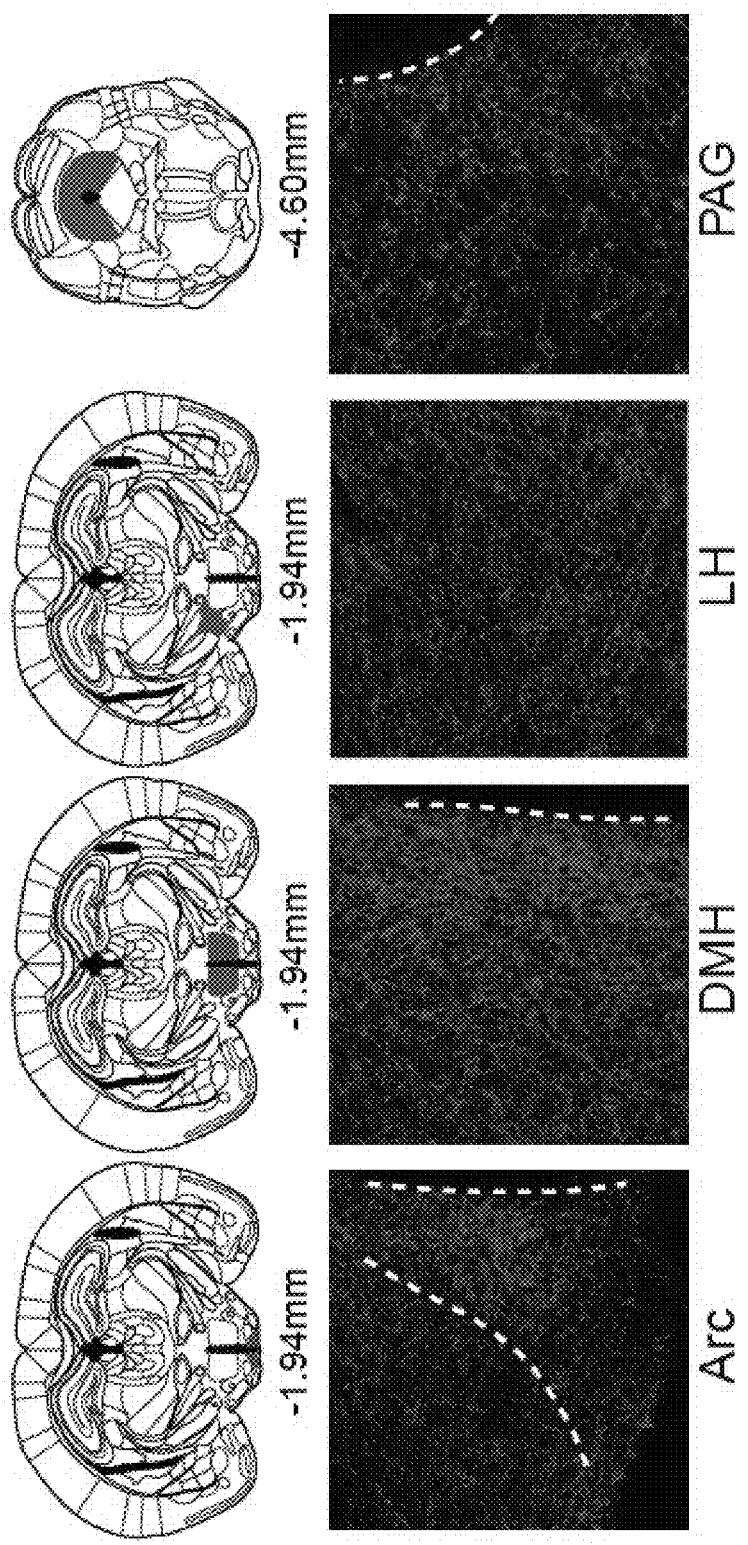

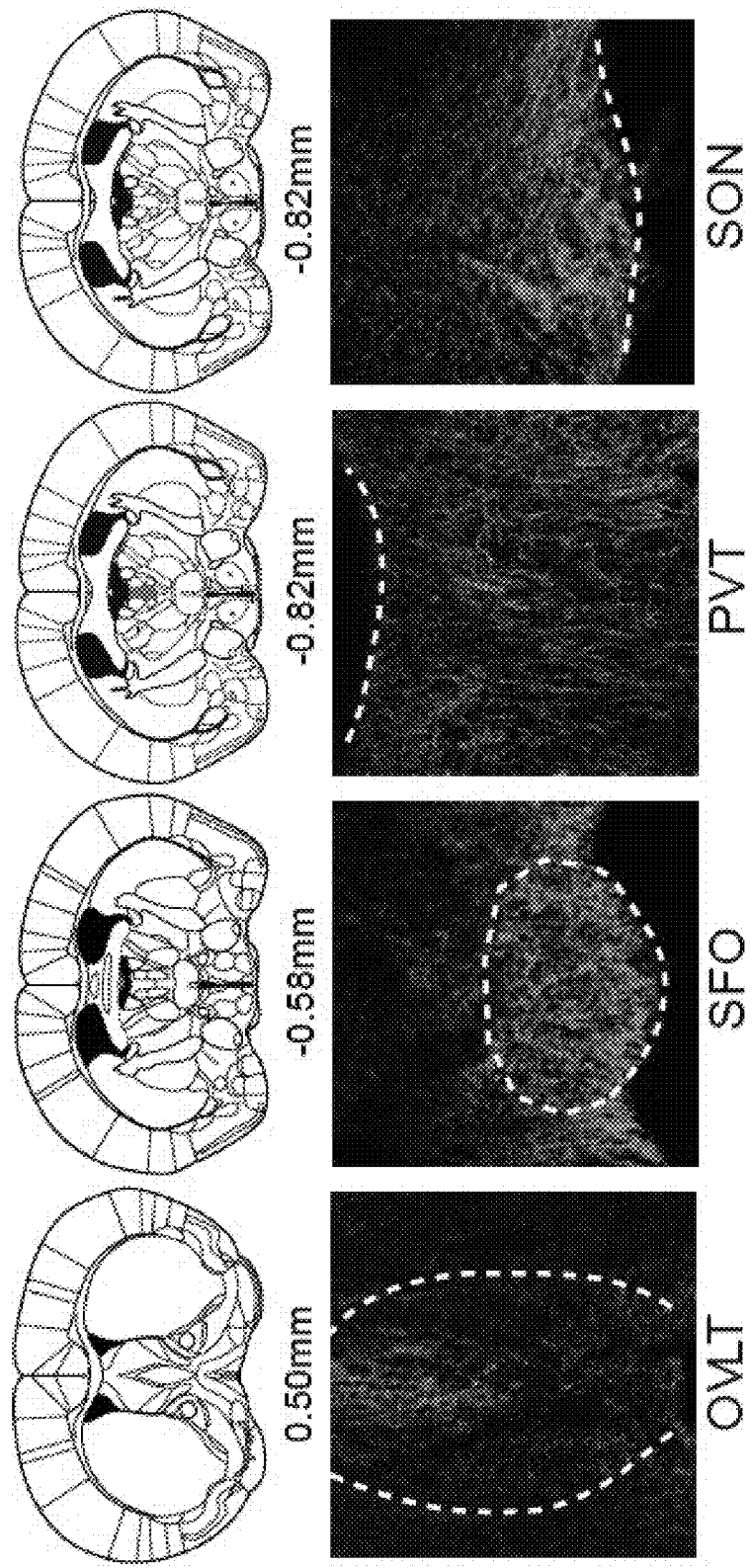

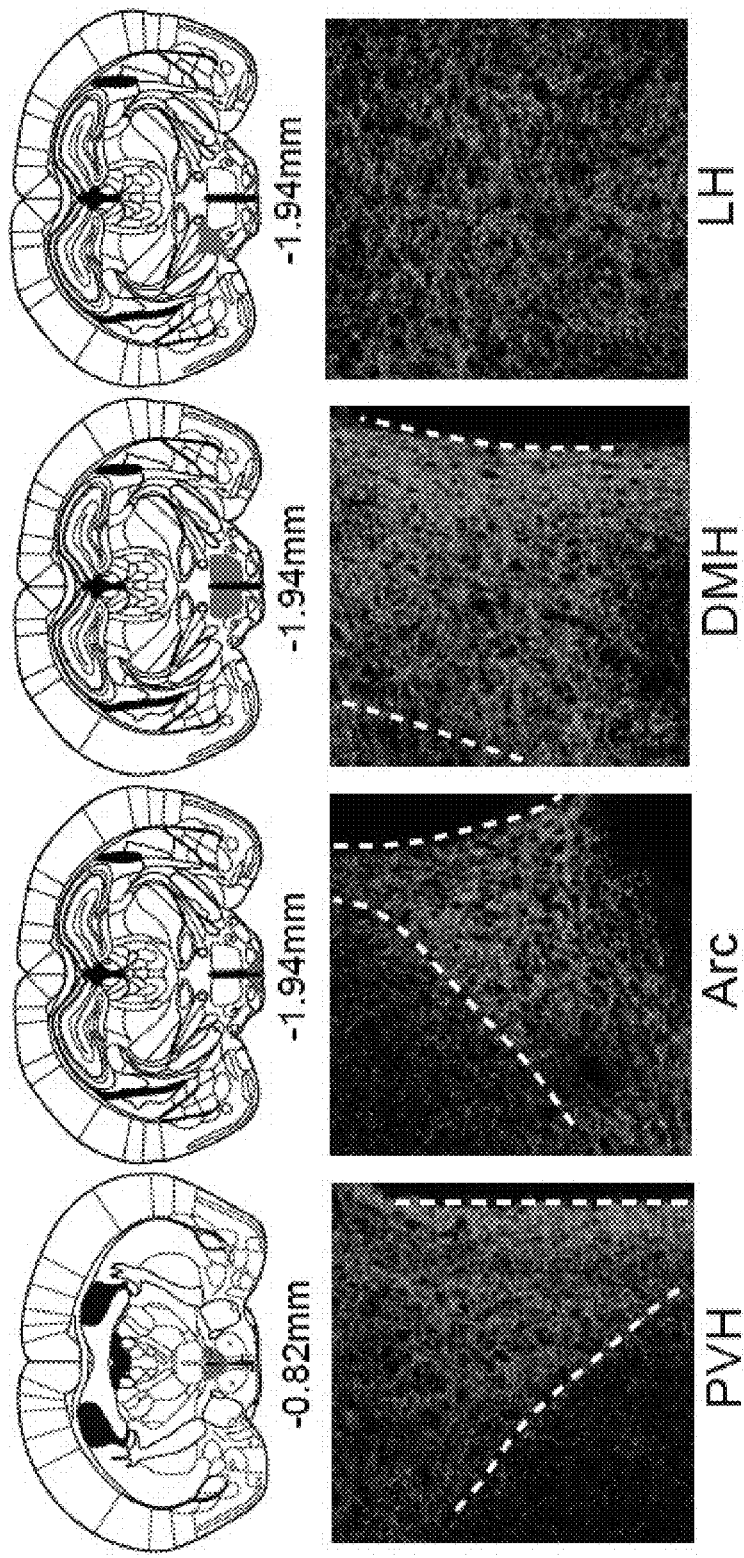

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Targeting Peptide

<400> SEQUENCE: 1

Thr Leu Ala Val Pro Phe Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Targeting Peptide

<400> SEQUENCE: 2

Ser Val Ser Lys Pro Phe Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Targeting Peptide

<400> SEQUENCE: 3

Phe Thr Leu Thr Thr Pro Lys
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Targeting Peptide

<400> SEQUENCE: 4

Tyr Thr Leu Ser Gln Gly Trp
1               5

<210> SEQ ID NO 5
<211> LENGTH: 7
<212> TYPE: PRT
<213> ORGANISM: Artificial Sequence
<220> FEATURE:
<223> OTHER INFORMATION: Targeting Peptide

<400> SEQUENCE: 5

Gln Ala Val Arg Thr Ser Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Targeting Peptide

<400> SEQUENCE: 6

Leu Ala Lys Glu Arg Leu Ser
1               5
```

MODULATION OF FLUID INTAKE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims the benefit of U.S. Provisional Application No. 62/616,963, filed Jan. 12, 2018, which is hereby incorporated by reference in its entirety.

STATEMENT REGARDING FEDERALLY SPONSORED R&D

This invention was made with government support under Grant No. NS099717 & MH113030 awarded by the National Institutes of Health. The government has certain rights in the invention.

REFERENCE TO SEQUENCE LISTING

The present application is being filed along with a Sequence Listing in electronic format. The Sequence Listing is provided as a file CALTE136ASEQUENCE.txt, created and last modified on Jan. 10, 2019, which is 1,340 bytes in size. The information in the electronic format of the Sequence Listing is incorporated herein by reference in its entirety.

BACKGROUND

Dynamic thirst circuits integrate the homeostatic-instinctive need and its consequent drinking behavior to maintain internal water balance. The precise regulation of water intake plays a significant role in maintaining body fluid homeostasis. The initiation of water drinking is triggered by internal fluid imbalance in animals such as water depletion. In contrast, drinking termination rapidly occurs when animals ingest a sufficient amount of water, which generally precedes the absorption of ingested fluid. To achieve such accurate fluid regulation, the brain monitors both internal water balance as well as fluid ingestion on a real-time basis.

FIELD

Some embodiments relate to methods and compositions for stimulating or inhibiting fluid intake in a subject in need thereof.

SUMMARY

In some embodiments, a method of stimulating fluid intake in a subject in need of such stimulating is described. The method can comprise, in a first nitric oxide synthase (nNOS)-positive neuron of the median preoptic nucleus (MnPO) comprising a polarized cell membrane, stimulating depolarization of the cell membrane. The, the first nNOS-positive neuron can be stimulated, thus stimulating fluid intake in the subject. In some embodiments, stimulating depolarization of the cell membrane comprises a net influx of cations into a cytosol of the first nNOS-positive neuron, a net efflux of anions from the cytosol of the first nNOS-positive neuron, stimulating a second nNOS-positive neuron of the subfornical organ (SFO), or a combination of these. In some embodiments, stimulating depolarization of the cell membrane of the first nNOS-positive neuron comprises administering a nucleic acid encoding a stimulatory conditional ion modulator to the subject. The stimulatory conditional ion modulator can be configured to induce a net influx of cations into and/or a net efflux of anions from the cytosol of the first nNOS-positive neuron in response to a stimulus or agonist. The nucleic acid can be under the control of a promoter that induces transcription of the nucleic acid in the first nNOS-positive neuron, so that the conditional ion modulator is expressed in the first nNOS-positive neuron. The method can comprise applying an agonist or stimulus to the first nNOS-positive neuron of the subject, causing the conditional ion modulator to induce the net influx of cations into the cytosol of the first nNOS-positive neuron and/or the net efflux of anions from the cytosol of the first nNOS-positive neuron. In some embodiments, the stimulatory conditional ion modulator comprises a hM3DREADD and the agonist comprises clozapine-N-oxide, or the conditional ion modulator comprises a channelrhodopsin and the agonist comprises electromagnetic radiation. In some embodiments, the nucleic acid is administered to the subject in an adeno-associated viral (AAV) vector. In some embodiments, stimulating depolarization of the cell membrane comprises inhibiting a glucagon-like peptide-1 receptor (GLP1r)-positive neuron of the MnPO. In some embodiments, inhibiting the GLP1r-positive neuron comprises administering a nucleic acid encoding an inhibitory conditional ion modulator to the subject, the inhibitory conditional ion modulator configured to inhibit depolarization of a cell membrane of the GLP1r-positive neuron by inducing a net efflux of cations from a cytosol of the GLP1r-positive neuron and/or inducing a net influx of anions into the cytosol of the GLP1r-positive neuron in response to a stimulus or agonist. The nucleic acid can be under the control of a promoter that induces transcription of the nucleic acid in the GLP1r-positive neuron, so that the inhibitory conditional ion modulator is expressed in the GLP1r-positive neuron. The method can comprise applying an agonist or stimulus to the GLP1r-positive neuron of the subject, causing the inhibitory conditional ion modulator to induce the net efflux of cations from the cytosol and/or the next influx of anions into the cytosol of the GLP1r-positive neuron. In some embodiments, the inhibitory conditional ion modulator comprises a hM4Di and the agonist or stimulus comprises clozapine-N-oxide (CNO). In some embodiments, the inhibitory conditional ion modulator comprises halorhodopsin, and/or archaeorhodopsin and the agonist or stimulus comprises electromagnetic radiation. In some embodiments, the method further comprises identifying the subject as in need of stimulating fluid intake. In some embodiments, the subject suffers from dehydration, adipsia, or hypodipsia. In some embodiments, the subject suffers from dehydration, adipsia, hypodipsia, or a kidney disease, dysfunction, disorder, or damage (such as kidney stones). In some embodiments, the fluid intake comprises drinking behavior.

In some embodiments, a method of inhibiting fluid intake in a subject in need such inhibiting is described. The method can comprise, in a first nitric oxide synthase (nNOS)-positive neuron of the median preoptic nucleus (MnPO) comprising a polarized cell membrane, inhibiting depolarization of the cell membrane, thus inhibiting stimulation of the first nNOS-positive neuron, thus inhibiting fluid intake. In some embodiments, inhibiting depolarization of the cell membrane comprises: inhibiting cation influx into a cytosol of the first nNOS-positive neuron, inducing anion influx into the cytosol of the first nNOS-positive neuron inducing cation efflux from the cytosol of the first nNOS-positive neuron, inhibiting a second nNOS-positive neuron of the subfornical organ (SFO), stimulating a GLP1r-positive neuron of the MnPO, or a combination of two or more of the listed items. In some embodiments, inhibiting depolarization of the cell membrane comprises administering a nucleic acid encoding an inhibitory conditional ion modulator to the subject, the inhibitory conditional ion modulator configured to induce a net efflux of cations from and/or a net influx of anions into the cytosol of the first nNOS-positive neuron in response to a stimulus or agonist. The nucleic acid can be under the control of a promoter that induces transcription of the nucleic acid in the first nNOS-positive neuron, so that the conditional ion modulator is expressed in the first nNOS-positive neuron. The method can comprise applying an agonist or stimulus to the first nNOS-positive neuron of the subject, causing the inhibitory conditional ion modulator to induce the net efflux of cations from and/or the net influx of anions into the cytosol of the first nNOS-positive neuron. In some embodiments, the inhibitory conditional ion modulator comprises a hM4Di and the agonist or stimulus comprises clozapine-N-oxide (CNO). In some embodiments, the inhibitory conditional ion modulator comprises halorhodopsin, and/or archaeorhodopsin and the agonist or stimulus comprises electromagnetic radiation. In some embodiments, the nucleic acid is administered in an AAV vector. In some embodiments, the method further comprises identifying the subject as in need of inhibiting fluid intake. In some embodiments, the subject suffers from polydipsia. In some embodiments, the method further comprises stimulating the GLP1r-positive neuron of the MnPO, in which stimulating the GLP1r-positive neuron of the MnPO comprises administering a nucleic acid encoding a stimulatory conditional ion modulator to the subject, the conditional ion modulator configured to induce a net influx of cations into and/or induce a net efflux of anions from a cytosol of the GLP1r-positive neuron in response to a stimulus or agonist. The nucleic acid can be under the control of a promoter that induces transcription of the nucleic acid in the GLP1r-positive neuron, whereby the conditional ion modulator is expressed in the GLP1r-positive neuron. The method can further comprise applying an agonist or stimulus to the neuron of the subject, causing the conditional ion modulator to induce the net influx of cations into and/or the net efflux of anions from the cytosol of the GLP1r-positive neuron. In some embodiments, the stimulatory conditional ion modulator comprises a hM3DREADD and the agonist comprises clozapine-N-oxide, or the conditional ion modulator comprises a channelrhodopsin and the agonist comprises electromagnetic radiation. In some embodiments, inhibiting the second nNOS-positive neuron of the SFO comprises administering an nNOS-specific antibody to the subject. In some embodiments, the fluid intake comprises drinking behavior.

In some embodiments, a method of monitoring thirst satiation in a subject in need thereof is described. The method can comprise detecting a level of $Ca^{2+}$ in an excitatory neuron of the lamina terminalis of the subject in real time.

BRIEF DESCRIPTION OF THE DRAWINGS

FIGS. 1A-T show that thirst driving neurons are hierarchically organized in the lamina terminalis. FIGS. 1A-C show monosynaptic connection of $SFO^{nNOS}$ with $MnPO^{nNOS}$ and $OVLT^{nNOS}$ neurons. FIG. 1A is a schematic for monosynaptic rabies tracing. Shown in FIGS. 1B-C are representative images of the median preoptic nucleus (MnPO), and the vascular organ of lamina terminalis (OVLT) of an nitric oxide synthase (nNOS)-Cre animal transduced with AAV-CA-flex-RG and AAV-EF1a-flex-TVA-mCherry (red staining seen throughout lower panel in FIG. 1B and sparser staining seen in upper panel of FIG. 1B) followed by RV-SAD-ΔG-eGFP (green staining seen throughout in FIG. 1B and in left panels of FIG. 1C). A majority of eGFP-positive neurons in the SFO overlap with nNOS-expressing neurons (magenta staining seen throughout center panels of FIG. 1C; overlay of green and red staining in right panels). FIG. 1H shows quantification of the number of licks during the 5-s session (n=9 for controls, n=7 for MnPOx, n=9 for OVLTx, n=7 for SFOx, and n=6 for SFOx/OVLTx). FIGS. 1I-K show chemogenetic inhibition of $MnPO^{nNOS}$ neurons. CNO application in brain slices inhibits firing of $MnPO^{nNOS}$ neurons (6/6 neurons). FIGS. 1P-T show that intraperitoneal NaCl injection robustly activates $SFO^{nNOS}$ neurons with (gray trace 2) or without (black trace 1) CNO injection (FIG. 1P and FIG. 1Q). In contrast, CNO injection drastically suppressed drinking behavior (FIG. 1R, n=6). Plasma osmolality (FIG. 1S) and $Na^+$ concentration (FIG. 1T) were measured after NaCl injection (n=5). Statistical significance was analysed with two-tailed Mann-Whitney U-test or paired two-tailed t-test or Kruskal-Wallis one-way ANOVA test. All error bars and shaded areas show mean±s.e.m. Scale bars, 50 μm. "1" refers to vehicle, "2" refers to CNO.

FIGS. 2A-M show that GLP1r-expressing GABAergic neurons in the MnPO are a major source of inhibitory input to the SFO. FIG. 2A shows a scheme for identifying GABAergic inputs to the SFO. Inhibitory inputs to the SFO were retrogradely labelled by HSV-hEF1α-LS1L4 mCherry (HSV-mCherry). Shown in FIG. 2B are HSV-positive neurons (staining appearing in red) in the SFO (upper panel, no red staining apparent) and MnPO (lower panel, red staining seen as isolated spots throughout the lower left) after the injection of HSV-mCherry in the SFO of Vgat-Cre (left panel) and control (right panel) animals. AAV-Syn-GCaMP6s was co-injected to visualize the injection site (green staining seen throughout, upper panel, n=4). FIG. 2C shows RNA-seq analysis of GABAergic neurons from the dorsal LT and cortex. The plot shows the ratio of gene expression levels in the LT relative to the cortex. FIGS. 2D-G show tissue staining of the MnPO from a transgenic animal expressing tdTomato (Ai9) in GLP1r neurons, with inset of FIG. 2D shown enlarged in FIGS. 2E-F. A majority (84.7±4.9%, n=3) of GAD-positive neurons (green staining apparent throughout) were marked by tdTomato (staining in red). These neurons did not overlap with glutamatergic neurons (4.3±1.3% overlap, n=3, FIG. 11A). Green and red staining was apparent throughout in FIG. 2E and FIG. 2F, respectively, corresponding with the overlay seen in FIG. 2G. FIG. 2H is a diagram showing testing for MnPO$^{GLP1r}$→SFO monosynaptic connection. Whole-cell patch-clamp recording from SFO$^{nNOS}$ or SFO$^{non-nNOS}$ neurons was performed with optogenetic stimulation of MnPO$^{GLP1r}$→SFO projections (FIG. 2I). Inhibitory synaptic currents were measured in the presence (upper trace 21) or absence (lower trace 22) of picrotoxin (PTX). Photostimulation (2 ms) was delivered at 1 Hz for 4 s, 20-30 sweeps. All SFO$^{nNOS}$ neurons tested (16/16 cells) received monosynaptic inhibitory input from MnPO$^{GLP1r}$ (top 22). By contrast, SFO$^{non-nNOS}$ neurons rarely received monosynaptic input from MnPO$^{GLP1r}$ neurons (4/15 cells, bottom), and with lower amplitude and fidelity. FIG. 2J is a diagram showing optogenetic stimulation of MnPO$^{GLP1r}$ neurons (depicted are "light off" 23 and "light on: 24). FIGS. 2K-M show that stimulation 24 of ChR2-expressing MnPO$^{GLP1r}$ neurons inhibited water-restriction (-Water) and feeding-induced (Prandial) thirst but not hunger (-Food). Water and food intake during the 10-min (for thirst) or 20-min (for hunger) sessions were quantified (n=7 for ChR2, and n=6 for control). Statistical significance was analysed with paired two-tailed t-test. All error bars show mean±s.e.m. Scale bars, 50 μm. "21" refers to patch-clamp recording in the presence of PTX, "22" refers to patch-clamp recording in the absence of PTX. "23" refers to light off. "24" refers to light on.

FIGS. 3A-I show rapid and transient activation of MnPO$^{GLP1r}$ neurons during drinking behavior. FIG. 3A shows a schematic of fiber photometry from MnPO$^{GLP1r}$ neurons. FIG. 3B shows representative real-time activity of MnPO$^{GLP1r}$ neurons in 24-h water-restricted mice (first trace from top for GCaMP6s 31 and second trace from top for eYFP 32). Corresponding lick patterns are shown (lower traces). Quantification of the responses is shown in FIG. 3C (n=6). FIGS. 3D-F show that MnPO$^{GLP1r}$ neurons respond to fluid ingestion independent of fluid composition. Representative responses of MnPO$^{GLP1r}$ neurons toward different types of liquid under water-restricted conditions: a control empty bottle, isotonic saline, silicone oil, and water. Each stimulus was presented for 30 s (shaded box). Quantification of the responses is shown in FIGS. 3E-F. Transient activation (FIG. 3E: $\Sigma\Delta F_{during}$) and baseline activity shift (FIG. 3Ft: $\Delta F_{post}$-$\Delta F_{pre}$) were quantified for MnPO$^{GLP1r}$ neurons (n=6 for saline and silicone oil, n=7 for empty and water, n=6 for all eYFP controls). In each of FIGS. 3E and 3F, the four bars on the left refer to eYFP and the four bars on the right refer to GCaMP6s. FIGS. 3G-I show internal-state-independent activation of MnPO$^{GLP1r}$ neurons. Shown are representative responses of MnPO$^{GLP1r}$ neurons to an empty bottle, peanut butter, and 300 mM sucrose under food-restricted conditions (n=6 for empty and peanut butter, n=7 for sucrose, n=6 for all eYFP controls). Statistical significance was analysed with two-tailed Mann-Whitney U-test or Kruskal-Wallis one-way ANOVA test. All error bars show mean±s.e.m. "31" refers to GCaMP6s, "32" refers to eYFP.

FIGS. 4A-S show that MnPO$^{GLP1r}$ neurons distinguish between drinking and eating behavior based on ingestive speed. FIGS. 4A-B show that MnPO$^{GLP1r}$ neurons respond to liquid water but not gel intake. Water-restricted animals were given access to water 42 or HydroGel 41. Drinking water (gray trace 42) but not eating HydroGel (black trace 41) stimulates MnPO$^{GLP1r}$ neurons (FIG. 4B). FIGS. 4C-F show quantification of the responses. The amount of water intake, the activity change (Area Under Curve), the total ingestion time, and the ingestive rate were quantified during the session (n=5). Peristimulus time histogram (PSTH) around start (FIG. 4G) and end (FIG. 4H) of water and gel intake (n=5) is shown in FIGS. 4G-J. FIGS. 4K-L show that eating solid normal chow does not stimulate MnPO$^{GLP1r}$ neurons. Food-restricted animals were given access to regular chow (dotted line), and the neural activity of MnPO$^{GLP1r}$ neurons were recorded for the following 15 min (FIG. 4K, n=5). PSTH around the start of bout (FIG. 4L, n=5). FIGS. 4M-P show that MnPO$^{GLP1r}$ neurons are sensitive to ingestive rate. 30-s water access was given to water-restricted mice in two ways; 2 s×15 times and 30 s×1 time (FIG. 4M). Each presentation was separated by 30 s intervals. The activity change, intake per minute, and the total number of licks were quantified during the 30-s water presentation (FIGS. 4N-P, n=6). FIGS. 4Q-S show that temperature has no effect on MnPO$^{GLP1r}$ activity. Shown are representative responses to ingestion of water at 4° C. (Cold 43), 25° C. (RT 44), and 37° C. (Warm 45) for the 30-s session (FIG. 4Q). Total responses (FIG. 4R) and the number of licks (FIG. 4St) were quantified (n=4). Statistical significance was analysed with two-tailed Mann-Whitney U-test or paired two-tailed t-test. All error bars and shaded areas show mean±s.e.m. "41" refers to HydroGel, "42" refers to Water, "43" refers to Cold, "44" refers to RT, and "45" refers to Warm.

FIGS. 5A-H show that inhibition of MnPO$^{GLP1r}$ neurons leads to over-drinking. FIGS. 5A-C show chemogenetic inhibition of MnPO$^{GLP1r}$ neurons. MnPO$^{GLP1r}$ neurons were infected with AAV-hSyn-DIO20 hM4Di-mCherry in GLP1r-Cre mice (FIG. 5A and FIG. 5B). CNO application inhibits firing in hM4Di-expressing MnPO$^{GLP1r}$ neurons (FIG. 5C, 6/7 neurons). FIGS. 5D-E show that CNO-induced acute inhibition of MnPO$^{GLP1r}$ neurons causes overdrinking of isotonic saline in water-restricted (-Water) animals (n=8). Drinking behavior was monitored for 30 min after the injection of CNO 52 (gray upper) or vehicle 51 (black lower, FIG. 5D). Representative lick patterns from 4 out of 8 animals are shown (FIG. 5E). The total amount of saline intake (FIG. 5F), and the time spent for drinking (FIG. 5G) were quantified (FIGS. 5F-G; black bars: vehicle 51, gray bars: CNO 52). FIG. 5H shows a schematic model summarizing thirst genesis, detection of fluid intake, and drinking-induced feedback inhibition in the LT circuit. 3V, third ventricle. GLP1r+ neurons 54 are shown on the left in the schematic of the MnPO, and nNOS+ neurons 53 are shown on the right in the schematic of the MnPO and in the SFO in FIG. 5H. Statistical significance was analysed with paired two-tailed t-test. All error bars and shaded areas show mean±s.e.m. Scale bar, 50 μm. "51" refers to vehicle, "52" refers to CNO. "53" refers to nNOS+ (excitatory) neurons, "54" refers to GLP1r+ (inhibitory) neurons in the MnPO. In the SFO, neurons shown in gray correspond to nNOS+ (excitatory) neurons.

FIGS. 6A-J show that optogenetic activation of MnPO$^{nNOS}$ and OVLT$^{nNOS}$ neurons induces robust water intake in satiated animals. FIGS. 6A-E show that water-restriction (FIGS. 6A-C) and SFO$^{nNOS}$ photostimulation (FIGS. 6D-E) induce robust c-Fos expression in the SFO, MnPO and OVLT, compared to control conditions. A majority of c-Fos signals in these areas overlapped with nNOS-expressing neurons. The graphs in FIGS. 6B and 6E show the quantification of the overlap between nNOS- and c-Fossignals (n=3). c-Fos signals in the paraventricular nucleus (PVN) and supraoptic nucleus (SON) overlapped with vasopressin (AVP)-expressing neurons (FIG. 6C). FIG. 6F shows MnPO (top) and OVLT (bottom) excitatory neurons visualized in VGlut2/Ai110 transgenic animals co-stained with nNOS (red, antibody staining seen throughout panels on the left; red staining seen throughout upper insets on the right). MnPO$^{nNOS}$ and OVLT$^{nNOS}$ neurons co-express a glutamatergic marker. 92.2±6.9% of nNOS-expressing neurons were excitatory, and 80.9±2.6% of excitatory neurons are nNOS-expressing in the MnPO (n=3). Magnified images are shown (insets, right). FIG. 6G shows a scheme for control experiments for monosynaptic rabies tracing. Shown in FIG. 6H is a representative image of the MnPO of an nNOS-Cre animal transduced with AAV-EF1a-FLEX-TVA-mCherry (top) followed by EnvA G-deleted Rabies-eGFP (bottom). No eGFP-positive cell was present in the SFO (top) FIGS. 6I-J show that photostimulation of ChR2-expressing MnPO$^{nNOS}$ and OVLT$^{nNOS}$ neurons (62 gray bars, n=8 and 4 for MnPO and OVLT respectively) triggered intense drinking; control mice infected with AAV-DIO-eYFP showed no such response (61 black bars, n=5). Photostimulated animals showed strong preference toward water over high concentration of NaCl (500 mM, right panel). Statistical significance was analysed with two-tailed Mann-Whitney U-test. All error bars show mean±s.e.m. Scale bars, 50 µm. "61" refers to eYFP, "62" refers to ChR2.

FIGS. 7A-T show that MnPO$^{nNOS}$ neurons are necessary for the induction of drinking by SFO$^{nNOS}$ photostimulation. FIGS. 7A-B show that Casp3-TEVp efficiently eliminates SFO$^{nNOS}$ (FIG. 7B) neurons without affecting MnPO$^{nNOS}$ (FIG. 7A) neurons. c-Fos expression pattern is shown after water-restriction (red staining seen throughout in FIG. 7A; faint red staining seen throughout in FIG. 7B). Shown in FIGS. 7C-F are rastor plots representing licking events during the 5-s session with photostimulation. FIGS. 7G-H show that ablation of MnPO$^{nNOS}$ (MnPOx) 72 but not SFO$^{nNOS}$ (SFOx) 73 neurons attenuated the drinking response to OVLT$^{nNOS}$ photostimulation (FIG. 7G, 10 minutes, gray box). Quantification of the number of licks during the 10-minute light on period (FIG. 7H, n=9 for controls and MnPOx and n=7 for SFOx). "71" refers to OVLT$^{nNOS}$ photostimulation (OVLT stim), "72" refers to ablation of MnPO$^{nNOS}$ neurons (MnPOx), "73" refers to ablation of SFO$^{nNOS}$ neurons (SFOx). FIGS. 7I-K show 5-s brief access assays to examine the necessity of MnPO$^{nNOS}$ neurons. Acute inhibition of MnPO$^{nNOS}$ neurons by CNO injection severely reduced SFO$^{nNOS}$-stimulated (FIG. 7I, n=5 for CNO, n=3 for vehicle, and n=6 for no i.p.) and dehydration-induced water intake (FIG. 7J, n=7 for CNO, n=5 for vehicle, and n=3 for no i.p.). But the same treatment did not suppress sucrose consumption (300 mM, FIG. 7Kt, n=6 for CNO, n=5 for vehicle, and n=3 for no i.p.). Control animals transduced by AAV-DIO-mCherry in the MnPO showed no reduction after water or food-restriction (n=3). FIGS. 7L-N show an mCherry control for FIGS. 1L-N. Cumulative water intake in nNOS-Cre animals transduced with AAV-DIO-mCherry in the MnPO, AAV-DIO-ChR2-eYFP in the SFO under photostimulated (FIG. 7M, n=5) or water-restricted conditions (FIG. 7N, n=5), and sucrose (300 mM) intake under food-restricted conditions (FIG. 7O, n=5). "74" refers to vehicle, "75" refers to CNO. FIGS. 7P-T show that intraperitoneal Mannitol injection robustly activated SFO$^{nNOS}$ neurons with (gray trace 75) or without (black trace 74) CNO injection (FIG. 7P). CNO injection drastically suppressed drinking behavior without changing the activity of SFO$^{nNOS}$ neurons (FIGS. 7Q-R, n=4). Plasma osmolality, but not Na+ concentration was increased by Mannitol injection (FIGS. 7S-T, n=5). Statistical significance was analysed with paired two-tailed t-test or Kruskal-Wallis one-way ANOVA test. All error bars and shaded areas show mean±s.e.m. Scale bar, 50 µm.

FIGS. 8A-D show that the SFO receives sparse monosynaptic input from MnPO$^{nNOS}$ neurons. FIG. 8A shows a diagram for testing MnPO$^{nNOS}$→SFO monosynaptic connection. Whole-cell patch-clamp recording from SFO neurons was performed with optogenetic stimulation of MnPO$^{nNOS}$→SFO projections (FIGS. 8B-C). Excitatory synaptic currents were measured in the presence (upper gray trace 82, FIG. 8C) or absence (lower black trace 81) of CNQX (10 µM)+DL-APV (25 µM) after photostimulation (2 ms, arrowheads). Most SFO$^{nNOS}$ neurons (12/16 cells, labeled with mCherry, FIG. 8B) or SFO$^{non-nNOS}$ neurons (14/16 cells) did not receive monosynaptic input from MnPO$^{nNOS}$ neurons (FIG. 8C). FIG. 8D shows that photostimulation of ChR2-expressing MnPO$^{nNOS}$ neurons (staining shown in upper left and center panels) induced robust c-Fos expression in the MnPO (staining shown in upper left and right panels) but not in the SFO (bottom). Scale bar, 50 µm. "81" refers to measurement of synaptic currents in the absence of CNQX+DL-APV. "82" refers to measurement of synaptic currents in the presence of CNQX+DL-APV (+CNQX/APV).

FIGS. 9A-F show neural dynamics of SFO$^{nNOS}$ and MnPO$^{nNOS}$ neurons. FIGS. 9A-B show schematics of fiber photometry from SFO$^{nNOS}$ (FIG. 9A) and MnPO$^{nNOS}$ (FIG. 9B) neurons. nNOS-Cre mice were injected with AAV-DIO-GCaMP6s or eYFP into the SFO and MnPO. FIG. 9C depicts representative traces showing the real-time activity of the SFO$^{nNOS}$ (second trace from top, 92) and MnPO$^{nNOS}$ (sixth trace from top, 96) populations with water intake in water-restricted mice. First 91 and fifth 95 traces from top show the activity of eYFP control animals. Corresponding lick patterns of AAV-DIO-GCaMP6s-injected animals (third 93 and seventh 97 traces) and eYFP-injected animals (fourth 94 and eighth 98 traces) are shown. Consistent with recent studies[8],[38], SFO$^{nNOS}$ and MnPO$^{nNOS}$ neurons are rapidly and persistently inhibited by water drinking. FIGS. 9D-F show that SFO$^{nNOS}$ and MnPO$^{nNOS}$ neurons are sensitive to thirst-inducing stimuli. FIG. 9D shows that intraperitoneal injection of NaCl (2 M, 300 µl) in a water-satiated animal robustly activated SFO$^{nNOS}$ (upper trace) and MnPO$^{nNOS}$ (lower trace) neurons. Quantification of the responses is shown in FIGS. 9E-F. During liquid intake 99 (black bars, n=4 for SFO, n=6 for MnPO) and sodium loading 90 (gray bars, n=5), both SFO$^{nNOS}$ and MnPO$^{nNOS}$ neurons showed opposite activity changes. All error bars show mean±s.e.m. "91" and "95" refer to traces for eYFP control animals following injection into the SFO or MnPO, respectively; "92" and 96" refer to traces for animals injected with AAV-DIO-GCaMP6s in the SFO or MnPO, respectively; "94" and "98" refer to lick patterns for eYFP control animals following injection into the SFO or MnPO, respectively; "93" and "97" refer to lick patterns for animals injected with AAV-DIO-GCaMP6s in the SFO or MnPO, respectively.

FIGS. 10A-K show mapping of inhibitory inputs to the SFO. FIG. 10A shows a schematic for retrograde tracing of inhibitory inputs to the SFO by HSV-mCherry. Shown are the major inhibitory inputs to the SFO (FIGS. 10B-G). FIG. 10H shows quantification of HSV-positive neurons (n=4). LS, Lateral Septum; MS, Medial Septum; BNST, Bed Nucleus of the Stria Terminalis; MPA, Medial Preoptic Area; and OVLT, Vascular Organ of the Lamina Terminalis. FIGS. 10I-K show mMonosynaptic retrograde rabies tracing of SFO$^{nNOS}$ neurons. Shown are representative images of the SFO of an nNOS-Cre animal transduced with AAV-CA-FLEX-RG and AAV10 EF1a-FLEX-TVA-mCherry followed by EnvA G-deleted Rabies-eGFP (FIGS. 10I-J, left). Practically no eGFP-positive neurons in the MnPO (staining seen in upper left and right and lower left and right panels, 5.5±2.2%, n=4) overlapped with excitatory nNOS-expressing neurons (staining seen in upper center and right and lower center and right panels). FIG. 10K shows that maximum inputs to the SFO$^{nNOS}$ neurons are from the MnPO, followed by MS, LS, MPA and OVLT. (n=4). All error bars show mean±s.e.m. Scale bars, 50 μm.

FIGS. 11A-K show that the MnPO$^{GLP1r}$ population does not overlap with nNOS-expressing neurons. FIG. 11A shows nNOS antibody staining (inset staining on bottom right) of the MnPO from a GLP1r- Cre/Ai9 transgenic animal expressing tdTomato in MnPO$^{GLP1r}$ neurons (inset staining on top right). No significant overlap was observed between these populations (inset overlay on far right; 4.3±1.3% of GLP1r19 expressing neurons, n=3). nNOS antibody staining in green and tdTomato staining in red was seen throughout the left panel in FIG. 11A. FIG. 11B shows fluorescence in situ hybridization (FISH), demonstrating that a majority of Ai9 expression (left, 91.9±4.8%, n=3) faithfully overlaps with endogenous GLP1r expression (center). Image overlay shown on the right. FIG. 11C shows a diagram showing optogenetic stimulation of MnPO$^{GLP1r}$ neurons transduced with AAV-DIO-ChR2-eYFP or AAV-DIO-eYFP. FIGS. 11D-E show that stimulation of ChR2-expressing MnPO$^{GLP1r}$ neurons 112 inhibited drinking after water-restriction as compared to eYFP controls 111. (n=7 for ChR2, n=6 for controls, gray box indicates the Light-ON period). Quantified data are shown (FIG. 11E). For statistical analysis, we used the same data set for 0-10 min from FIGS. 2J-M. FIGS. 11F-H show that GLP1 has minor effects on acute drinking behavior. FIG. 11F shows a diagram of whole-cell recording from MnPO$^{GLP1r}$ neurons. A GLP1 agonist, Exendin-4 (Ex-4), had no effect on the firing frequency of MnPO$^{GLP1r}$ neurons in brain slice preparation (FIG. 11G). However, there was a small decrease in the resting membrane potential (FIG. 11H). FIG. 11I shows ELISA analysis of plasma GLP1 level. Feeding behavior induced robust plasma GLP1 secretion whereas water intake did not (n=5 for WD+W and FD, n=6 for control and WD, and n=7 for FD+F). FIG. 11J shows that intra-cranial injection of Ex-4 (lower trace 115, n=7) into the MnPO had no effect on water intake after water deprivation as compared to vehicle injection (ACSF, upper trace 116, n=7). FIG. 11K shows a representative injection pattern visualized with fluorescent Ex-4 FAM. Green staining was seen throughout the lower third of the image. Statistical significance was analysed with two-tailed Mann-Whitney U-test or paired t-test or Kruskal-Wallis one-way ANOVA test. All error bars show mean±s.e.m. Scale bars, 50 μm. "111" refers to eYFP, "112" refers to ChR2; "116" refers to vehicle, "115" refers to Exendin-4 (Ex-4).

FIGS. 12A-D show that SFO$^{nNOS}$ neurons are negatively and chronically regulated by water drinking. Representative responses of SFO$^{nNOS}$ to different types of liquids under water-restricted conditions: a control empty bottle, isotonic saline, silicone oil, and water (FIG. 12A). Each stimulus was presented for 30 s (shaded box). Quantification of the responses is shown in FIGS. 12B-C. Activity change (FIG. 12B: Area Under Curve) and baseline activity shift (FIG. 12C: ΔF change) were quantified for SFO$^{nNOS}$ (GCaMP6s, first to fourth bar from left; control, fifth to eighth bar from left) neurons. A significant shift in the baseline activity (ΔF change) was observed only in response to water ingestion. (n=6 for saline, n=7 for empty, silicone oil and water, n=5 for eYFP). FIGS. 12D-F show representative responses of SFO$^{nNOS}$ neurons to an empty bottle, peanut butter, and 300 mM sucrose solution under food-restricted conditions (n=7 for empty and peanut butter, n=5 for sucrose, n=5 for eYFP recordings).

FIGS. 13A-L show that acute inhibition or chronic ablation of MnPO$^{GLP1r}$ neurons causes overdrinking. FIGS. 13A-D show that acute inhibition of hM4Di-expressing MnPO$^{GLP1r}$ neurons by CNO significantly increases water consumption at the onset of drinking. Drinking behavior was monitored for 30 min after the injection of CNO (FIGS. 13A-B). Magnified data (0-1 min) is shown (FIGS. 13C-D). Although CNO-injected animals drank a similar total amount of water as the control group during the 30-min session (FIGS. 13A-B), they consumed significantly larger fraction of water during the first 1 min (FIGS. 13C-D, n=8). FIGS. 13 E-H, mCherry controls for acute inhibition of MnPO$^{GLP1r}$ neurons. Drinking behavior was monitored for 30 min after the injection of CNO/vehicle under water deprived conditions with ad lib access to saline (FIGS. 13E-F) or water (FIGS. 13G-H). No significant difference was found between animals injected with CNO and vehicle (n=6). FIG. 13I shows a schematic for genetic ablation of MnPO$^{GLP1r}$ neurons with AAV-flex-Casp3-TEVp in GLP1r-Cre/Ai9 mice. Compared to a control animal (FIG. 13K), a Casp3-injected animal exhibited almost no GLP1r-expressing neurons in the MnPO (FIG. 13J). In both cases, GLP1r-expressing neurons were labeled using GLP1r-Cre/Ai9 transgenic animals. FIG. 13L shows that genetic ablation of MnPO$^{GLP1r}$ neurons (upper trace, n=4) recapitulates overdrinking phenotype similar to the acute inhibition by hM4Di (FIGS. 5D-E) compared to control eYFP group (lower trace, n=6). Statistical significance was analysed with paired two-tailed t-test or two-tailed Mann-Whitney U-test. All error bars and shaded areas show mean±s.e.m. Scale bar, 50 μm.

"131" refers to vehicle, "132" refers to CNO; "133" refers to eYFP, and "134" refers to Casp3.

Figures 13L, 14A:
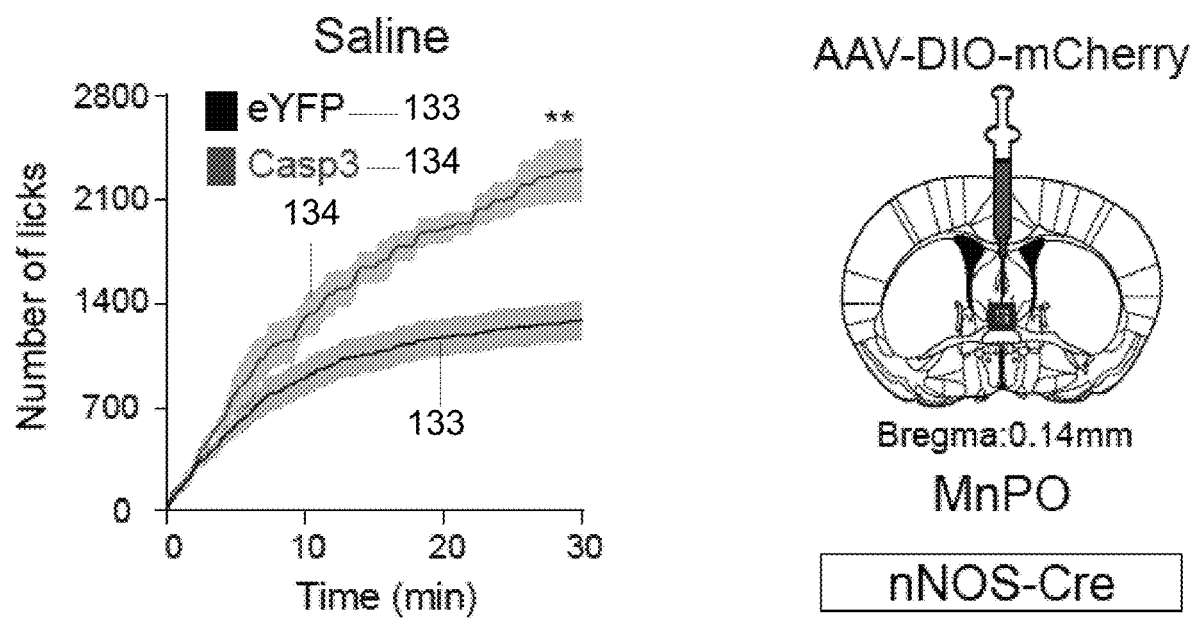
Figure 14J:
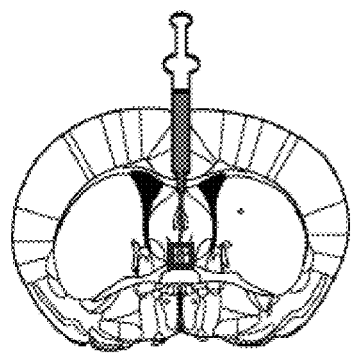
Figure 14J:
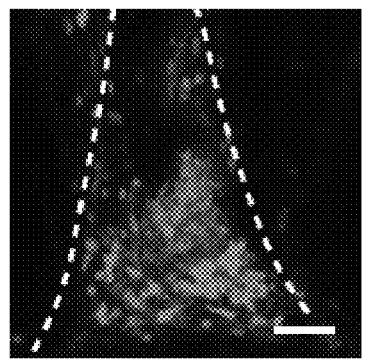
Figures 14S, 14T, 14U:
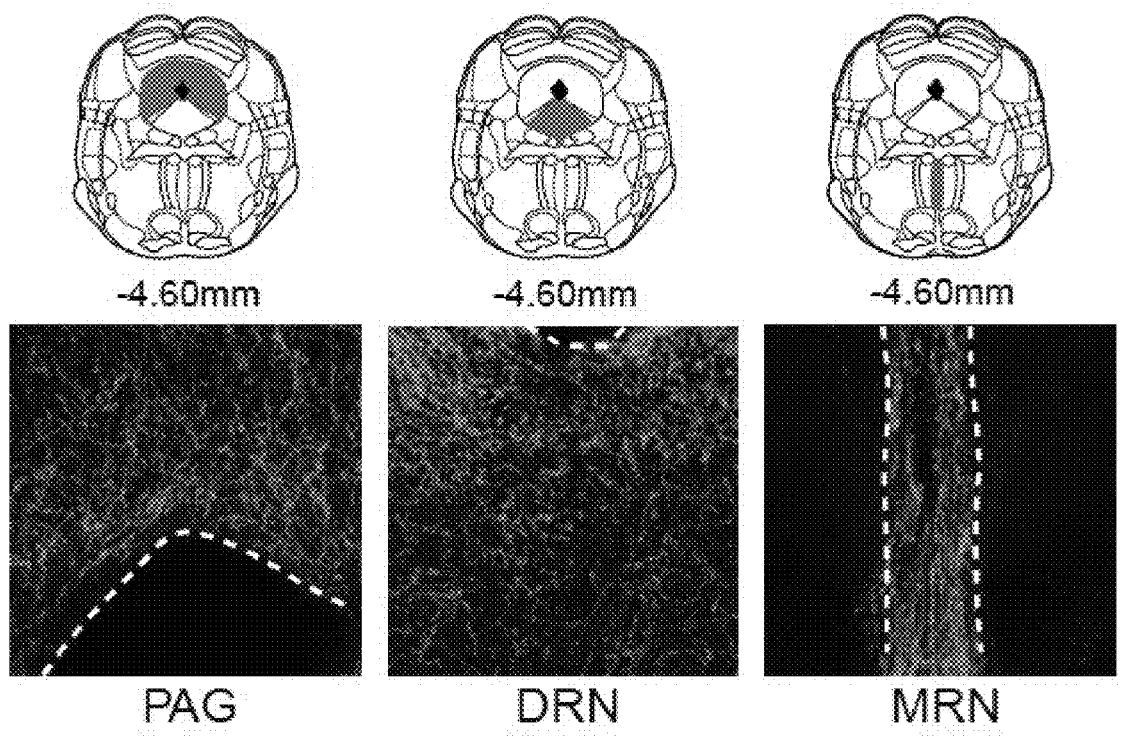

FIGS. 14A-U show neural projections from nNOS- and GLP1r-positive MnPO neurons. Schematics for mapping out downstream targets of MnPO neurons by AAV-DIO-mCherry/eYFP (FIG. 14A and FIG. 14J). Shown are the major outputs from MnPO neurons. nNOS-Cre (FIGS. 14A-I) and GLP1r-Cre mice (FIGS. 14 J-U) were injected with AAV-DIO-mCherry and AAV-DIO20 eYFP in the MnPO respectively, and the axon projections were examined using reporter expression. Shown are the injection sites (FIG. 14A and FIG. 14J) and representative downstream targets (1/3 animals). OVLT, Vascular Organ of Lamina Terminalis; PVT, Paraventricular Thalamic Nucleus; SON, Supraoptic Nucleus; PVH, Paraventricular Hypothalamic Nucleus; Arc, Arcuate Nucleus; DMH, Dorsomedial Hypothalamic Nucleus; LH, Lateral Hypothalamus; PAG, Periaqueductal Gray; SFO, Subfornical Organ; DRN, Dorsal Raphe Nucleus; MRN, Median Raphe Nucleus. Scale bars, 50 μm.

DETAILED DESCRIPTION

The lamina terminalis (LT) comprises three anatomically interconnected main nuclei that sense and regulate internal water balance, the subfornical organ (SFO), the median preoptic nucleus (MnPO), and the vascular organ of lamina terminalis (OVLT). It has been observed herein that neural populations in the LT drive fluid intake, and that fluid intake can be stimulated or inhibited by modulating these neural populations. For example, nitric oxide synthase (nNOS)-positive neurons in the MnPO assimilate signals, and stimulate fluid intake (drinking behavior) when active. On the other hand inhibiting nNOS-positive neurons of the MnPO inhibits fluid intake (drinking behavior)(See Examples 1 and 5). nNOS-neurons in the SFO stimulate nNOS-positive neurons in the MnPO (See Example 1). Additionally, glucagon-like peptide 1 receptor (GLP1r)-positive neurons in the MnPO inhibit nNOS-positive neurons in the SFO (See FIG. 5H). Accordingly, in some embodiments methods of stimulating fluid intake are described. The methods can comprise stimulating nNOS-positive neurons in the MnPO, for example directly, and/or by stimulating nNOS-positive neurons in the SFO, and/or by inhibiting GLP1r-positive neurons in the MnPO in a subject. These methods can be applied to subjects in need of stimulating thirst or fluid intake, such as subjects suffering from dehydration, adipsia, hypodipsia, and/or kidney disease or damage or disorder or dysfunction (such as kidney stones) and/or elderly subjects. In some embodiments, the subjects suffer from dehydration, adipsia, and/or hypodipsia. In some embodiments, methods of inhibiting fluid intake are described. The methods can comprise inhibiting nNOS-positive neurons in the MnPO directly, and/or inhibiting nNOS-positive neurons in the SFO, and/or stimulating GLP1r-positive neurons in the MnPO in a subject. These methods can be applied to subjects in need of inhibiting thirst or fluid intake, such as subjects suffering from polydipsia.

Experimental methods and examples as described herein are by way of illustration and not limitation.

As used herein, the terms "inhibiting" a neuron (for example, an nNOS-positive and/or GLP1r-positive neuron as described herein) has its customary and ordinary meaning as would be understood by one of ordinary skill in the art in view of this disclosure. It refers to reducing the likelihood of, delaying the onset of, and/or preventing depolarization of the cell membrane of the neuron (which may also be referred to as the plasma membrane), and thus, reducing the likelihood of, delaying the onset of, and/or preventing the neuron from generating an action potential or firing. As such, in some embodiments, an inhibited neuron may not induce an action potential or fire. For example, a neuron can be inhibited by inducing a net efflux of cations from the cytosol and/or by inhibiting, reducing the likelihood of, or preventing a net influx of cations into the cytosol. For example, a neuron can be inhibited by inducing, increasing the likelihood of, or stimulating a net influx of anions into the cytosol. By way of example, a net efflux of cations may comprise cations leaving the cytosol through a channel or pump in the plasma membrane or the endoplasmic reticulum (ER). By way of example, a net influx of anions may comprise anions entering the cytosol across the plasma membrane. Example cations include protons ($H^+$), potassium ($K^+$), calcium ($Ca^{2+}$), or a combination of these. Example anions include chloride anions ($Cl^-$). If additional numerical precision is of interest, in some embodiments, a neuron is inhibited when the likelihood of an action potential (compared to an unaltered neuron over a specified period of time, for example, 0.01, 0.1, 1, or 10 seconds) is reduced by at least 50%, 60%, 70%, 80%, 90%, 95%, or 99%. It will be appreciated that in some embodiments, inhibiting a neuron silences that neuron.

As used herein, "stimulating" a neuron (for example, an nNOS-positive and/or GLP1r-positive neuron as described herein) has its customary and ordinary meaning as would be understood by one of ordinary skill in the art in view of this disclosure. It refers to increasing the likelihood of, expediting the onset of, and/or inducing depolarization of the cell membrane of the neuron, and thus, increasing the likelihood of, expediting the onset of, and/or inducing an action potential in the neuron. For example, a neuron can be stimulated by a net efflux of anions from the cytosol, and/or a net influx of cations to the cytosol. As such, in some embodiments, a stimulated neuron may be depolarized, inducing an action potential or firing of the neuron. Depolarization may be the result of a net influx of cations into the cytosol of the neuron. Cations may enter the cytosol though a channel in the plasma membrane and/or ER. The cations may comprise, consist essentially of, or consist of protons ($H^+$), sodium cations ($Na^+$) and/or calcium ($Ca^{2+}$) ions, or a combination of these. If additional numerical precision is of interest, in some embodiments, a neuron is stimulated when the likelihood of an action potential (compared to an unaltered neuron over a specified period of time, for example 0.01, 0.1, or 1 second) is increased by at least 50%, 60%, 70%, 80%, 90%, 95%, or 99%. It will be appreciated that in some embodiments, stimulating a neuron activates that neuron.

Neural Thirst Circuits

Without being limited by theory, the lamina terminalis (LT) is the main brain structure responsible for sensing and regulating internal water balance[12],[15]-[17]. It contains three main nuclei, the SFO, MnPO, and vascular organ of lamina terminalis (OVLT) that are anatomically interconnected. The murine MnPO and SFO are contemplated to have corresponding structures in the lamina terminalis of the human brain. Accordingly, it will be understood that as used herein "MnPO" and "SFO" each refers to a structure in the lamina terminalis, and further that structures of the human as well as murine lamina terminalis are contemplated in conjunction with methods and compositions of some embodiments. For example, MnPO is contemplated to refer to the murine MnPO, and also refer to structures in the human lamina terminalis corresponding to the murine MnPO. For example, "SFO" is contemplated to refer to the murine SFO, and also structures in the human lamina terminalis corresponding to the murine SFO. For the avoidance of doubt, in the context of particular working examples herein, reference to the MnPO and/or SFO of a particular organism used in an experiment (for example, mouse) will refer to that organism. However, the experimental results are contemplated to applicable to corresponding lamina terminalis structures of other organisms (for example, humans).

Figure 5C:
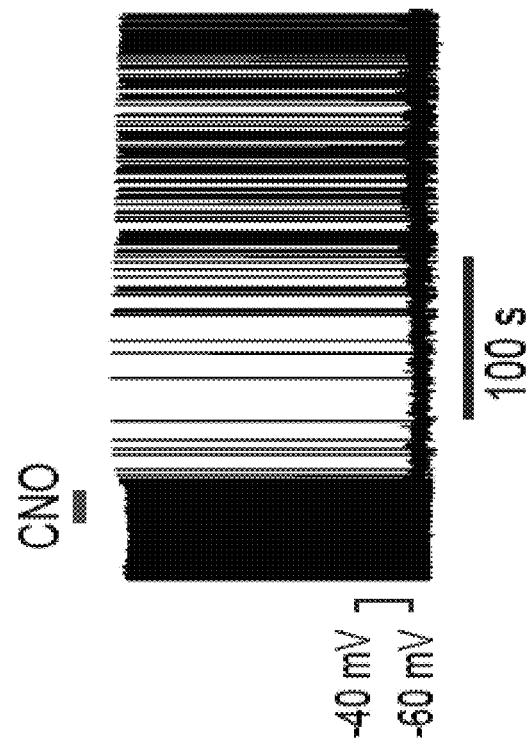
Figure 5B:
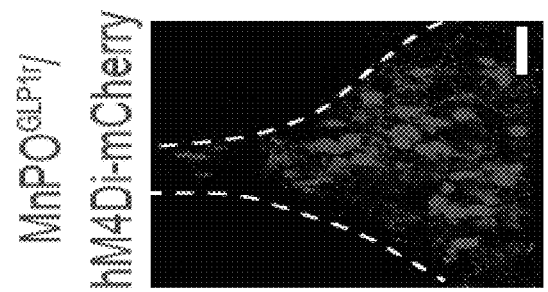
Figure 5A:
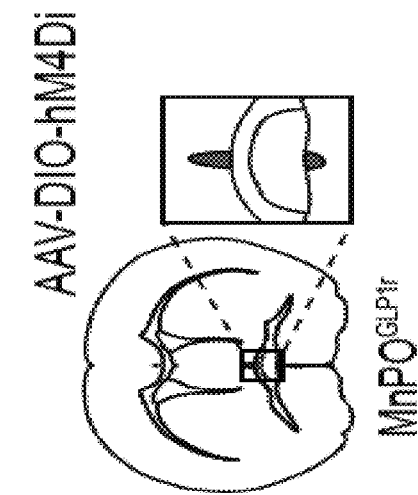
Figure 5H:
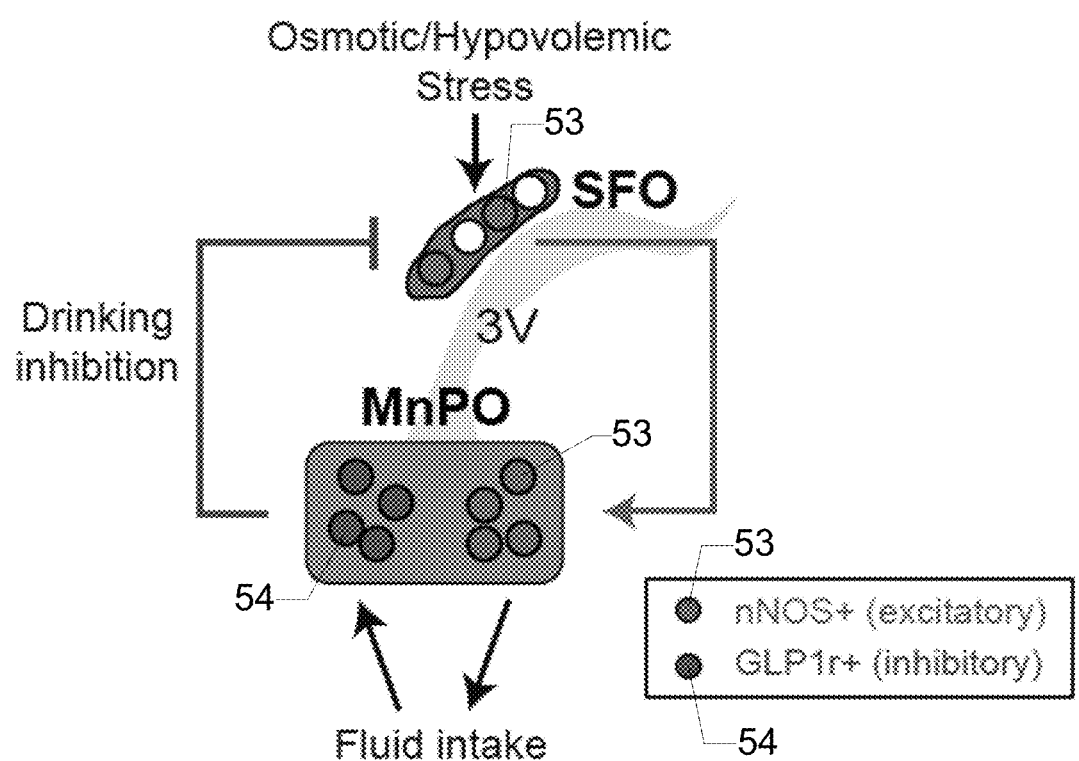

Specific neural populations in the LT have a causal role in regulating drinking behavior and fluid intake. Neurons involved in neural thirst circuits include excitatory neurons in the MnPO and SFO, such as nitric oxide synthase nNOS-positive neurons, and inhibitory neurons in the MnPO such as GLP1r-positive neurons. A schematic neural thirst circuit is illustrated in FIG. 5H. In accordance with some embodiments herein, optogenetic and/or chemogenetic activation of excitatory SFO neurons expressing nNOS (SFO$^{nNOS}$ neurons) drives immediate and robust drinking behavior.

For example in methods and compositions of some embodiments, fluid intake (e.g., drinking behavior) can be induced by any of stimulating nNOS-positive neurons of the MnPO, stimulating nNOS-positive neurons of the SFO, and/or inhibiting GLP1r-positive neurons of the MnPO. In some embodiments, fluid intake (e.g., drinking behavior) is induced by stimulating nNOS-positive neurons of the MnPO and stimulating nNOS-positive neurons of the SFO (See, e.g., Example 1). In some embodiments, fluid intake (e.g., drinking behavior) is induced by stimulating nNOS-positive neurons of the MnPO and inhibiting GLP1r-positive neurons of the MnPO. (See, e.g., Example 5). In some embodiments, fluid intake (e.g., drinking behavior) is induced by stimulating nNOS-positive neurons of the SFO and inhibiting GLP1r-positive neurons of the MnPO. (See, e.g., Examples 1 and 5).

For example, in methods and compositions of some embodiments, fluid intake (e.g., drinking behavior) can be inhibited by any of inhibiting nNOS-positive neurons of the MnPO, inhibiting nNOS-positive neurons of the SFO and/or activating GLP1r-positive neurons of the MnPO, and/or activating GLP1r-positive neurons of the SFO. In some embodiments, fluid intake (e.g., drinking behavior) is inhibited by inhibiting nNOS-positive neurons of the MnPO and inhibiting nNOS-positive neurons of the SFO (See, e.g., Example 1). In some embodiments, fluid intake (e.g., drinking behavior) is inhibited by inhibiting nNOS-positive neurons of the MnPO and activating GLP1r-positive neurons of the MnPO. (See, e.g., Example 1). In some embodiments, fluid intake (e.g., drinking behavior) is inhibited by inhibiting nNOS-positive neurons of the SFO and activating GLP1r-positive neurons of the MnPO.

Nitric oxide synthase (nNOS)-Positive Neurons in the Median Preoptic Nucleus (MnPO)

Multiple excitatory neural populations in the lamina terminalis form an interconnected and hierarchical circuit architecture to mediate drinking behavior. Among these populations, nitric oxide synthase (nNOS)-positive neurons in the median preoptic nucleus (MnPO) integrate signals from thirst-driving neurons of the subfornical organ (SFO) to coordinate drinking. nNOS-positive neurons may be referred to as "nNOS+neurons" or "nNOS neurons." Inhibiting (e.g., silencing) nNOS-positive neurons in the MnPO abolishes water intake in thirsty animals without impairing the osmosensory function of SFO neurons (See Example 1). By contrast, activating or stimulating nNOS-positive neurons of the MnPO induces water intake (See Example 1).

In accordance with methods and compositions of some embodiments, stimulating fluid intake comprises stimulating an excitatory neuron of the MnPO such as a nNOS-positive neuron of the MnPO (for example, by stimulating depolarization of the cell membrane of the nNOS-positive neuron of the MnPO). In accordance with methods and compositions of some embodiments stimulating fluid intake comprises stimulating an excitatory neuron of the SFO such as a nNOS-positive neuron of the SFO (for example, by stimulating depolarization of the cell membrane of the nNOS-positive neuron of the SFO). The nNOS positive-neuron of the SFO can synapse with the nNOS-positive neuron of the MnPO. In accordance with methods and compositions of some embodiments, inhibiting of fluid intake comprises stimulating an inhibitory neuron of the MnPO such as a GLP1r-positive neuron of the MnPO (for example, by increasing in the quantity of cations in the cytosol). The stimulation of any of the neurons described herein can comprise, consist essentially of, or consist of depolarization of the neuron, a net influx of cations into the cytosol (such as transmembrane migration of sodium cations into the cytosol and/or a release of calcium ions from an endoplasmic reticulum into the cytosol). In some embodiments, a population of neurons is stimulated, for example at least 10, $10^2$, $10^3$, $10^4$, $10^5$, $10^6$ or $10^7$ neurons, including ranges between any two of the listed values, for example $10\text{-}10^4$, $10\text{-}10^7$, $10^3\text{-}10^4$, $10^3\text{-}10^6$, or $10^3\text{-}10^7$.

In accordance with methods and compositions of some embodiments inhibiting fluid intake comprises inhibiting an nNOS-positive neuron of the MnPO (for example, by inhibiting or preventing depolarization of the cell membrane of the nNOS-positive neuron of the MnPO). In accordance with methods and compositions of some embodiments, inhibiting fluid intake comprises inhibiting an nNOS-positive neuron of the SFO (for example, by inhibiting or preventing depolarization of the cell membrane of the nNOS-positive neuron of the SFO). In accordance with methods and compositions of some embodiments, stimulating fluid intake comprises inhibiting a GLP1r-positive neuron of the MnPO (for example, by inhibiting or preventing depolarization of the cell membrane of the GLP1r-positive neuron of the MnPO). The inhibition of any of the neurons described herein can comprise, consist essentially of, or consist of hyperpolarization of the neuron; removal of cations (such as protons, potassium and/or calcium ions) from the cytosol of the neuron; entry of anions (such as chloride ions) into the cytosol of the neuron; and/or inhibition of the release of calcium ions from an ER to the cytosol. In some embodiments, a population of neurons is inhibited, for example at least 10, $10^2$, $10^3$, $10^4$, $10^5$, $10^6$ or $10^7$ neurons, including ranges between any two of the listed values, for example $10\text{-}10^4$, $10\text{-}10^7$, $10^3\text{-}10^4$, $10^3\text{-}10^6$, or $10^3\text{-}10^7$.

GLP1r-Positive Neurons in the MnPO

As described herein, a distinct inhibitory circuit encodes drinking-induced rapid thirst alleviation. Specific inhibitory neurons in the MnPO that are positive for or express glucagon-like peptide 1 receptor (GLP1r) are activated immediately upon drinking behavior. For conciseness, these neurons may be referred to herein as "GLP1r-positive neurons," "GLP1r+ neurons," or "GLP1r neurons." The inhibitory responses to GLP1r-positive neurons are not specific for water only, but can be induced by liquid ingestion (e.g., drinking behavior), and can be time-locked to the onset and offset of drinking. It is reported herein that the inhibitory GLP1r-positive neuronal population typically suppresses thirst-driving SFO neurons through a monosynaptic connection (See Example 2). Furthermore, acute and chronic loss-of-function manipulations of GLP1r-positive MnPO neurons can lead to a polydipsic over-drinking phenotype (See, e.g., Example 5). Thus, GLP1r-positive neurons of the MnPO facilitate satiety of thirst by monitoring real-time fluid ingestion (e.g., drinking action). In accordance with methods and compositions of some embodiments, inhibiting GLP1r-positive neurons of the MnPO increases fluid intake, for example fluids comprising, consisting essentially of, or consisting of water. In accordance with methods and compositions of some embodiments, activating or stimulating GLP1r-positive neurons of the MnPO inhibits fluid intake, for example fluids comprising, consisting essentially of, or consisting of water. In accordance with methods and compositions of some embodiments, activating or stimulating GLP1r-positive neurons of the MnPO inhibits fluid intake, for example fluids comprising, consisting essentially of, or consisting of water.

Subjects

The methods and compositions described in accordance with embodiments herein are applicable to a variety of subjects, including, but not limited to human subjects and non-human subjects such as non-human mammals. In some embodiments, the subject is an elderly subject. By way of example, in accordance with methods and compositions of embodiments herein, an "elderly" subject can refer to a human that is at least 50 years old, for example at least 55, 60, 65, 70, 75, or 80 years old, including ranges between any two of the listed values, for example 50-70, 50-80, 60-70, 60-80, or 70-80 years old. In some embodiments, a subject suffers from at least one of dehydration, adipsia, hypodipsia, or polydipsia. In some embodiments, a subject suffers from at least one of dehydration, adipsia, hypodipsia, and/or kidney disease, disorder, damage or dysfunction (such as kidney stones). It is contemplated that a subject suffering from dehydration, adipsia, hypodipsia, and/or kidney disease, disorder, damage or dysfunction will benefit from stimulating fluid intake. By way of example, in methods of some embodiments, fluid intake can be increased compared to fluid intake before application of the methods described herein. In some embodiments, a subject suffers from polydipsia. It is further contemplated that a subject suffering from polydipsia will benefit from inhibiting fluid intake. By way of example, in methods of some embodiments, fluid intake is inhibited compared to fluid intake before application of the methods.

In accordance with methods and compositions of embodiments herein, fluid intake can comprise, consist essentially of, or consist of drinking behavior. In some embodiments, a fluid that is taken in comprises, consists essentially of, or consists of water.

Conditional Ion Modulators

As used herein, "chemogenetic receptor" has its customary and ordinary meaning as would be understood by one of ordinary skill in the art in view of this disclosure. It refers to a receptor that can be expressed in a cell, and modulates movement of ions in or out of the cell when a condition is present, for example binding of an agonist such as a small molecule such as CNO. For example, the chemogenetic receptor can comprise a G protein coupled receptor, and can conditionally induce signaling in the cell that expresses the receptor. By way of example, Designer Receptors Exclusively Activated by Designer Drugs (DREADDs) are examples of chemogenetic receptors. Examples of chemogenetic receptors are reviewed in Roth (2016), "DREADDs for Neuroscientists" Neuron. 89: 683-694, which is incorporated by reference in its entirety herein. For example, the chemogenetic receptor can comprise an ion channel or ion pump, or be in signal transduction communication with an ion channel or ion pump. It will be understood that a "chemogenetic receptor nucleic acid" refers to a nucleic acid that encodes a chemogenetic receptor. In some embodiments, the optogenetic actuator comprises, consists essentially of, or consists of hM3DREADD or hM4Di.

As used herein, "optogenetic actuator" has its customary and ordinary meaning as would be understood by one of ordinary skill in the art in view of this disclosure. It refers to an ion transporter that can be expressed in a cell, and directly or indirectly transport ions (into or out of the cytosol) when a condition is present, for example upon stimulation with electromagnetic radiation. As used herein, an optogenetic actuator encompasses both passive transporters (such as ion channels), and active transporters (such as ion pumps). For example, the optogenetic actuator can comprise an ion channel or ion pump, and can conditionally permit or prevent the passage of ions through the ion channel. In some embodiments, the optogenetic actuator comprises, consists essentially of, or consists of channelrhodopsin, halorhodopsin, and/or archaeorhodopsin. Examples of optogenetic actuators are reviewed in Lin (2011) "A User's Guide to Channelrhodopsin Variants: Features, Limitations and Future Developments" Exp. Physiol. 96: 19-25, which is incorporated by reference in its entirety herein. It will be understood that a "optogenetic actuator nucleic acid" refers to a nucleic acid that encodes a optogenetic actuator. In some embodiments, the optogenetic actuator comprises, consists essentially of, or consists of channelrhodopsin, halorhodopsin, and/or archaeorhodopsin.

For conciseness, "conditional ion modulator" as used herein refers to chemogenetic receptors and optogenetic actuators. In some embodiments, the conditional ion modulator comprises, consists essentially of, or consists of a chemogenetic receptor or an optogenetic actuator. In some embodiments, the conditional ion modulator comprises, consists essentially of, or consists of a chemogenetic receptor. In some embodiments, the conditional ion modulator comprises, consists essentially of, or consists of an optogenetic actuator. It will be understood that a "conditional ion modulator nucleic acid" refers to a nucleic acid that encodes a conditional ion modulator (e.g., an optogenetic receptor or chemogenetic receptor).

In some embodiments, the conditional ion modulator comprises a chemogenetic receptor such as a Designer Receptor Exclusively Activated by Designer Drugs (DREADD). The DREADD may encode a receptor such as a G protein coupled receptor configured to depolarize or activate a neuron. An example DREADD is hM3DREADD, which comprises a modified human M3 muscarinic receptor, and is activated by the agonist clozapine-N-oxide (CNO). The CNO can be administered to a subject, for example systemically or directly to the CNS, and can thus bind to the chemogenetic receptor (such as hM3DREADD). Binding of CNO to hM3DREADD induces Gq G-protein coupled signaling, which induces the release of intracellular calcium in neurons, enhancing neuron activation. In some embodiments, CNO is administered nasally, transcranially, or intracranially. In some embodiments, CNO is administered orally, intravenously, subcutaneously, transdermally, intreperitoneally, or nasally.

In some embodiments, the conditional ion modulator comprises an optogenetic actuator such as a channelrhodopsin (e.g., ChR2 or VChR1). Channelrhodopsin comprises an ion channel, the opening of which is stimulated by electromagnetic radiation of a suitable wavelength. For example, ChR2 is stimulated by light in the blue spectrum (e.g., about 450 nm to about 470 nm) and VChR1 is stimulated by light in the green spectrum (e.g., about 550 nm to about 570 nm).

Accordingly, in methods and compositions kits of some embodiments, the conditional ion modulator comprises an optogenetic receptor, and is stimulated by electromagnetic radiation, thus inducing opening of an ion channel and a change in polarity of the neuron that expresses the conditional ion modulator.

In some embodiments, the conditional ion modulator is configured to inhibit stimulation of a neuron or inhibit a neuron, for example by inducing a net efflux of cations from a cytosol and/or induce a net influx of anions to the cytosol. Such conditional ion modulators may be referred to herein as "inhibitory conditional ion modulators." Examples or such inhibitory conditional ion modulators include hM4Di, halorhodopsin, and archaeorhodopsin. hM4Di receptors can inhibit neurons upon stimulation with their agonist, CNO The hM4Di receptor comprises a modified form of the human M4 muscarinic (hM4) receptor. The hM4Di receptor can be activated by CNO, engaging the Gi signaling pathway. Gi signaling in neurons results in the opening of potassium channels and an influx of potassium ions, decreasing the capacity of the neuron to depolarize. Neurons expressing hM4Di that are treated with CNO can have decreased firing rates. Halorhodopsin comprises a transmembrane chloride channel, which can move chloride channels into the cell in response to electromagnetic radiation in the green to yellow spectrum of visible light. Archaeorhodopsin comprises a transmembrane proton pump, which can pump proteins out of the cell in response to light, thereby hyperpolarizing the neuron, and inhibiting an action potential by the neuron. In some embodiments, for example methods and compositions in which a conditional ion modulator inhibits a neuron, the conditional ion modulator comprises, consists essentially of, or consists of hM4Di, halorhodopsin, and/or archaeorhodopsin.

In some embodiments, the conditional ion modulator is configured to stimulate a neuron, for example by inducing a net influx of cations into a cytosol and/or induce a net efflux of anions from the cytosol. Such conditional ion modulators may be referred to herein as "stimulatory conditional ion modulators." Examples or such stimulatory conditional ion modulators include hM3DREADD and/or channelrhodopsin. In some embodiments, for example methods and compositions in which a conditional ion modulator inhibits a neuron, the conditional ion modulator comprises, consists essentially of, or consists of hM3DREADD and/or channelrhodopsin.

Vectors

In accordance with some embodiments, vectors are described. The vectors can be used to express nucleic acids (such as those encoding conditional ion modulators) in excitatory and/or inhibitory neurons of the LT, such as nNOS-positive and/or GLP1r-positive neurons of the LT as described herein. The vectors can be used to express nucleic acids such as conditional ion modulator nucleic acids in subjects in methods and compositions of some embodiment.

As used herein, the terms "nucleic acid" and "polynucleotide" are interchangeable and refer to nucleic acid, which may be composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

In methods and compositions of some embodiments, the vector comprises, consists essentially of, or consists of an adeno-associated virus (AAV) vector. AAV is a replication-deficient parvovirus, the single-stranded DNA genome of which is typically about 4.7 kb in length including 145 nucleotide inverted terminal repeat (ITRs). The ITRs play a role in integration of the AAV DNA into the host cell genome. When AAV infects a host cell, the viral genome integrates into the host's chromosome resulting in latent infection of the cell. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced. In the instances of recombinant AAV vectors having no Rep and/or Cap genes, the AAV can be non-integrating. AAVs can provide long-term transgene expression, they are not known to be associated with any human disease, they elicit a relatively weak immune response, and are capable of transducing a variety of cell types.

An AAV vector in accordance with methods and compositions of some embodiments herein can encode one or more gene products of interest, such as a conditional ion modulator, and can contain a promoter that is operably linked to the gene product(s) of interest. As such, upon insertion of the AAV vector into a mammalian cell such as a neuron, the gene product(s) of interest can be expressed. In methods and kits of some embodiments, an AAV is capable of delivering nucleic acids to a target environment, for example, a neuron (such as an excitatory or inhibitory neuron of the LT, for example an nNOS-positive neuron of the MnPO and/or SFO, and/or a GLP1r-positive neuron of the MnPO), a population of neurons, a tissue (such as a central nervous system (CNS) tissue), an organ (such as the brain, or in particular the LT), or a combination thereof, in a subject transduced with the AAV. The AAV may further comprise one or more inserted nucleic acids, which may be inserted into an insertion site, for example a multiple cloning site. The inserted nucleic acid may encode a conditional ion modulator as described herein. The AAV may further comprise a promoter operably linked to the inserted nucleic acid (or multiple cloning site). In some embodiments, an AAV comprises, from 5' to 3', a 5' ITR, a promoter, inserted nucleic acid (such as a conditional ion modulator nucleic acid), and a 3' ITR. In some embodiments, the AAV comprises a posttranscriptional regulatory element downstream of the restriction site and upstream of the 3' AAV ITR. In some embodiments, the AAV comprises a regulatory element, for example, a promoter, enhancer, splicing signal, polyadenylation signal, terminator, protein degradation signal, internal ribosome-entry element (IRES), 2A sequences, and the like, that provide for and/or regulate expression of a coding sequence and/or production of an encoded polypeptide in a host cell. The AAV in methods of some embodiments can target and deliver nucleic acids to the nervous system, for example, central nervous system (CNS) and/or peripheral nervous system (PNS) of a subject. For example, the capsid sequence of an AAV can be engineered to target an AAV to a neuron, and thus deliver a nucleic acid encoding an inducible receptor to the neuron. Examples of directed evolution methods for engineering AAV's targeted to cells (such as neurons) are described in detail in U.S. Pat. No. 9,585,971. In some embodiments, an AAV comprises a targeting peptide that can preferentially transduce neurons of the CNS or PNS. For example, the capsid of the AAV may comprise a targeting peptide which can target the AAV to the CNS or PNS. Examples of AAV, and AAV targeting peptides in particular that target the CNS are taught in US Pub. No. 2017/0166926, which is incorporated by reference in its entirety herein. Examples of AAVs (and targeting peptides) that efficiently transduce the CNS are shown in US Pub. No. 2017/0166926 at Table 3, for example AAV-PHP.B, AAV-PHP.B2, AAV-PHP.B. In some embodiments, the AAV comprises a targeting peptide selected from the group consisting of TLAVPFK (SEQ ID NO: 1), SVSKPFL (SEQ ID NO: 2), FTLTTPK (SEQ ID NO: 3), YTLSQGW (SEQ ID NO: 4), QAVRTSL (SEQ ID NO: 5), and LAKERLS (SEQ ID NO: 6). The targeting peptide can be configured to and/or sufficient to target the AAV to a neuron.

A suitable AAV can be produced using suitable genetic engineering techniques known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), which is incorporated by reference in its entirety herein.

In some embodiments a vector is described. The vector can comprise a nucleic acid encoding a conditional ion modulator configured to induce an increase in the quantity of cations in the cytosol of a neuron upon binding of an agonist or application of a stimulus to the conditional ion modulator. In some embodiments, the vector comprises a nucleic acid encoding a conditional ion modulator configured to induce a net efflux of cations from the cytosol of a neuron upon binding of an agonist or application of a stimulus to the conditional ion modulator. In some embodiments, a promoter is operably linked to the nucleic acid. The promoter can be configured to drive expression in excitatory and/or inhibitory neurons of the LT, for example nNOS-positive or GLP1r-positive neurons. In some embodiments, the promoter drives expression in nNOS-positive neurons of the SFO, and is selected from the group consisting of Gm3750, 1500017E21Rik, Rn45s, Malat1, Gnas, Mir1188, Nnat, Nrsn2, Rtn1, Nap115, Meg3, Snap25, Atp5b, Ubb, Hsp90ab 1, Rp141, Snhg11, Vsn11, Chgb, Pcp4, Ywhaz, Hspa8, Bex2, Ywhae, Calm2, Cam1, 6330403K07Rik, Gprasp 1, Rab7, and Peg3. In some embodiments, the promoter drives expression in GLP1r-positive neurons of the SFO and/or MnPO, and is selected from the group consisting of Rn45s, Malat1, Gnas, Ubb, Nap115, Rp141, Cst3, Hsp90ab1, Sod1, Fth1, Calm2, Lars2, Scg2, Rtn1, Atp5b, Snhg11, Meg3, Hspa8, Snap25, Pcp4, Mir686, Snora31, Gdi1, Bex2, Ywhaz, Eef1a1, Gm1821, Ywhae, Atp1b1, and Peg3. In some embodiments, the vector comprises a second nucleic acid encoding a conditional ion modulator. In some embodiments, a single promoter is operably linked to the first nucleic acid and second nucleic acid. In some embodiments, the vector comprises, consists essentially of, or consists of an adeno-associated virus (AAV). In some embodiments, two vectors are provided, in which the first vector comprises a first promoter operably linked to a first nucleic acid encoding a first conditional ion modulator, and the second vector comprises a second promoter operably linked to a second nucleic acid encoding a second conditional ion modulator that is different from the first conditional ion modulator. The first and second promoters can be promoters of genes specific to excitatory and/or inhibitory neurons of the LT as described herein. In some embodiments, the first and second promoter are the same. In some embodiments, the first and second promoter are different from each other. The first and second vector can be the same as each other or can be different from each other, for example having different regulatory elements such as different promoters.

Other types of vectors suitable for methods and compositions of some embodiments, include, for example, retroviral vectors such as lentiviral vectors (which can integrate into the genome of a host cell), and adenoviral vectors (which typically do not integrate into the genome of a host cell). In some embodiments, the vector is selected from the group consisting of an AAV vector, a lentiviral vector, and an adenoviral vector.

Promoters

A number of suitable promoters may be used to express conditional ion modulators in neurons in accordance with methods and compositions of some embodiments. The promoter may be disposed 5' of an inserted nucleic acid (or insertion site) in a vector as described herein, for example an AAV.

In some embodiments, the promoter drives expression in excitatory neurons of the SFO, for example, nNOS-positive neurons of the SFO. In some embodiments, the promoter is of a gene that is specifically or preferentially expressed in excitatory neurons of the SFO. Examples of genes that are preferentially expressed in excitatory neurons of the SFO (for example nNOS-positive neurons of the SFO) include Gm3750, 1500017E21Rik, Rn45s, Malat1, Gnas, Mir1188, Nnat, Nrsn2, Rtn1, Nap115, Meg3, Snap25, Atp5b, Ubb, Hsp90ab1, Rp141, Snhg11, Vsn11, Chgb, Pcp4, Ywhaz, Hspa8, Bex2, Ywhae, Calm2, Cam1, 6330403K07Rik, Gpraspl, Rab7, and Peg3. In some embodiment, the promoter is of a gene that is specifically or preferentially expressed in inhibitory neurons of the SFO and/or MnPO. Examples of genes that are preferentially expressed in inhibitory neurons of the SFO and MnPO (for example GLP1r neurons of the SFO and MnPO) include Rn45s, Malat1, Gnas, Ubb, Nap115, Rp141, Cst3, Hsp90ab1, Sod1, Fth1, Calm2, Lars2, Scg2, Rtn1, Atp5b, Snhg11, Meg3, Hspa8, Snap25, Pcp4, Mir686, Snora31, Gdi1, Bex2, Ywhaz, Eef1a1, Gm1821, Ywhae, Atp1b1, and Peg3.

As used herein, the term "operably linked" has its ordinary and customary meaning as would be understood by one of ordinary skill of the art in view of this disclosure. It refers to the connection between regulatory elements (such as promoters and/or enhancers) and a gene or its coding region. Typically, gene expression is placed under the control of one or more regulatory elements, for example, without limitation, constitutive or inducible promoters, tissue-specific regulatory elements, and enhancers. A gene or coding region said to be "operably linked to" or "operatively linked to" or "operably associated with" the regulatory elements, refers to the gene or coding region being controlled or influenced by the regulatory element. For instance, a promoter is operably linked to a coding sequence if the promoter effects transcription or expression of the coding sequence.

In methods and compositions of some embodiments, promoters, or promoter/enhancer sequences that yield constitutive or promiscuous expression in many cell types may be used. Examples of such promoters, or promoter/enhancer pairs include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF1alpha; and/or synthetic elements that are not present in nature.

In methods and compositions of some embodiments, a single promoter is operably linked to two or more gene product coding sequences. Accordingly, the single promoter can drive the expression of the two or more gene products. For example, a single promoter can be operably linked to two or more conditional ion modulators as described herein. The coding sequences of the two or more conditional ion modulators or subunits thereof can be separated by an element that permits the two gene products to be produced as separate polypeptides. For example the coding sequences of conditional ion modulators (or subunits) can be separated by an IRES, a 2A sequence, or a protease target site such as a furin consensus sequence (e.g., Arg-X-X-Arg, preferably Arg-X-Lys/Arg-Arg). Examples of 2A sequences are taught, for example, in U.S. Pat. No. 9,540,657 at Table 1.

In methods and compositions of some embodiments, two separate promoters are each operably linked to a different gene product coding sequences (such as two or more conditional ion modulators). For example, in some embodiments, a first promoter is operably linked to a first nucleic acid comprising, consisting essentially of, or consisting of a first conditional ion modulator (or subunit thereof) coding sequence, and a second promoter is operably linked to a second nucleic acid comprising, consisting essentially of, or consisting of a second conditional ion modulator (or subunit thereof) coding sequence.

As used herein, the term "enhancer" has its customary and ordinary meaning as understood by one of ordinary skill in the art in view of this disclosure. It refers to a type of regulatory element that can modulate the efficiency of transcription. In some embodiments, an enhancer modulates transcription regardless of the distance or orientation of the enhancer relative to the start site of transcription. In some embodiments, an enhancer modulates transcription regardless of the orientation of the enhancer relative to the start site of transcription.

Pharmaceutical Compositions

In methods and compositions of some embodiments, the nucleic acids (or vector comprising nucleic acids such as an AAV) are provided in a pharmaceutical composition. The pharmaceutical composition can be formulated for administration to a subject in need thereof. In the methods and kits of some embodiments, the pharmaceutical composition comprises, consists essentially of, or consists of the nucleic acids (encoding a conditional ion modulator as described herein) or vector(s) comprising the nucleic acids (such as AAV) and one or more pharmaceutically acceptable carriers. The pharmaceutical composition can also comprise additional ingredients such as diluents, stabilizers, excipients, and adjuvants. As used herein, "pharmaceutically acceptable" carriers, excipients, diluents, adjuvants, and/or stabilizers have their customary and ordinary meaning as would be understood by one of ordinary skill in the art in view of this disclosure. They refer to the ones nontoxic to the subject being exposed thereto (preferably inert) at the dosages and concentrations employed or that have an acceptable level of toxicity as determined by the skilled practitioners.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Titers of the nucleic acids (or vectors such as AAV comprising nucleic acids) to be administered will vary depending, for example, on the particular vector (such as a particular AAV), the mode of administration, the treatment goal, the individual, and the cell type(s) being targeted, and can be determined by methods standard in the art.

Administration and Dosing

The nucleic acids (and vectors comprising nucleic acids such as AAVs) can be administered to neurons of subjects by a number of suitable routes. In methods and kits of some embodiments, a therapeutically effective amount of the nucleic acid (or vectors comprising the nucleic acids such as AAVs) is administered to the subject by via one or more route standard in the art. Non-limiting examples of the route include intramuscular, intravaginal, intravenous, intraperitoneal, subcutaneous, epicutaneous, intradermal, rectal, intraocular, pulmonary, intracranial, intraosseous, oral, buccal, systematic, or nasal, or a combination of two or more of the listed items. In some embodiments, the nucleic acids (or vectors comprising the nucleic acids such as AAVs) are administered to the subject by systematic transduction. In some embodiments, the nucleic acids (or vectors comprising the nucleic acids such as AAVs) are administered to the subject by intramuscular injection. In some embodiments, the nucleic acids (or vectors comprising the nucleic acids such as AAVs) are administered to the subject by intravaginal injection. In some embodiments, the nucleic acids (or vectors comprising the nucleic acids such as AAVs) are administered to the subject by the parenteral route (e.g., by intravenous, intramuscular or subcutaneous injection), by surface scarification or by inoculation into a body cavity of the subject. Route(s) of administration and serotype(s) of vectors comprising nucleic acids (such as AAVs) can be readily determined by one skilled in the art taking into account the infection and/or disease state being treated and the target cells/tissue(s) that are to express the protein of interest. In some embodiments, it can be advantageous to administer the nucleic acids (or vectors comprising the nucleic acids such as AAVs) via intravenous administration. In methods, vectors, and/or compositions of some embodiments, the subject is a human. In methods, vectors, and/or compositions of some embodiments, the subject is a non-human primate.

In some embodiments, the nucleic acids (or vectors comprising the nucleic acids such as AAVs) are delivered to the nervous system (e.g., CNS, PNS, or PNS and CNS, or a portion thereof, such as the LT) of a subject, for example via injection, to a subject at a dose of between $1 \times 10^{10}$ genome copies (GC) of the nucleic acids (or vector such as AAV) per kg of the subject and $2 \times 10^{14}$ GC per kg, for example between $5 \times 10^{11}$ GC/kg and $5 \times 10^{12}$ GC/kg. In some embodiments, the dose of the nucleic acids (or vector such as AAV) administered to the subject is no more than $2 \times 10^{14}$ GC per kg. In some embodiments, the dose of the nucleic acids (or vector such as AAV) administered to the subject is no more than $5 \times 10^{12}$ GC per kg. In some embodiments, the dose of the nucleic acids (or vector such as AAV) administered to the subject is no more than $5 \times 10^{11}$ GC per kg.

Actual administration of the nucleic acids (or vector such as AAV) to the subject can be accomplished by using any physical method that will transport the nucleic acids (or vector such as AAV)into the target tissue of the subject. For example, the nucleic acids (or vector such as AAV) can be administered intravenously. As disclosed herein, capsid proteins of AAV's can be modified so that the AAV is targeted to a particular target environment of interest such as central nervous system, and to enhance tropism to the target environment of interest (e.g, CNS tropism). In some embodiments, an AAV delivers a nucleic acid to the heart, peripheral nerves, or a combination thereof. Pharmaceutical compositions can be prepared, for example, as injectable formulations.

The nucleic acids (or vector such as AAV) to be used can be utilized in liquid or freeze-dried form (in combination with one or more suitable preservatives and/or protective agents to protect the virus during the freeze-drying process). For gene therapy (e.g., of polydipsia, adipsia, and/or kidney damage, disease, or disorder as described herein, which may be ameliorated by a specific gene product) a therapeutically effective dose of the recombinant virus expressing the therapeutic protein is administered to a host in need of such treatment. The use of the recombinant virus disclosed herein in the manufacture of a medicament for inducing immunity in, or providing gene therapy to, a host is within the scope of the present application.

In instances where human dosages for nucleic acids (or vector such as AAV) have been established for at least some condition, those same dosages, or dosages that are between about 0.1% and 500%, more preferably between about 25% and 250% of the established human dosage can be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

A therapeutically effective amount of the nucleic acids (or vector such as AAV) can be administered to a subject at various points of time in accordance with methods and kits of some embodiments. For example, in methods and kits of some embodiments, the nucleic acids (or vector such as AAV) can be administered to the subject prior to, during, or after the subject has developed a disease or disorder such as dehydration, adispia, polydipsia, kidney stones, kidney damage disorder or dyfunction, or any other condition described herein. In methods and kits of some embodiments, the nucleic acids (or vector such as AAV) can also be administered to the subject prior to, during, or after the occurrence of a disease or disorder such as dehydration, adispia, polydipsia, kidney stones, kidney damage disorder or dysfunction, or any other condition described herein. In some embodiments, the neurological disease or disorder comprises, consists essentially of depression, anxiety, schizophrenia, post traumatic stress disorder, or a combination of two or more of the listed items. In some embodiments, the neurological disease or disorder comprises, consists essentially of social isolation stress, depression, anxiety, schizophrenia, or a combination of two or more of the listed items. In some embodiments, the neurological disease or disorder comprises, consists essentially of depression, anxiety, schizophrenia, or a combination of two or more of the listed items.

In methods and compositions of some embodiments, the nucleic acids (or vector such as AAV) are administered prior to the onset of the disease or disorder in the subject. In some embodiments, the nucleic acids (or vector such as AAV) are administered to a subject at a risk of developing the disease or disorder.

The dosing frequency of the nucleic acids (or vector such as AAV) administered in accordance with methods and kits of some embodiment can vary. For example, in methods and kits of some embodiments, the nucleic acids (or vector such as AAV) can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In methods and kits of some embodiments, the nucleic acids (or vector such as AAV) are administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

Methods of Stimulating Fluid Intake

In some embodiments, a method of stimulating fluid intake in a subject in need thereof is described. The method can comprise, in a first nitric oxide synthase (nNOS)-positive neuron of the median preoptic nucleus (MnPO) comprising a polarized cell membrane, stimulating depolarization of the cell membrane, thus stimulating the first nNOS-positive neuron. Thus, fluid intake in the subject can be stimulated. In some embodiments, the method further comprises identifying the subject as in need of stimulating fluid uptake. In some embodiments, stimulating fluid uptake comprises, consists essentially of, or consists of stimulating drinking behavior. In some embodiments, the method comprises administering a vector encoding a conditional ion modulator to the subject as described herein. In some embodiments, stimulating depolarization of the cell membrane comprises stimulating an action potential.

Wherever a method of stimulating fluid intake comprising the use of a composition is described herein (for example, a method comprising the use of a vector as described herein), the corresponding composition (e.g., vector) for use in stimulating fluid intake is also expressly contemplated. For example, for a method of stimulating fluid intake comprising administering a vector encoding a stimulatory conditional ion modulator (such as channelrhodopsin and/or hM3DREADD) as described herein, the vector for use in stimulating fluid intake is also expressly contemplated.

In some embodiments, stimulating depolarization of the cell membrane of the first nNOS-positive neuron comprises at least one of a net influx of cations into the cytosol of the first nNOS-positive neuron, a net efflux of anions from the cytosol of the first nNOS-positive neuron, and/or stimulating a second nNOS-positive neuron of the SFO. The second nNOS-positive neuron of the SFO can have a synapse with the first nNOS-positive neuron. In some embodiments, stimulating depolarization of the cell membrane of the first nNOS-positive neuron is performed by a stimulatory conditional ion modulator as described herein. In some embodiments, stimulating the second nNOS-positive neuron of the SFO is performed by a stimulatory conditional ion modulator in the second nNOS-positive neuron as described herein. In some embodiments, stimulating depolarization of the cell membrane of the first nNOS-positive neuron comprises a net influx of cations into the cytosol of the first nNOS-positive neuron. In some embodiments, depolarization of the cell membrane of the first nNOS-positive neuron is concurrent with stimulating the second nNOS-positive neuron. In some embodiments, depolarization of the cell membrane of the first nNOS-positive neuron and stimulating the second nNOS-positive neuron are performed at separate times, and/or with separate administrations of stimuli such as conditional ion modulator agonists. In some embodiments, depolarization of the cell membrane of the first nNOS-positive neuron is stimulated, and nNOS-positive neurons of the SFO are not stimulated. In some embodiments, depolarization of the cell membrane of the first nNOS-positive neuron is stimulated, even when GLP1r-positive neurons of the MnPO are stimulated.

In some embodiments, cations (such as those that exhibit a net influx into the cytosol of a neuron) comprise, consist essentially of, or consist of sodium cations (Nat), calcium cations ($Ca^{2+}$), protons ($H^+$), or a combination of these. It will be appreciated that since the cytosol of a neuron (such as an nNOS-positive neuron) comprises cations, a net influx of cations into the cytosol refers to an increase in the quantity of cations in the cytosol compared to prior to the influx. In some embodiments, the quantity of cations in the cytosol is increased by at least 1%, for example at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, 95%, 100%, 150%, 200%, 300%, 400%, or 500%, including ranges between any two of the listed values compared to prior to the influx. In some embodiments, the net influx of cations is effective to cause an action potential in the neuron. In some embodiments, anions (such as those that exhibit a net efflux from the cytosol of a neuron) comprise, consist essentially of, or consist of chloride anions ($Cl^-$). Similarly, it will be appreciated that since the cytosol of a neuron (such as an nNOS-positive neuron) comprises anions, a net efflux of anions from the cytosol refers to a decrease in the quantity of anions in the cytosol compared to prior to the efflux. In some embodiments, the quantity of anions in the cytosol is decreased by at least 1%, for example at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, 95%, 96%, 97%, 98%, 99%, or 99.9%, including ranges between any two of the listed values compared to prior to the efflux. In some embodiments, the net efflux of anions is effective to cause an action potential in the neuron.

In some embodiments, stimulating depolarization of the cell membrane of the first nNOS-positive neuron comprises inhibiting a GLP1r-positive neuron of the MnPO. The GLP1r-positive neuron of the MnPO can be inhibited by an inhibitory conditional ion modulator in the GLP1r-positive neuron as described herein.

In some embodiments, the method of stimulating fluid intake in a subject in need thereof comprises identifying the subject as in need of stimulating fluid intake. In some embodiments, the subject in need of stimulating fluid intake suffers from dehydration, adipsia, and/or hypodipsia. Accordingly, in some embodiments, the method is a method of treating, ameliorating, inhibiting, delaying the onset of, reducing the severity of, or preventing dehydration, adipsia, and/or hypodipsia. In some embodiments, the subject is an elderly subject. In some embodiments, the subject is a human or a non-human mammal. In some embodiments, stimulating fluid intake comprises, consists essentially of, or consists of stimulating drinking behavior. In some embodiments, fluid intake does not comprise eating behavior. In some embodiments, the subject in need suffers from kidney damage, kidney disease, kidney stones, and/or kidney dysfunction. It is contemplated that subjects suffering from kidney damage, kidney disease, kidney stones, and/or kidney dysfunction can be sensitive to dehydration, and that dehydration can exacerbate kidney damage, kidney disease, and/or kidney dysfunction. Accordingly, it is contemplated that increase fluid intake as described herein can ameliorate, inhibit, delay the onset of, reduce the severity of, or prevent kidney damage, kidney disease, kidney stones, and/or kidney dysfunction. Accordingly, in some embodiments, the method of stimulating fluid intake is a method of ameliorating, inhibiting, delaying the onset of, reducing the severity of, or preventing kidney damage, kidney disease, kidney stones, and/or kidney dysfunction in the subject. In some embodiments, the method of stimulating fluid intake is a method of ameliorating, inhibiting, delaying the onset of, reducing the severity of, or preventing dehydration, adipsia, hypodipsia, kidney damage, kidney disease, kidney stones, and/or kidney dysfunction in the subject.

By way of example, stimulating fluid intake can refer to stimulating an increase in the volume of fluid consumed (for example, an increase in the average daily volume of fluids consumed), and/or to stimulating an increase in the frequency of drinking fluids.

In the method of some embodiments, stimulating the increase in the quantity of cations in the cytosol of the first n-NOS-positive neuron comprises administering a nucleic acid encoding a stimulatory conditional ion modulator to the subject. The stimulatory conditional ion modulator can be configured to induce a net influx of cations into and/or a net efflux of anions from the cytosol of the first nNOS-positive neuron in response to a stimulus or. For example, the conditional ion modulator can comprise a cation channel or a G protein coupled receptor that is in communication with an ion channel via a signal transduction pathway. For example, the conditional ion modulator can comprise an anion channel such as a chloride channel. The nucleic acid can be under the control of a promoter that induces transcription of the nucleic acid in the first nNOS-positive neuron. Thus, the conditional ion modulator can be expressed in the first nNOS-positive neuron. The method can further comprise applying an agonist or stimulus to the first nNOS-positive neuron of the subject, causing the conditional ion modulator to induce the increase of cations in the cytosol of the first nNOS-positive neuron. For example, a cation channel can be opened so that cations move along a concentration and/or voltage gradient. In some embodiments, the conditional ion modulator is selected from the group consisting of a hM3DREADD, a channelrhodopsin, or a combination of the listed items. In some embodiments, the conditional ion modulator comprises, consists essentially of, or consists of a hM3DREADD, and the agonist or stimulus comprises CNO. In some embodiments, the conditional ion modulator comprises, consists essentially of, or consists of a channelrhodopsin, and the agonist or stimulus comprises electromagnetic radiation. In some embodiments, the nucleic acid encoding the conditional ion modulator is administered to the subject in a vector comprising the nucleic acid. The nucleic acid can be under the control of a promoter that expresses in excitatory neurons of the LT, such as nNOS-positive neurons of the SFO and/or MnPO. In some embodiments, the vector comprises, consists essentially of, or consists of a viral vector. In some embodiments, the vector comprises, consists essentially of, or consists of an adeno-associated viral (AAV) vector, as described herein.

In some embodiments, stimulating depolarization of the cell membrane of an nNOS-positive neuron (for example, the first nNOS-positive neuron of the MnPO) comprises at least one of: (i) depolarization of the nNOS-positive neuron; (ii) transmembrane influx of cations (such as sodium ions or protons) into the cytosol of the nNOS-positive neuron; (iii) influx of calcium ions from an endoplasmic reticulum (ER) to the cytosol of the nNOS-positive neuron; and/or efflux of anions (such as chloride ions) from the cytosol of the nNOS-positive neuron. In some embodiments, stimulating the increase in the quantity of cations in the cytosol of the first nNOS-positive neuron of the MnPO comprises (i) and (ii), (i) and (iii), (i) and (iv), (ii) and (iii), (ii) and (iv), (iii) and (iv), (i) and (ii) and (iii), (i) and (ii) and (iv), (i) and (iii) and (iv), or (ii) and (iii) and (iv). It will be appreciated that in some embodiments, stimulating the second nNOS-positive neuron of the SFO also comprises at least one of (i), (ii), (iii), or (iv). In some embodiments, stimulating the second nNOS-positive neuron of the SFO comprises (i) and (ii), (i) and (iii), (i) and (iv), (ii) and (iii), (ii) and (iv), (iii) and (iv), (i) and (ii) and (iii), (i) and (ii) and (iv), (i) and (iii) and (iv), or (ii) and (iii) and (iv).

In some embodiments, depolarization of the cell membrane comprises inhibiting a GLP1r-positive neuron of the MnPO. Inhibiting the GLP1r-positive neuron can comprise administering a nucleic acid encoding an inhibitory conditional ion modulator to the subject. The inhibitory conditional ion modulator can be configured to induce a net efflux of cations from and/or a net influx of anions into the cytosol of the GLP1r-positive neuron in response to a stimulus or agonist. For example, the conditional ion modulator can comprise a cation channel or pump, or can be in communication with a cation channel by way of a signal transduction pathway. For example, the conditional ion modulator can comprise an anion channel or pump, or can be in communication with an anion channel or pump by way of a signal transduction pathway. The nucleic acid encoding the inhibitory conditional ion modulator can be under the control of a promoter that induces transcription of the nucleic acid in the GLP1r-positive neuron. Thus, the inhibitory conditional ion modulator can be expressed in the GLP1r-positive neuron. In some embodiments, an agonist or stimulus is applied to the GLP1r-positive neuron of the subject, causing the inhibitory conditional ion modulator to induce the net efflux of cations from the cytosol of the GLP1r-positive neuron, for example by opening a cation channel and/or activating a cation pump (such as a proton pump). In some embodiments, an agonist or stimulus is applied to the GLP1r-positive neuron of the subject, causing the inhibitory conditional ion modulator to induce the net influx of anions into the cytosol of the GLP1r-positive neuron, for example by opening an anion channel (such as a chloride channel) and/or activating an anion pump. The GLP1r-positive neuron can have a synapse with the first nNos-positive neuron of the MnPO. In some embodiments, the conditional ion modulator comprises a hM4Di. The agonist or stimulus of the hM4Di can comprise clozapine-N-oxide (CNO). In some embodiments, the conditional ion modulator comprises a halorhodopsin, and/or an aarchaeorhodopsin. The agonist or stimulus can comprise electromagnetic radiation as described herein. In some embodiments, the conditional ion modulator comprises a hM4Di, a halorhodopsin, and/or an archaeorhodopsin. In some embodiments, the nucleic acid is administered to the subject in a vector comprising the nucleic acid. In some embodiments, the nucleic acid is under the control of a promoter that expresses in inhibitory neurons of the LT, such as inhibitory neurons of the MnPO and/or SFO as described herein. In some embodiments, the vector comprises, consists essentially of, or consists of a viral vector. In some embodiments, the vector comprises, consists essentially of, or consists of an adeno-associated viral (AAV) vector, as described herein.

In some embodiments, inhibiting the GLP1r-positive neuron comprises at least one of (i) hyperpolarizing the GLP1r-positive neuron, (ii) removing potassium ions and/or protons from the cytosol of the GLP1r-positive neuron; (iii) chloride ions entering into the cytosol of the GLP1r-positive neuron; or (iv) inhibiting release of calcium ions from an ER to the cytosol of the GLP1r-positive neuron. In some embodiments, inhibiting the GLP1r-positive neuron comprises (i) and (ii), or (i) and (iii), or (i) and (iv), or (ii) and (iii), or (ii) and (iv), or (iii) and (iv), or (i) and (ii) and (iii), or (i) and (ii) and (iv), or (i) and (iii) and (iv), or (ii) and (iii) and (iv), or (i) and (ii) and (iii) and (iv).

In some embodiments, the method of stimulating fluid intake in a subject in need thereof comprises, in a polarized first nNOS-positive neuron of the MnPO that comprises a cytosol comprising a quantity of cations, translocating cations into the cytosol and inhibiting a GLP1r-positive neuron of the MnPO as described herein. In some embodiments, the method of stimulating fluid intake in a subject in need thereof comprises, in a polarized first nNOS-positive neuron of the MnPO that comprises a cytosol comprising a quantity of cations, translocating cations into the cytosol and inhibiting a GLP1r-positive neuron of the MnPO as described herein.

In some embodiments, the method of stimulating fluid intake in a subject in need thereof comprises, in a polarized first nNOS-positive neuron of the MnPO that comprises a cytosol comprising a quantity of cations, translocating cations into the cytosol and stimulating a second nNOS-positive neuron of the SFO as described herein. The second nNOS-positive neuron of the SFO can synapse with the first nNOS-positive neuron of the MnPO.

In some embodiments, the method of stimulating fluid intake in a subject in need thereof comprises stimulating a second nNOS-positive neuron of the SFO and/or inhibiting a GLP1r-positive neuron of the MnPO as described herein. The GLP1r-positive neuron of the MnPO can synapse with the first nNOS-positive neuron of the MnPO. The second nNOS-positive neuron of the SFO can synapse with the first nNOS-positive neuron of the MnPO.

In some embodiments, the method of stimulating fluid intake in a subject in need thereof comprises, in the first nNOS-positive neuron of the MnPO, inducing a net influx of cations into the cytosol of the first nNOS-positive neuron, stimulating the second nNOS-positive neuron in the SFO, and inhibiting a GLP1r-positive neuron of the MnPO as described herein. In some embodiments, the method of stimulating fluid intake in a subject in need thereof comprises, in the first nNOS-positive neuron of the MnPO, inducing a net influx of cations into the cytosol of the first nNOS-positive neuron, stimulating the second nNOS-positive neuron in the SFO, and/or inhibiting a GLP1r-positive neuron of the MnPO as described herein. The GLP1r-positive neuron of the MnPO can synapse with the first neuron, and/or the second nNOS-positive neuron of the SFO can synapse with the first neuron.

Methods of Inhibiting Fluid Intake

In some embodiments, a method of inhibiting fluid intake in a subject in need thereof is described. The method can comprise, in a first nNOS-positive neuron of the MnPO comprising a cell membrane, inhibiting depolarization of the cell membrane. Thus, stimulation of the first nNOS-positive neuron can be inhibited, thus inhibiting fluid intake. Thus, fluid intake in the subject can be inhibited. For conciseness "inhibiting stimulation" of a neuron (e.g., the first nNOS-positive neuron) may be referred to herein as "inhibiting" the neuron. In some embodiments, the method comprises at least one of inhibiting cation influx into a cytosol of the first nNOS-positive neuron, inducing anion influx into the cytosol of the first nNOS-positive neuron inducing cation efflux from the cytosol of the first nNOS-positive neuron, inhibiting a second nNOS-positive neuron of the subfornical organ (SFO), stimulating a GLP1r-positive neuron of the MnPO. In some embodiments, the method comprises administering a vector encoding a conditional ion modulator to the subject as described herein. In some embodiments, inhibiting the second nNOS-positive neuron comprises administering an anti-nNOS antibody to the subject.

Wherever a method of inhibiting fluid intake comprising the use of a composition is described herein (for example, a method comprising the use of a vector as described herein), the corresponding composition (e.g., vector) for use in inhibiting fluid intake is also expressly contemplated. For example, for a method of stimulating fluid intake comprising administering a vector encoding a hM4Di as described herein, the vector for use in stimulating fluid intake is also expressly contemplated.

In some embodiments, the method comprises inhibiting cation influx into the first nNOS-positive neuron and/or inhibiting a second nNOS-positive neuron of the SFO, and/or stimulating a GLP1r-positive neuron of the MnPO. The second nNOS-positive neuron of the SFO can synapse with the first neuron, and/or the GLP1r-positive neuron of the MnPO can synapse with the first neuron. In some embodiments, cation influx into the cytosol of the first nNOS-positive neuron is inhibited concurrently with inhibiting the second nNOS-positive neuron and/or stimulating the GLP1r-positive neuron of the MnPO. The concurrent events can be induced by the same agonist stimulus (e.g., CNO, or a particular wavelength range of electromagnetic radiation), or by different agonists or stimuli. In some embodiments, inhibiting influx of cations into the cytosol of the first nNOS-positive neuron and/or inhibiting the second nNOS-positive neuron and/or stimulating a GLP1r-positive neuron of the MnPO are performed at separate times, and/or with separate administrations of stimuli such as conditional ion modulator agonists and/or electromagnetic radiation. In some embodiments, depolarization of the cell membrane of the first nNOS-positive neuron is inhibited, even when nNOS-positive neurons of the SFO are stimulated. In some embodiments, depolarization of the cell membrane of the first nNOS-positive neuron is inhibited, even when GLP1r-positive neurons of the MnPO are not stimulated.

In some embodiments, inhibiting the second nNOS-positive neuron comprises administering an antibody to the subject, for example an antibody specific to nNOS (or anti-nNOS antibody). It is noted that the SFO is not protected by the blood brain barrier, and as such, nNOS neurons of the SFO can be targeted by molecules in the bloodstream. By way of example, rabbit polyclonal anti-nNOS (Santa Cruz, sc-648) binds specifically to nNOS, as does mouse monoclonal IgG$_1$ antibody A-11 (Santa Cruz, sc-5302). In some embodiments, the antibody comprises a chimeric antibody comprising the variable regions of mouse monoclonal IgG$_1$ antibody A-11, or a humanized antibody comprising the CDRs of mouse monoclonal IgG$_1$ antibody A-11.

In some embodiments, the method comprises inhibiting cation influx into the first nNOS-positive neuron and/or stimulating a GLP1r-positive neuron of the MnPO. In some embodiments, the method comprises inhibiting a second nNOS-positive neuron of the SFO and stimulating a GLP1r-positive neuron of the MnPO). In some embodiments, the method comprises inhibiting cation influx into the first nNOS-positive neuron, inhibiting a second nNOS-positive neuron of the SFO and stimulating a GLP1r-positive neuron of the MnPO. By way of example, the second nNOS-positive neuron of the SFO can be inhibited by an inhibitory conditional ion modulator in the second nNOS-positive neuron as described herein. By way of example, the GLP1r-positive neuron of the MnPO can be stimulated by an stimulatory conditional ion modulator in the GLP1r-positive neuron of the MnPO as described herein.

In some embodiments, the method further comprises identifying the subject as in need of inhibiting fluid intake. For example, the subject can be identified as suffering from polydipsia. In some embodiments, the subject suffers from polydipsia. In some embodiments, the subject is a human or a non-human mammal. In some embodiments, the subject is an elderly subject. In some embodiments, the fluid intake comprises drinking behavior. In some embodiments, fluid intake does not comprise eating behavior. In some embodiments, inhibiting fluid intake comprises, consists essentially of, or consists of inhibiting drinking behavior. In some embodiments, the method of inhibiting fluid intake is a method of ameliorating, inhibiting, delaying the onset of, reducing the severity of, or preventing polydipsia.

In some embodiments, the cations comprise, consist essentially of, or consist of protons, sodium cations, calcium cations, or a combination of these. It will be appreciated that since the cytosol of a neuron (such as an nNOS-positive neuron) comprises cations, a net efflux of cations into the cytosol refers to an decrease in the quantity of cations in the cytosol compared to prior to the efflux. In some embodiments, the quantity of cations in the cytosol is decreased by at least 1%, for example at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, 95%, 96%, 97%, 98%, 99%, or 99.9%, including ranges between any two of the listed values compared to prior to the efflux. In some embodiments, the net efflux of cations is effective to prevent an action potential in the neuron. In some embodiments, anions (such as those that exhibit a net influx into the cytosol of a neuron) comprise, consist essentially of, or consist of chloride anions (Cl$^-$). Similarly, it will be appreciated that since the cytosol of a neuron (such as an nNOS-positive neuron) comprises anions, a net influx of anions from the cytosol refers to an increase in the quantity of anions in the cytosol compared to prior to the efflux. In some embodiments, the quantity of anions in the cytosol is increased by at least 1%, for example at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, 95%, 100%, 150%, 200%, 300%, 400%, or 500%, including ranges between any two of the listed values compared to prior to the efflux. In some embodiments, the net influx of anions is effective to prevent an action potential in the neuron.

In the method of some embodiments, inhibiting the increase in the quantity of cations in the cytosol of the first nNOS-positive neuron comprises administering a nucleic acid encoding a inhibitory conditional ion modulator to the subject. The inhibitory conditional ion modulator can be configured to induce a net efflux of cations from the cytosol of the first nNOS-positive neuron and/or a net influx of anions into the cytosol of the first nNOS-positive neuron in response to a stimulus or agonist. For example, the inhibitory conditional ion modulator can comprise an ion channel or ion pump or a G protein coupled receptor that is in communication with an ion channel or ion pump via a signal transduction pathway as described herein. The nucleic acid can be under the control of a promoter that induces transcription of the nucleic acid in the first nNOS-positive neuron. Thus, the inhibitory conditional ion modulator can be expressed in the first nNOS-positive neuron. The method can further comprise applying an agonist or stimulus to the first nNOS-positive neuron of the subject, causing the inhibitory conditional ion modulator to induce the net efflux of cations from the cytosol of the first nNOS-positive neuron. For example, a cation channel can be opened so that cations exit along a concentration and/or voltage gradient, and/or cations can be pumped out of the neuron. In some embodiments, the inhibitory conditional ion modulator comprises, consists essentially of, or consists of a hM4D1, a halorhodopsin, and/or an archaeorhodopsin. In some embodiments, the agonist or stimulus comprises CNO or electromagnetic radiation. In some embodiments, the inhibitory conditional ion modulator comprises, consists essentially of, or consists of a hM4Di, and the agonist or stimulus comprises CNO. In some embodiments, the inhibitory conditional ion modulator comprises, consists essentially of, or consists of a halorhodopsin, and/or an archaeorhodopsin, and the agonist or stimulus comprises electromagnetic radiation. In some embodiments, the nucleic acid encoding the inhibitory conditional ion modulator is administered to the subject in a vector comprising the nucleic acid. In some embodiments, the vector comprises, consists essentially of, or consists of a viral vector. In some embodiments, the vector comprises, consists essentially of, or consists of an AAV vector, as described herein.

1. In some embodiments, inhibiting an nNOS-positive neuron (such as inhibiting depolarization of the cell membrane of the first nNOS-positive neuron of the MnPO and/or inhibiting the second nNOS-positive neuron of the SFO) comprises at least one of: (i) hyperpolarization of the nNOS-positive neuron; (ii) transmembrane efflux of potassium cations from the cytosol of the nNOS-positive neuron; (iii) transmembrane influx of chloride anions into the cytosol of the nNOS-positive neuron; (iv) inhibition of influx of calcium ions from an endoplasmic reticulum (ER) to the cytosol of the nNOS-positive neuron; or (v) administering an anti-nNOS antibody to the subject (which can inhibit the second nNOS-positive neuron of the SFO). In some embodiments, inhibiting depolarization of the cell membrane of an nNOS-positive neuron of the MnPO (for example, the first nNOS-positive neuron) and/or inhibiting a second nNOS-positive neuron of the subfornical organ (SFO) comprises (i) and (ii), (i) and (iii), (i) and (iv), (i) and (v), (ii) and (iii), (ii) and (iv), (ii) and (v), (iii) and (iv), (iii) and (v), (iv) and (v), (i) and (ii) and (iii), (i) and (ii) and (iv), (i) and (ii) and (v), (i) and (iii) and (iv), (i) and (iii) and (v), (i) and (iv) and (v), (ii) and (iii) and (iv), (ii) and (iii) and (v), (ii) and (iv) and (v), (iii) and (iv) and (v), (i) and (ii) and (iii) and (iv), (i) and (ii) and (iii) and (v), (i) and (ii) and (iv) and (v), (i) and (iii) and (iv) and (v), (ii) and (iii) and (iv) and (v), or (i) and (ii) and (iii) and (iv) and (iv).

In some embodiments, stimulating a GLP1r-positive neuron of the MnPO comprises administering a nucleic acid encoding a stimulatory conditional ion modulator to the subject. The stimulatory conditional ion modulator can be configured to induce a net influx of cations into the cytosol of the GLP1r-positive neuron in response to a stimulus or agonist. For example, the stimulatory conditional ion modulator can comprise a cation channel or pump or a G protein coupled receptor that is in communication with an ion channel or pump via a signal transduction pathway as described herein. The nucleic acid can be under the control of a promoter that induces transcription of the nucleic acid in the GLP1r-positive neuron. Thus, the stimulatory conditional ion modulator can be expressed in the GLP1r-positive neuron. The method can further comprise applying an agonist or stimulus to the GLP1r-positive neuron of the subject, causing the stimulatory conditional ion modulator to induce a net influx of cations to the cytosol of the GLP1r-positive neuron and/or induce a net efflux of anions from the cytosol of the GLP1r positive neuron. In some embodiments, the stimulatory conditional ion modulator is selected from the group consisting of a hM3DREADD, a channelrhodopsin, or a combination of the listed items. In some embodiments, the stimulatory conditional ion modulator comprises, consists essentially of, or consists of a hM3DREADD, and the agonist or stimulus comprises CNO. In some embodiments, the stimulatory conditional ion modulator comprises consists essentially of, or consists of a channelrhodopsin, and the agonist or stimulus comprises electromagnetic radiation. In some embodiments, the nucleic acid encoding the stimulatory conditional ion modulator is administered to the subject in a vector comprising the nucleic acid. The nucleic acid can be under the control of a promoter that expresses in inhibitory neurons of the LT, such as inhibitory neurons of the MnPO, such as GLP1r neurons. In some embodiments, the vector comprises, consists essentially of, or consists of a viral vector. In some embodiments, the vector comprises, consists essentially of, or consists of an AAV vector, as described herein.

In some embodiments, stimulating a GLP1r-positive neuron of the MnPO comprises at least one of: (i) depolarization of the GLP1r-positive neuron; (ii) transmembrane influx of sodium cations into the cytosol of the GLP1r-positive neuron; or (iii) influx of calcium ions from an ER to the cytosol of the GLP1r-positive neuron. In some embodiments, stimulating the GLP1r-positive neuron of the MnPO neuron comprises (i) and (ii), (i) and (iii), (ii) and (iii), or (i) and (ii) and (iii). In some embodiments, inhibiting the second nNOS-positive neuron of the SFO comprises administering an nNOS-specific antibody to the subject.

Methods of Monitoring Thirst Satiation

In some embodiments, a method of monitoring thirst satiation in a subject in need thereof is described. The method can comprise monitoring or detecting the level of $Ca^{2+}$ excitatory neuron of the LT such as nNOS-positive neuron of the MnPO and/or SFO of the subject in real time. For example, the level $Ca^{2+}$ cytosol of the nNOS-positive neuron can be detected via in vivo imaging, such as functional Magnetic Resonance Imaging (fMRI) or Positron Emission Tomography (PET). For example, a reporter such as GCaMP6s can be observed in vivo. Nucleic acid encoding the reporter such as GCaMP6s can be delivered to the subject for expression in neurons of the LT (such as nNOS-positive neuron of the MnPO and/or SFO) using a vector such as an AAV described herein. As used herein "real time" has its customary and ordinary meaning as would be understood by one of ordinary skill in the art in view of its disclosure. It can refer to detecting the level of $Ca^{2+}$ the excitatory neuron of the LT concurrently with the actual Ca$^{2+}$ or within 60 seconds of the actual Ca$^{2+}$ for example within 60, 50, 40, 30, 20, 10, 5, 4, 3, 2, 1, or 0.1 seconds.

Additional Embodiments

Without being limited by theory, neural circuits for appetites are regulated by both internal homeostatic perturbations [1]-[4] and ingestive behaviors[5]-[8]. The circuit organization that processes these internal and external stimuli is anatomically and genetically complex[4],[9]. Without being limited by theory, we used cell-type-specific neural manipulation, RNA sequencing, and deep-brain optical recording in mice to dissect genetically-defined homeostatic circuits that regulate thirst. We showed that multiple excitatory neural populations in the lamina terminalis form an interconnected and hierarchical circuit architecture to mediate drinking behavior. Among these populations, nitric oxide synthase (nNos)-expressing neurons in the median preoptic nucleus (MnPO) play a role in integrating signals from thirst-driving neurons of the subfornical organ (SFO[10],[11]) to coordinate drinking. Silencing these neurons abolishes water intake in thirsty animals without impairing the osmosensory function of SFO neurons. On the other hand, we found a distinct inhibitory circuit that encodes drinking-induced rapid thirst alleviation. Specific inhibitory neurons in the MnPO that express glucagon-like peptide 1 receptor (GLP1r) were activated immediately upon drinking behavior. These responses were not specific for water but induced by liquid ingestion, and time-locked to the onset and offset of drinking. We demonstrated that this inhibitory population suppressed thirst-driving SFO neurons through a monosynaptic connection. Furthermore, acute and chronic loss-of-function manipulations of GLP1r-expressing MnPO neurons led to a polydipsic over-drinking phenotype. Thus, without being limited by theory, these neurons facilitate satiety of thirst by monitoring real-time fluid ingestion. Together, our study revealed dynamic thirst circuits that integrate the homeostatic-instinctive need and its consequent drinking behavior to maintain internal water balance.

Without being limited by theory, the precise regulation of water intake helps to maintain body fluid homeostasis. The initiation of water drinking is triggered by internal fluid imbalance in animals such as water depletion[1],[3],[12]. In contrast, drinking termination rapidly occurs when animals ingest a sufficient amount of water, which generally precedes the absorption of ingested fluid[7],[8],[13]. To achieve such accurate fluid regulation, the brain needs to monitor both internal water balance as well as fluid ingestion on a real-time basis[14]. The brain integrates homeostatic and behavioral inputs to orchestrate drinking behaviour. Without being limited by theory, uncovering the neural circuits that process these regulatory signals is, therefore, an important step for understanding the neural logic of thirst regulation.

The lamina terminalis (LT) is a main brain structure responsible for sensing and regulating internal water balance [12],[15]-[17]. It contains three main nuclei, the SFO, MnPO, and vascular organ of lamina terminalis (OVLT) that are anatomically interconnected. Recent studies have shown that specific neural populations in the LT have a causal role in regulating drinking behavior. For instance, optogenetic and chemogenetic activation of excitatory SFO neurons expressing nNos (SFO$^{nNos}$ neurons) drives immediate and robust drinking behaviour[10],[18],[19]. Conversely, stimulation of inhibitory populations of LT nuclei suppresses water intake[10],[20]. These studies pinpointed neural substrates regulating thirst without describing the circuit organization that mediates drinking behaviour.

In some embodiments, excitatory and/or inhibitory populations of the LT are manipulated to address individual contributions to behavioral output. In some embodiments, complex regulatory signals at sensing areas contribute to the maintenance of body fluid homeostasis.

MATERIALS AND METHODS FOR EXAMPLES 1-5

Animals

All animal procedures were in accordance to the US National Institutes of Health (NIH) guidance for the care and use of laboratory animals and were approved by the IACUC (Protocol No: 1694-14. California Institute of Technology). Mice used for data collection were both males and females, at least 8 weeks of age. The following animals were purchased from the Jackson Laboratory (C57BL/6J; stock number 000664, Slc32a1 (Vgat)-Cre; stock number 016962, Ai9; stock number 007909, Ai3; stock number 007903, Slc17a6 (Vglut2)-Cre; stock number 016963 and NOS1-Cre; stock number 017526). GLP1r-Cre and Ai10 lines were generously provided by Fiona Gribble (Cambridge) and David Anderson (Caltech), respectively. Animals were housed in temperature, humidity controlled rooms with a 13 hour light-11 hour dark cycle with ad libitum access to chow and water.

Viral Constructs

The following AAVs were purchased from the UNC Vector Core-AAV1-CA-FLEX-RG—4e12 copies/mL, AAV1-EF1a-FLEX-TVA-mCherry—6e12 copies/mL, AAV2-EF1a-DIO3 hChR2-eYFP—5.6e12 copies/mL, AAV2-hSyn-DIO-hM4D(Gi)-mCherry—3.7e12 copies/mL, AAV2-EF1a-DIO-mCherry—5.7e12 copies/mL, AAV5-CamKIIa-hM4D(Gi)-mCherry—4.3e12 copies/mL, AAV5-CamKIIa-hM3D(Gq)-mCherry—1.7e12 copies/mL, AAVS-FLEX-taCasp3-TEVp—5.3e12 copies/mL. The following AAVs were purchased from the UPenn Vector Core-AAV1-Syn-FLEX-GCaMP6 s-WPRE-SV40—2.9e13 GC/mL, AAV1-Syn-GC aMP6s-WPRE-SV40—2.28e13 GC/mL, AAV1-CamK11-eYFP-WPRE9 hGH—1.86e13 GC/mL, AAV2-EF1a-DIO-eYFP-WPRE-hGH—3.05e12 GC/mL. EnvA G10 deleted Rabies-eGFP (1.6e8 TU/mL) was purchased from the Salk Institute. Herpes Simplex Virus (hEF1a-LS1L-mCherry HT) was purchased from the Vector Core Facility at MIT.

Surgery

All procedures were adopted from the previous report[10]. Mice were anaesthetized with a mixture of ketamine (1 mg/mL) and xylazine (10 mg/mL) in isotonic saline, injected intraperitoneally at 10 µL/g bodyweight. The mice were then placed in a stereotaxic apparatus (Narishige Apparatus) on a heating pad. An incision was made to expose the skull. The 3 dimensional MRI coordinate system was used for aligning the skull reference. A small craniotomy <1 mm was made using a hand drill at the regions of interest. Viral constructs were injected using a pressure injection system (Nanoliter 2000) using a pulled glass capillary at 100 nL/min. The coordinates are AP: −4030, ML: 0, DV: −2550 (200 nL injection) for the SFO, AP: −3100 ML: 0 DV: −4080 (100 nL injection) and −3800 (50-100 nL injection) for the MnPO, and AP: −2700, ML: 0, DV: −4900 (75 nL injection) for the OVLT. For optogenetic implants, a 200 µm fiber bundle (FT200EMT, Thorlabs) glued to a ceramic ferrule (Thorlabs) with epoxy was used. For photometry implants, a 400 µm fiber bundle (BFH48-400, Thorlabs) glued to a ceramic ferrule with low auto fluorescence epoxy (EPO-TEK301) or a custom made implant (Doric Lenses) was used. A fiber was implanted 200-300 μm (for photostimulation) or 0-50 mm (for photometry) above the virus injection site. After applying a local anesthetic to the sides of the skin incision, the implants were permanently fixed to the skull using dental cement. Cannulated animals were placed in a clean cage on a heating pad for recovery from anesthesia. Animals were kept in their home cage for at least 10 days before any behavior tests.
Photostimulation For optogenetic experiments, photostimulation was performed using 473 nm laser pulses—20 ms, 5 (OVLT) or 20 Hz (SFO and MnPO) delivered via a custom made optic cable using a pulse generator (World Precision Instruments). The laser intensity was maintained at 5 (OVLT) or 10 mW (SFO and MnPO) at the tip of the fiber.
Behavioral Assays For water-restriction experiments, animals were provided with 1 mL of water daily. For food restriction experiments, animals were provided 0.5 pellets/20 g body weight daily. All assays were performed in a modified lickometer as described previously[35] or Biodaq monitoring system (Research Diets Inc). For all photometry assays, animals were acclimatized for 10-15 min in the lickometer cage before stimuli were given.

Figure 12A:
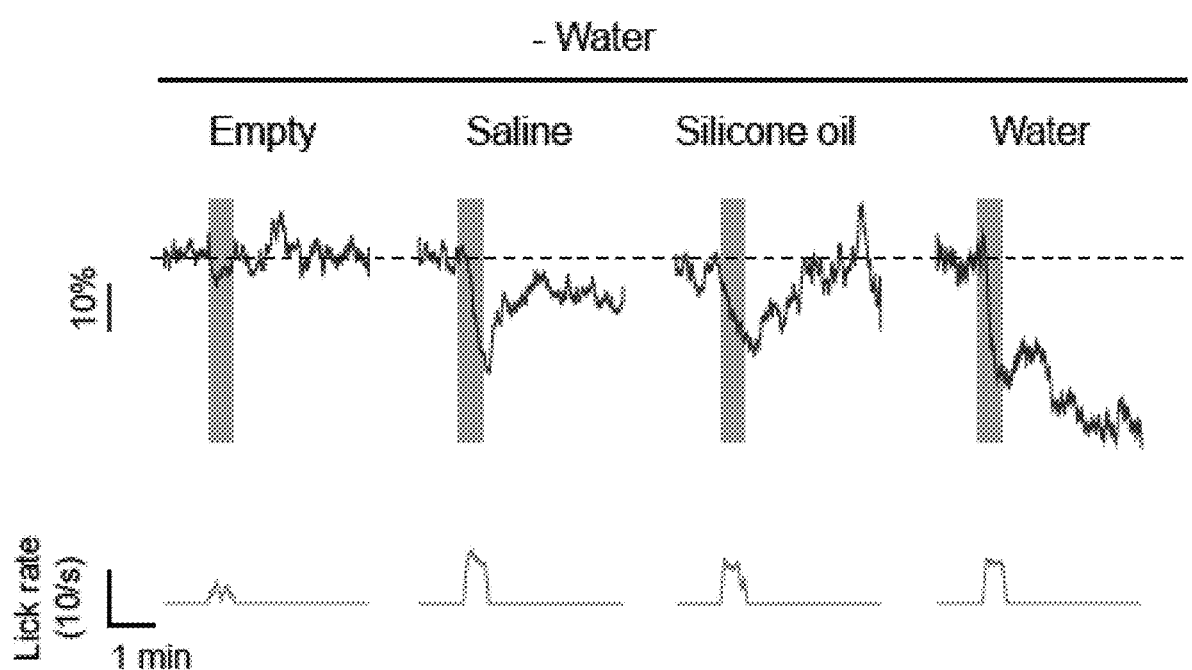
FIGS. 12A-O show in vivo activation patterns of MnPO$^{GLP1r}$ and SFO$^{nNOS}$ neurons to different stimuli.
Figure 12B:
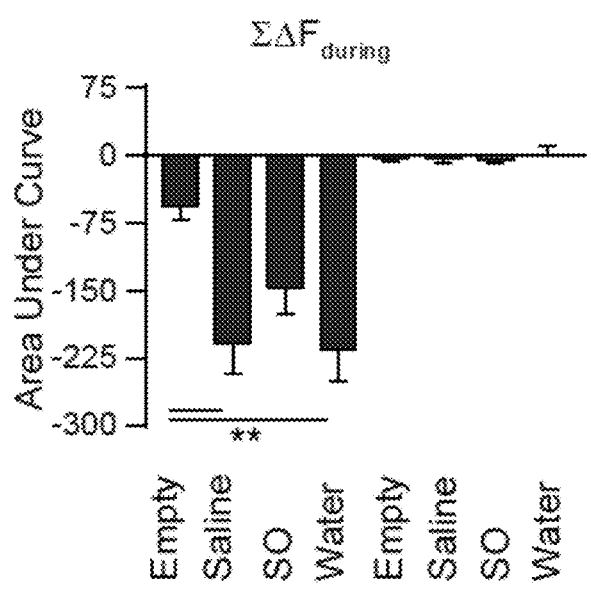
Figure 12C:
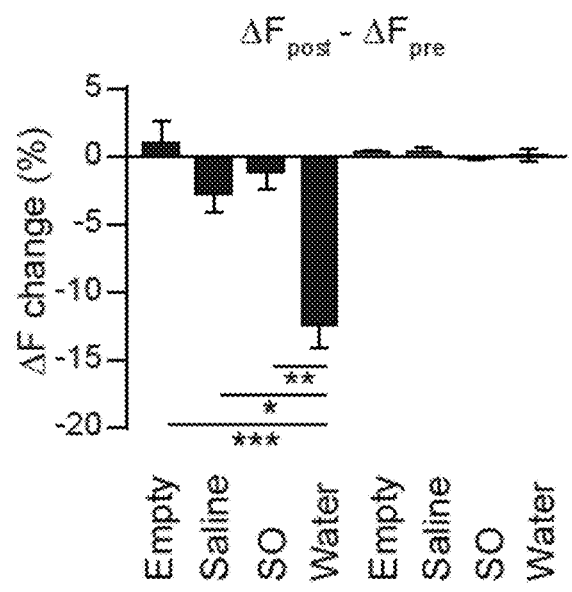
Figure 12D:
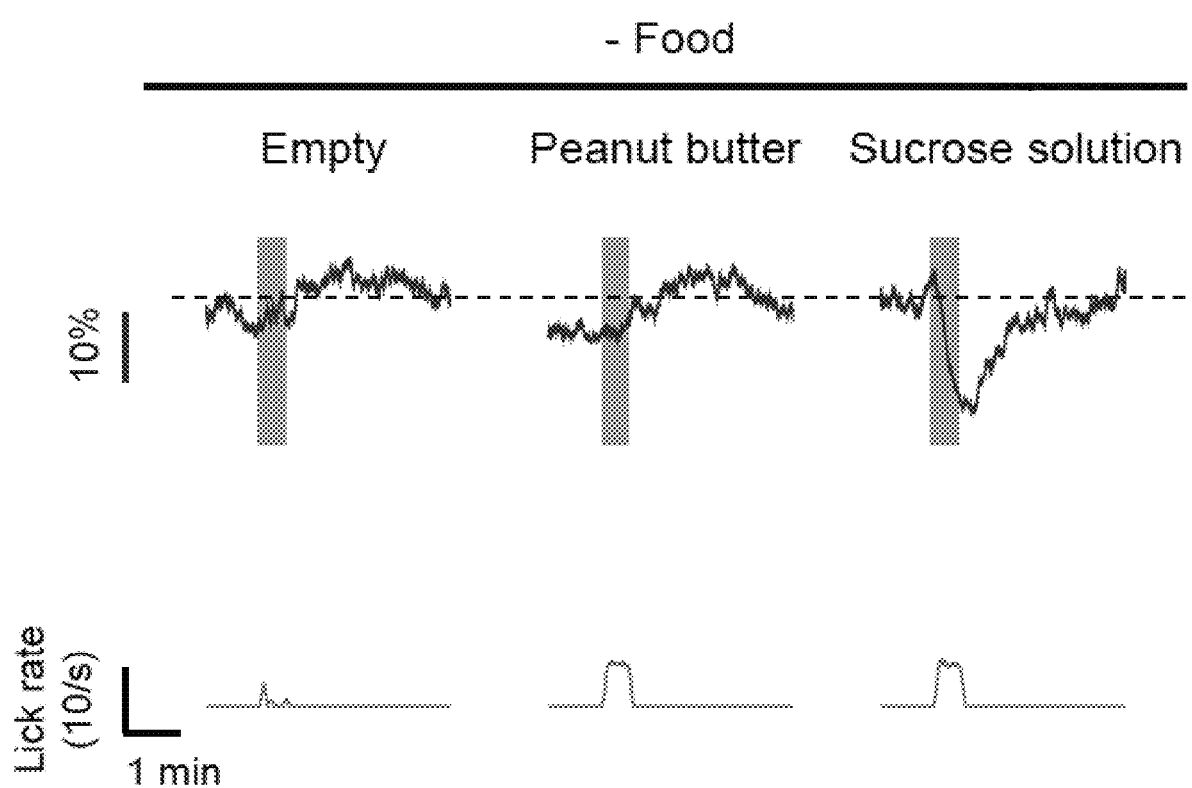
Figure 12E:
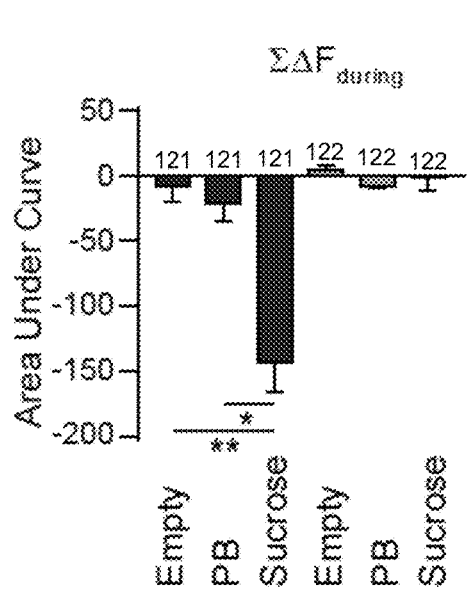
Figure 12F:
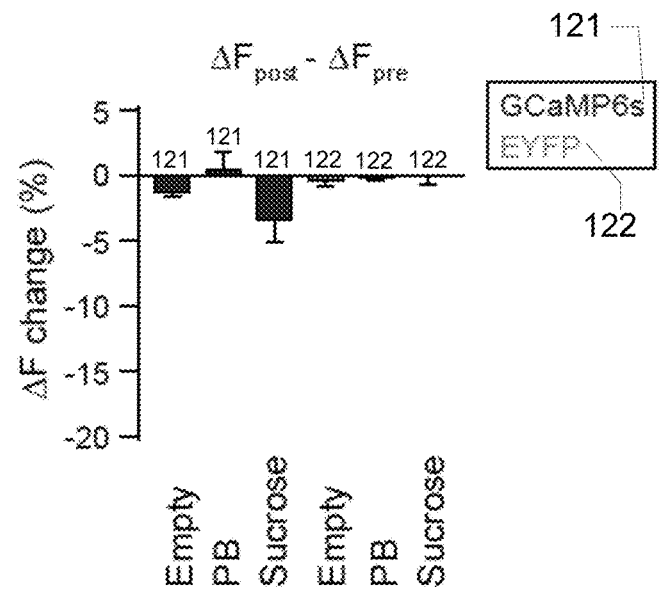
Figure 12G:
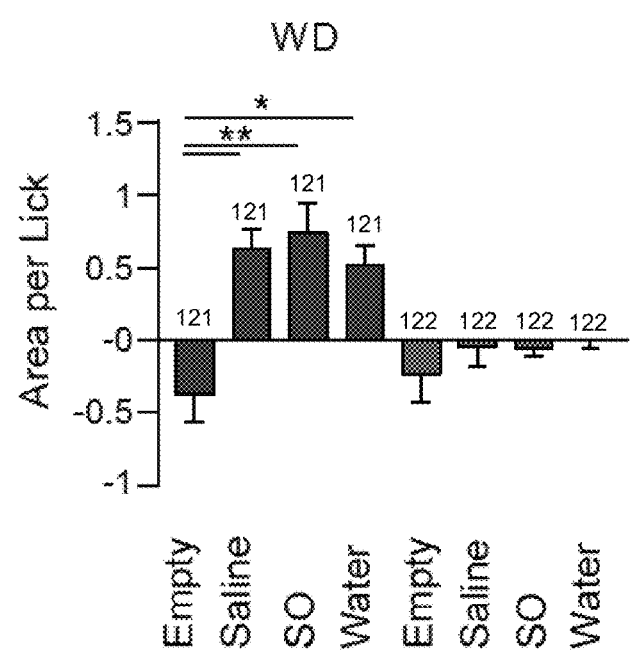
In FIGS. 12G-H, activity change per lick was quantified for MnPO$^{GLP1r}$ neurons (GCaMP6s 121, first to fourth bar from left; eYFP 122, fifth to eighth bar from left in FIG. 12G; GCaMP6s 121, first to third bar from left; eYFP 122, fourth to sixth bar from left in FIG. 12H) under water-restricted conditions (left, n=6 for saline and silicone oil, n=7 for empty and water, n=6 for all eYFP controls) and food-restricted conditions (right, n=6 for empty and peanut butter, n=7 for sucrose, n=6 for all eYFP controls).
Figure 12H:
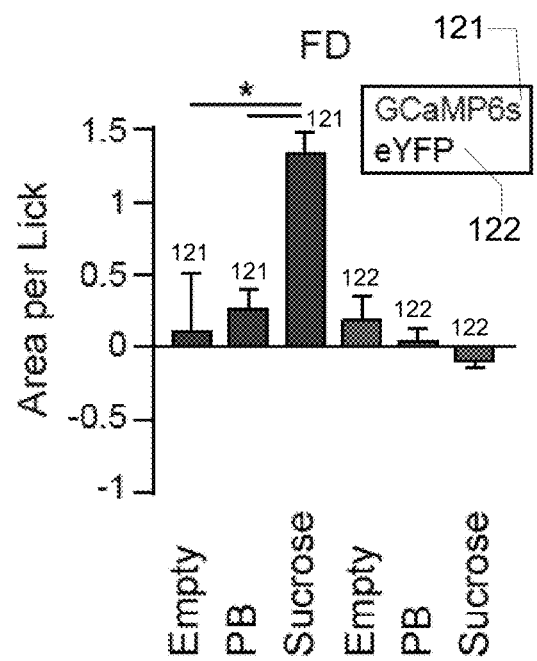
Figure 12I:
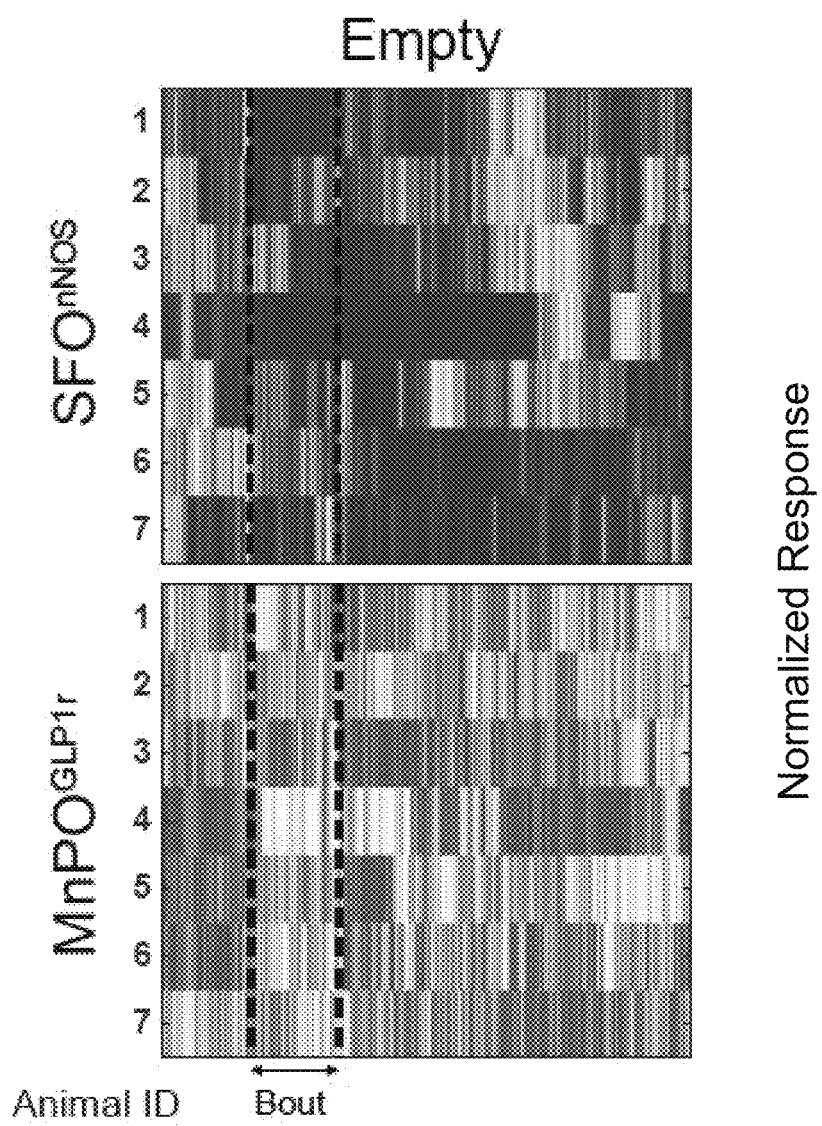
FIGS. 12I-K show normalized fluorescence change of SFO$^{nNOS}$ (upper) and MnPO$^{GLP1r}$ (lower) neurons from individual animals during licking an empty bottle and water under water-restricted, or sucrose under food-restricted conditions.
Figure 12J:
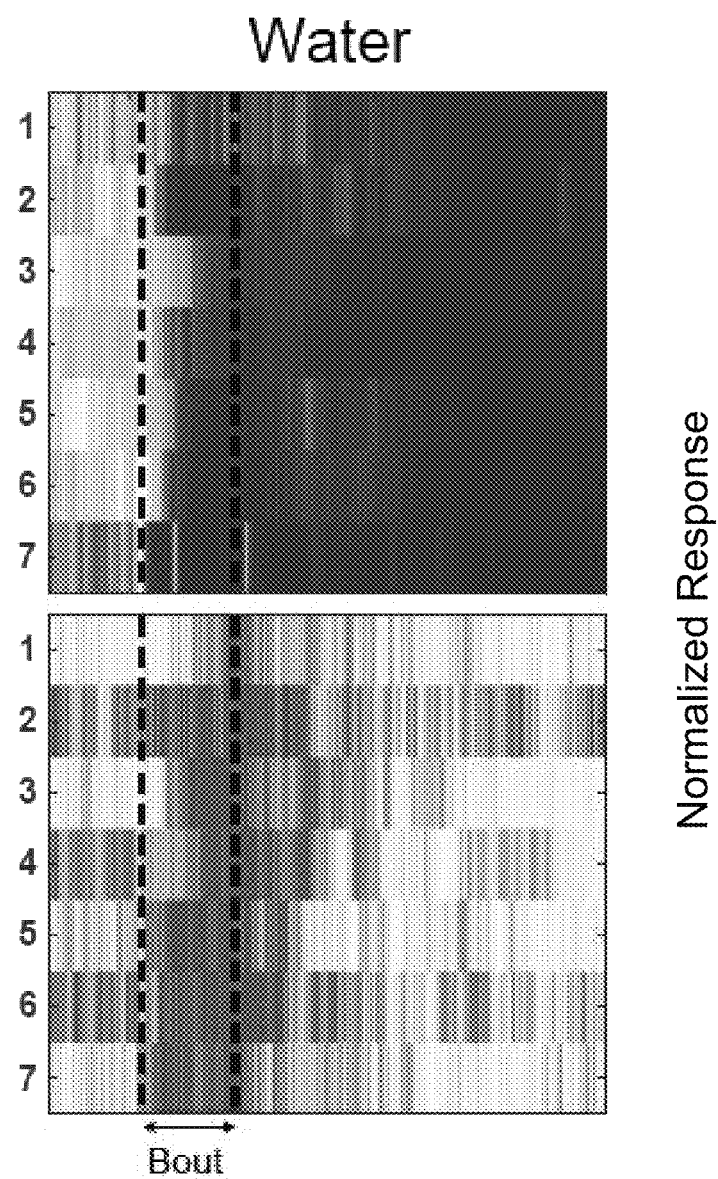
Figure 12K:
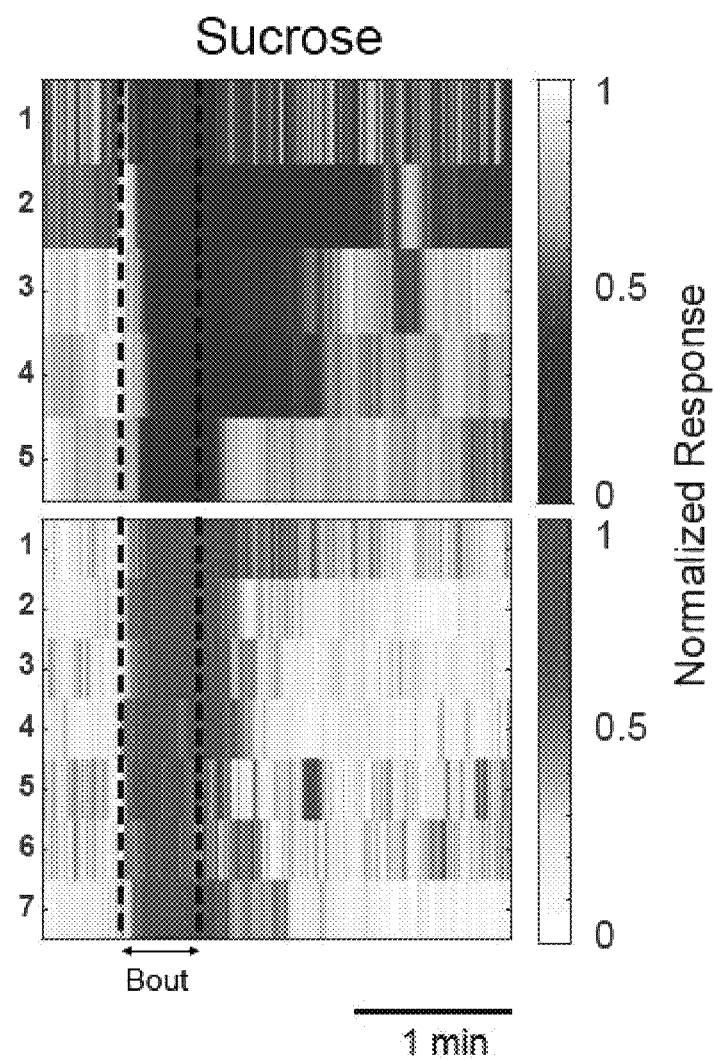
Figures 12L, 12M:
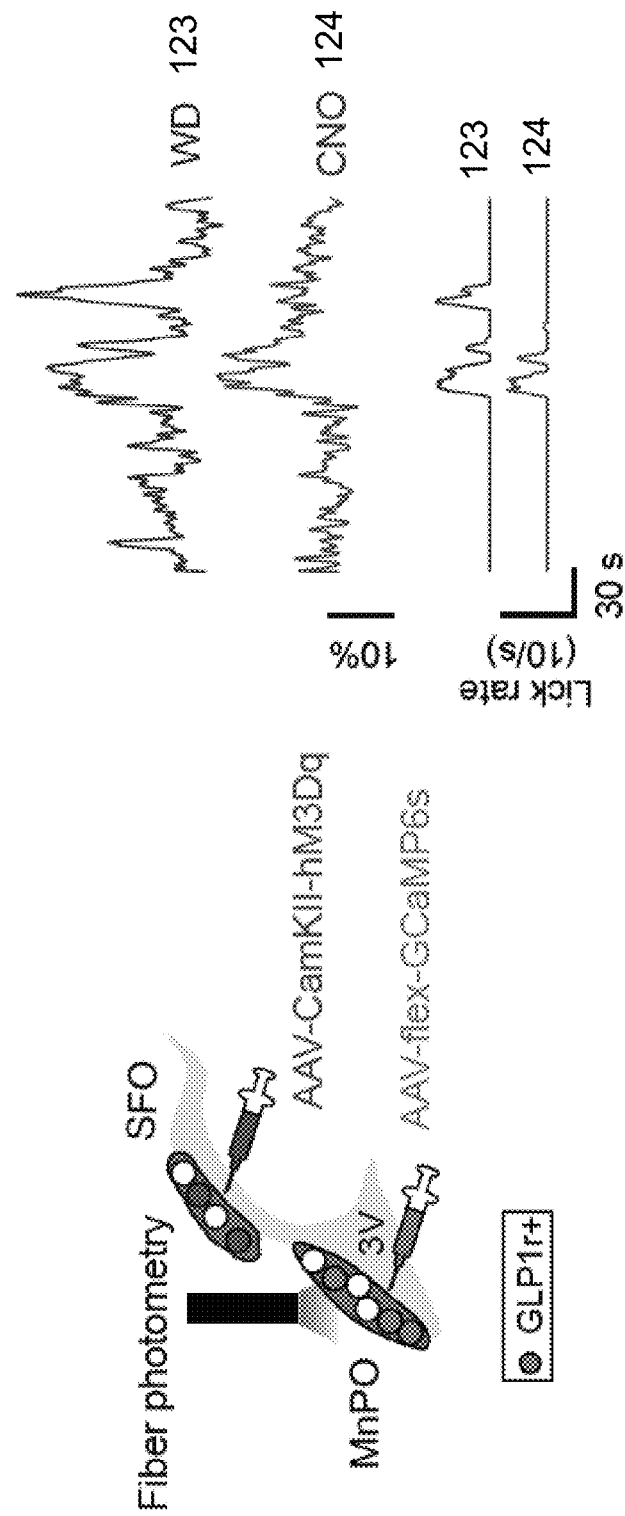
FIGS. 12L-M show that MnPO$^{GLP1r}$ activation is independent of instinctive need. Fiber photometry recording of MnPO$^{GLP1r}$ neurons (FIG. 12L bottom) while activating the SFO$^{nNOS}$ neurons (FIG. 12L top). GCaMP6s was virally expressed in MnPO$^{GLP1r}$ neurons for recording calcium dynamics while activating SFO$^{nNOS}$ neurons by hM3Dq-mCherry under the CamKII promoter (FIG. 12L). Intraperitoneal CNO injection and water deprivation induce water drinking which robustly activates MnPO$^{GLP1r}$ neurons (FIG. 12M), first and second traces from top, respectively). Activity change (Area Under Curve) and lick numbers were quantified for natural thirst 123 and CNO activation 124 (n=5), as shown in FIGS. 12N-O. Statistical significance was analysed with paired two-tailed t-test or Kruskal-Wallis one-way ANOVA test. All error bars show mean ±s.e.m. "123" refers to water deprivation (WD), "124" refers to CNO injection (CNO).
Figure 12N:
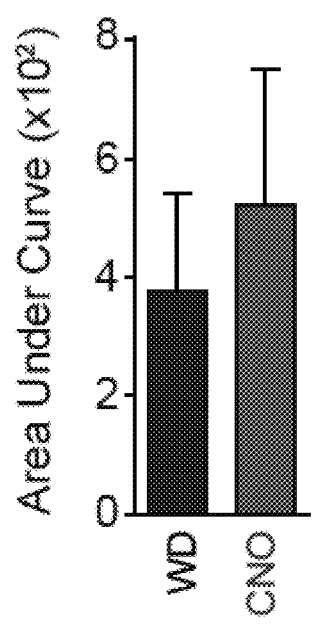
Figure 12O:
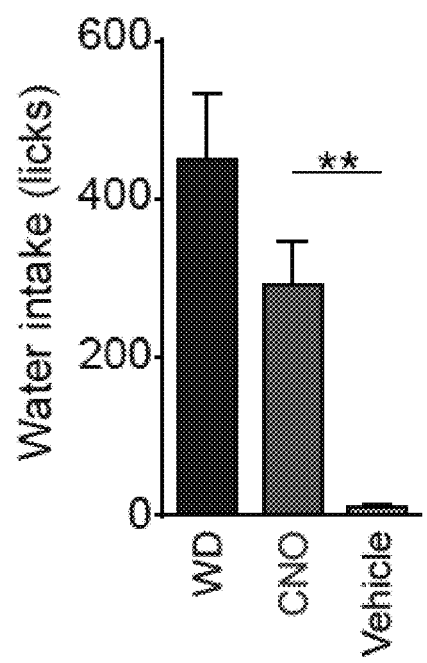

Long-term access assays: Optogenetic Testing—For FIGS. 1L-N and FIGS. 7L-O, satiated mice were given ad libitum access to water for 20 min with photostimulation. Photostimulation was delivered for 1-s followed by 3-s intervals throughout the behavioral sessions. For FIGS. 2J-M and FIGS. 11C-E, mice were given access to water for 20 min after 24 h water-restriction, and photostimulation was delivered for the first 10 min. For feeding assays (FIGS. 2J-M), animals were single-housed in Biodaq cages after 24 h food-restriction, and chow intake was measured for 20 min with or without light stimulation. For acute inhibition experiments, mice were given access to 150 mM NaCl (FIGS. 5D-E, FIGS. 13E-F), water (FIGS. 1L-N, FIGS. 7L-O, FIGS. 13A-D, FIGS. 13G-H) for 20-30 min after 24 h water-restriction or 300 mM sucrose (FIGS. 1L-N, FIGS. 7L-O) after food-restriction. For all acute inhibition experiments, CNO was injected at 10 mg/kg body weight, 30 min prior to the start of the behavior session. For acute activation experiments, CNO was injected at 1 mg/kg body weight (FIGS. 12L-M), 30 min prior to the start of the behavior session. For FIG. 3A, FIGS. 9A-C, and FIG. 13L, water or saline access was provided for 30 min after 24 hours of water restriction. For FIGS. 4A-B, water or HydroGel (ClearH$_2$O) in a cup was provided for 30 min after 24 and 36 hours of water restriction, respectively. The weight of the cup was measured before and after the behavior session. For FIGS. 4K-L, 0.5 pellets of chow was provided for 30 min after 24 h food-restriction. The entire session was recorded using a camera at 30 fps and ingestion episodes were manually annotated.

Salt/Mannitol Loading Experiments: 150 μL/300 μL of 2 M NaCl or 300 μL of 2 M Mannitol was injected intraperitoneally at the end of the acclimatization period. For FIGS. 1P-T and FIGS. 7P-S, CNO or vehicle (water) was injected 10 min prior to NaCl/Mannitol injection.

Brief Access Assays: For optogenetic experiments, behavioral assays were performed essentially as previously described[10]. Satiated animals were tested in a gustometer for 10-15 trials (FIG. 1H and FIGS. 6I-J). The laser pulses were delivered during the first 20 s of the 40-s trial. After the first lick, animals were given access to a water spout for 5 s. For photometry recording (FIG. 3D and FIGS. 12A-C), water-restricted animals were presented with one of the following four stimuli for 30 s: water, isotonic saline, silicon oil, or empty bottle (control). Under food-restricted conditions (FIG. 3G and FIGS. 12D-F), a bottle containing 300 mM sucrose, peanut butter (coated on a spout), or empty bottle was presented for 30 s. To avoid the effect of internal state changes, we used the data from the first stimulus presentation in each session. For testing the effect of temperature (FIGS. 4Q-S), 3 bottles of water at 4° C., room temperature (25° C.) or 37° C. was placed at the start of the acclimatization period (10 min). Each trial was 30 s long with an inter-trial interval of 2 min. For FIGS. 4M-P, water-restricted animals had access to water for 2 s repeated 15 times and 30 s. Each presentation was followed by a 30-s interval.
Fiber Photometry We measured bulk fluorescence signals using fiber photometry as previously described[26]. Briefly, 490 nm and 405 nm LEDs (Thorlabs, M490F1 and M405F1) were collimated and delivered to the brain. The light intensity was kept less than 100 μW during all recordings. The fluorescence signal was then focused onto a femtowatt photoreceiver (Newport, Model 2151). The modulation and demodulation were done with an RP2.1 real time processor (Tucker-Davis Technologies) running custom software. The licks from the lickometer were simultaneously recorded as real-time TTL signals to the RP2.1. Fluorescence changes were analyzed using custom MATLAB (MathWorks) code as described previously[26]. Data were extracted and subjected to a low pass filter at 1.8 Hz. A linear function was used to scale up the 405 nm channel signal to the 490 nm channel signal to get the fitted 405 nm signal. The resultant ΔF/F was calculated as (raw 490 nm signal-fitted 405 nm signal)/(fitted 405 nm signal). For brief access tests, the Area Under Curve (ΣΔFduring) was quantified by integrating the fluorescence signals during the bout. For all bouts, the mean fluorescence for 30 s prior to the first lick was calculated and subtracted from the entire session. ΔF changes ($\Delta F_{post}$-$\Delta F_{pre}$) were calculated by subtracting the mean fluorescence signal during the 2-s period before the first lick from the mean signal during the 2-s at 1 min after the bout. For displaying traces, the fluorescence data was time-binned by a factor of 2.5 times the sampling frequency and down-sampled to 1 Hz. For long-term tests, the Area Under Curve was calculated for 2.5 min after the start of the bout. DF changes were calculated by subtracting the mean signal during the 2-s before the first lick or NaCl injection from the mean signal during the 2-s at 5 or 10 min after the bout (FIGS. 9A-F). For PSTHs (FIGS. 4G-L), the first bout at the start of the session and the last bout within 10 min of access were used. The AUC for the PSTHs were calculated during the first or the last 15 seconds.
Viral Tracing Monosynaptic Rabies Tracing: 150 nL of a mixture of AAV1-CA-FLEX-RG and AAV1-EF1a-FLEX-TVA-mCherry (4:1 ratio) was injected to the target area. Two weeks later, 200 nL of EnvA G-deleted Rabies-eGFP was injected to the same area. The animals were euthanized a week later and their brains collected.

HSV Tracing: 200 nL of a mixture of AAV1-Syn-GCaMP6s-WPRE-SV40 and hEF1-LSL22 mCherry HT (2:5 ratio) was injected to the SFO of Vgat-Cre mice. The GCaMP virus was used to mark the injection site. The animals were euthanized 3 weeks later and their brains collected.

The sections were imaged using a confocal microscope (TCS SP8, Leica) or a slide scanner (VS120, BX61VS-Olympus) at 20×. The slide scanner images were used to count cells using ImageJ. Representative images in FIG.

1B-C, FIG. 2B, FIGS. 10B-G, and FIGS. 10I-K are from the confocal microscope. Regions with an average greater than 10 RV positive cells in all the animals tested were included in the analysis.

Histology

Animals were deeply anaesthetized with $CO_2$ and then transcardially perfused with PBS followed by 4% PFA in PBS (pH 7.4) at 4° C. The brains were extracted and fixed in 4% PFA at 4° C. overnight. 100 mm coronal sections were prepared using a vibratome (Leica, VT-1000s) for antibody staining. The primary antibodies (1:500 dilution) used were—goat anti-c-Fos (Santa Cruz, SC-52G), rabbit anti-nNOS (Santa Cruz, sc-648), rabbit anti-GAD65+GAD67 (Abcam, ab183999), chicken anti-GFP (Abcam, ab13970) and rat anti14 mCherry (Thermo Fisher, M11217). After PBS wash for 3 times, the sections were incubated with secondary antibodies (1:500 dilution) in blocking buffer for 4 hours. The GAD65/67 primary/secondary antibody incubation solution was prepared without detergent. FISH was carried out by using the RNAscope fluorescent multiplex kit (Advanced Cell Diagnostics) in accordance to the manufacturer's instructions. GLP1r/Ai9 mice were used with probes targeted to tdTomato and GLP1r.

RNA-Seq Analysis

The dorsal LT (dLT) in Vgat-Cre/Ai9 mice were dissected under a fluorescence microscope. To minimize contamination from other tissues, the LT tissue containing the SFO and dorsal MnPO were peeled off. For non-LT control, we dissected small tissues of the cortex from the same animals. These samples were dissociated into single cells using Papain Dissociation System (Worthington), labelled with DAPI and the tdTomato3 positive neurons sorted using a flow cytometer (MoFlo Astrios, Beckman Coulter). RNA was extracted using a PicoPure RNA isolation kit (Applied Biosystems) and complementary DNA prepared using an Ovation RNA-seq V2 kit (Nugen). Relative gene expression (FIG. 2C) was calculated as a ratio of FPKM of the dLT to FPKM of the cortex. The genes with FPKM<=0.1 in the cortex were omitted for plotting.

Slice Electrophysiology

Procedures for preparation of acute brain slices and recordings with optogenetic stimulations were similar to those described previously[10],[36]. After decapitation, the brain was removed and immersed in ice-cold solution. Coronal slices (300 mm) were cut using a vibratome (VT-1200s, Leica) and moved into HEPES-holding solution (NaCl 92, KCl 2.5, $NaH_2PO_4$ 1.2, $NaHCO_3$ 30, HEPES 20, glucose 25, Na-ascorbate 5, Thiourea 2, Na14 pyruvate 3, $MgSO_4$ 2, $CaCl_2$ 2, pH 7.35). The slices were allowed to recover at 33° C. for 30 min and then held at room temperature (~25° C.) until use.

While recording, slices were perfused continuously (~2 mL/min) with artificial cerebrospinal fluid (ACSF-NaCl 124, KCl2.5, $NaH_2PO_4$ 1.2, $NaHCO_3$ 24, glucose 25, $MgSO_4$ 1, $CaCl_2$ 2) at 25° C. Neurons were visualized and targeted using an upright IR19 DIC microscope (BX51WI, Olympus). Whole-cell recordings were achieved using glass pipettes with an impedance of 4 to 6 MΩ when filled with intracellular solution (for voltage clamp, CsCl 145, NaCl 2, HEPES 10, EGTA 0.2, QX-314 Chloride 5, Mg-ATP 4, Na-GTP 0.3, pH 7.25; for current clamp, K-gluconate 145, NaCl 2, KCl4, HEPES 10, EGTA 0.2, Mg-ATP 4, Na-GTP 0.3, pH 7.25). Electrical signals were sampled at 20 kHz and filtered at 2.9 KHz using an EPC 10 system (HEKA Elektronik). To evaluate post-synaptic currents (PSCs) evoked by light pulses, the membrane potential of $SFO^{nNOS}$ (transduced with CamKII-mCherry/eYFP) or $SFOn^{non-nNOS}$ neurons were held at −60 mV. Light pulses were generated by a mercury lamp, filtered by an optical filter (Chroma) and controlled by an electronic shutter driver (VCM-D1, UNIBLITZ). 2-ms light pulses were delivered at 1 Hz for 4 times followed by 4 s interval. We repeated this stimulus cycle for 20 times. In order to confirm the PSCs recorded were GABAergic, picrotoxin (150 μM) was applied through the bath in part of the experiments. To confirm glutamatergic PSCs, CNQX (10 mM) and DL-APV (25 mM) were applied through the bath. Mono-synaptic connection was defined by synaptic IPSCs/EPSCs with latency less than <16.4 ms. For hM4Di experiments, current clamp recordings were done by applying a constant supra-threshold current injection to produce tonic action potentials. CNO (~6 μM) was applied by a puff (30 s) from another glass pipette placed ~50 μm from the recorded cell.

Plasma $Na^+$ and Osmolality Measurements

After the injection of 150 mL 2M NaCl or 300 μL 2M Mannitol, trunk blood was collected from wild-type animals. Plasma was then extracted after centrifugation at 1500 g for 20 minutes. Plasma osmolality was measured using a vapor pressure osmometer (Vapro 5520). Plasma $Na^+$ concentration was measured using Dionex (Thermo) ICS 2000.

Intra-Cranial Drug Delivery 100 ng of Exendin-4 (Sigma Aldrich) dissolved in 1 μL of ACSF was delivered by a custom-made cannula and tubing (PlasticsOne) connected to a Hamilton syringe driven by a pump (NewEra PumpSystems) at 100 nL/min into the MnPO of water deprived animals under head-fixed conditions. Two minutes after infusion, freely-moving animals were given access to water for the next 45 minutes. The cannula position was verified by infusing Exendin-4-FAM (Anaspec) conjugate before euthanasia. ELISA Total Plasma GLP1 was measured using EZGLP1T-36k kit (Millipore) as described previously[37]. Briefly, after blood was collected in EDTA-coated tubes, plasma was isolated by centrifugation at 1500 g for 20 min. Samples were then kept at −80° C. until measurement. For food-repleted (FD+F) and water-repleted (WD+W) conditions, animals were given access to Ensure for 30 min or water for 5 min, respectively.

Statistics

All statistical analyses were done using Prism (GraphPad). We either used a two-tailed Mann-Whitney U-test, Kruskal-Wallis one-way ANOVA, or paired t-test depending on the experimental paradigm. *$P<0.05$, $P<0.01$, *$P<0.001$. Data sheets with the analysis of statistical tests from Prism reporting estimates of variance within each group, comparison of variances across groups are available on request. No statistics to determine sample size, blinding or randomization methods were used. Representative data was based on at least 3 independent observations. Viral expression and implant placement was verified by histology before animals were included in the analysis. These criteria were pre-established.

Example 1

This example describes the hierarchal organization of neurons in the lamina terminalis.

We focused on $SFO^{nNOS}$ neurons and their synaptic connections to dissect genetically-defined thirst circuits using neural manipulation, tracing, and in vivo fiber photometry approaches. On the one hand, we mapped downstream circuits of $SFO^{nNOS}$ neurons to reveal how the brain translates the homeostatic need for water into behavioural output. On the other hand, we identified a specific neural circuit upstream of SFO$^{nNOS}$ neurons that monitors real-time drinking behaviour and provides inhibitory inputs to thirst circuits.

Figure 1A:
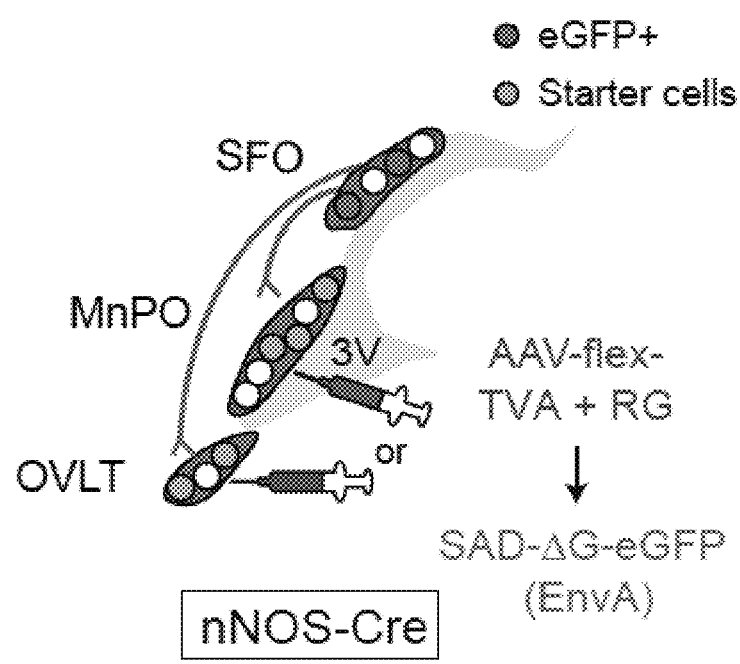
Figure 1D:
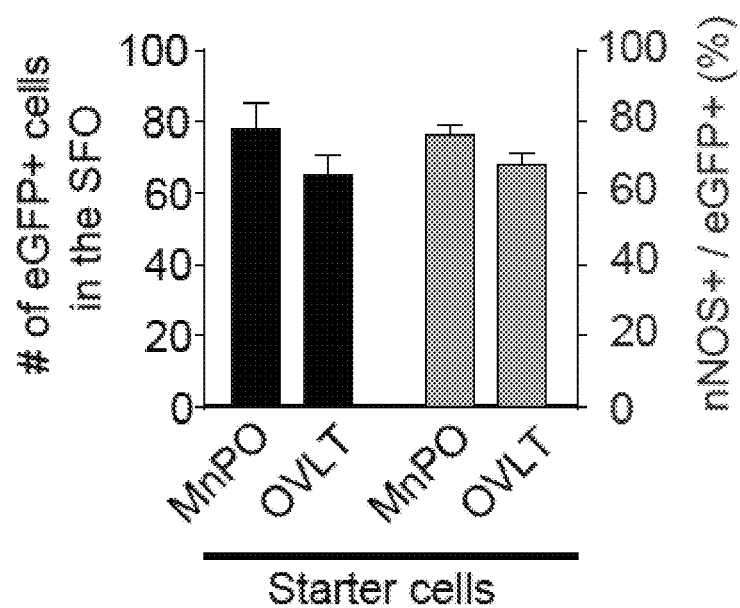
FIG. 1D shows quantification of the number of eGFP-positive neurons (black two bars on left;) in the SR), and overlap between eGFP and nNOS signals (gray two bars on right, n=7 and 5 mice for MnPO and OVLT, respectively). Schematics of functional epistasis analyses are shown in FIGS. 1E-F. AAV-flex-Casp3-TEVp was targeted to the MnPO or OVLT for ablation, and AAV-DIO-ChR2-eYFP was targeted to the SFO for photostimulation in nNOS-Cre animals (FIG. 1E). Alternatively, $MnPO^{nNOS}$ neurons were photostimulated in the absence of $SFO^{nNOS}$ neurons (FIG. 1F).
Figures 6A, 6B:
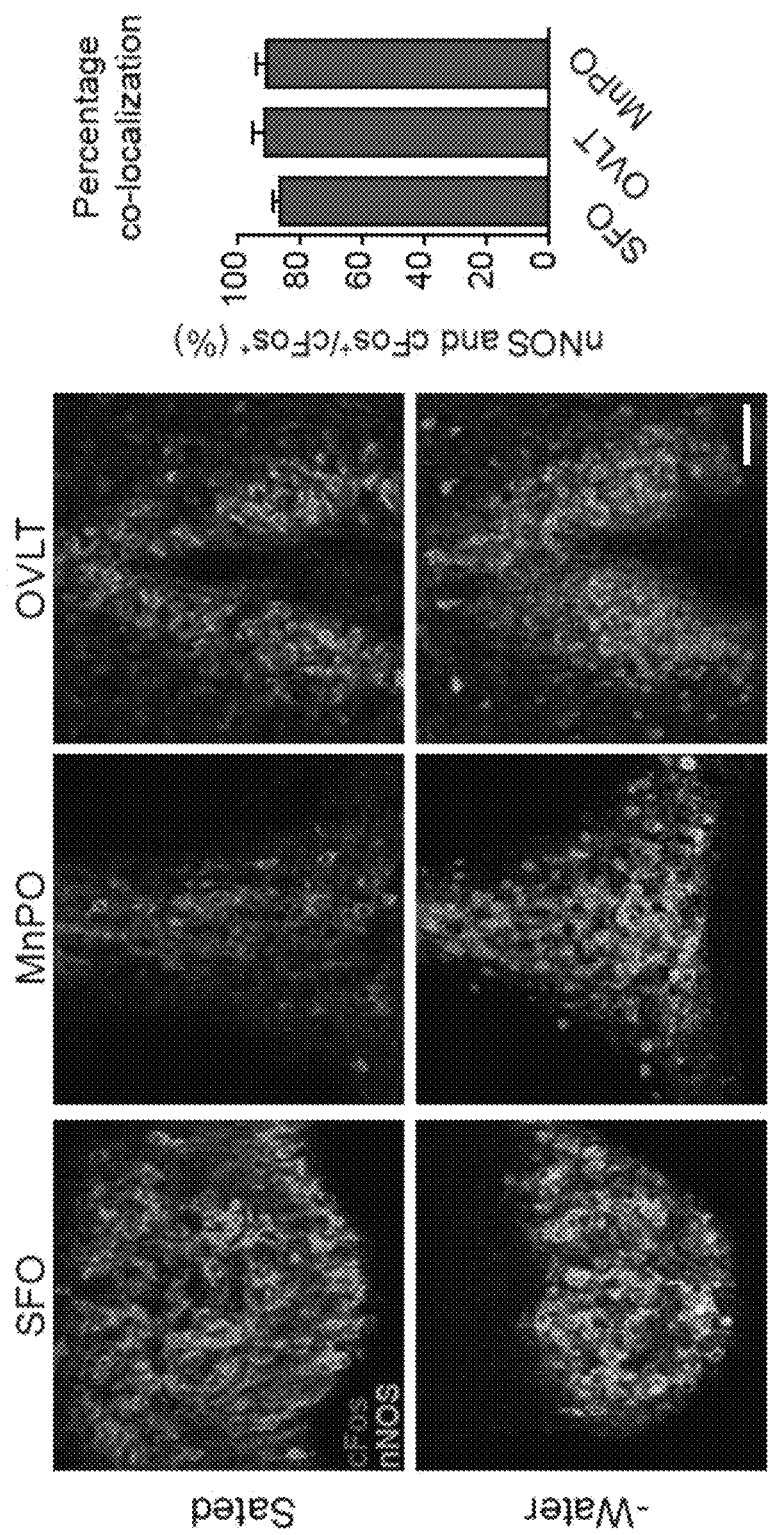
Figure 6C:
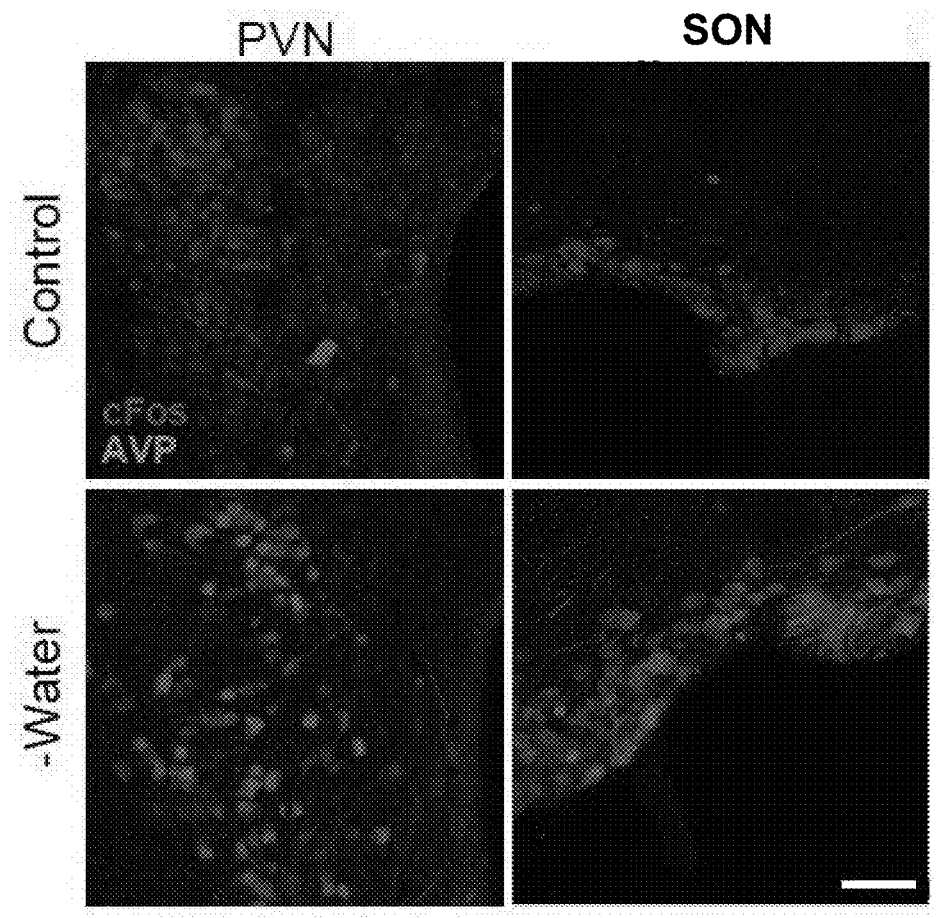
Figures 6D, 6E:
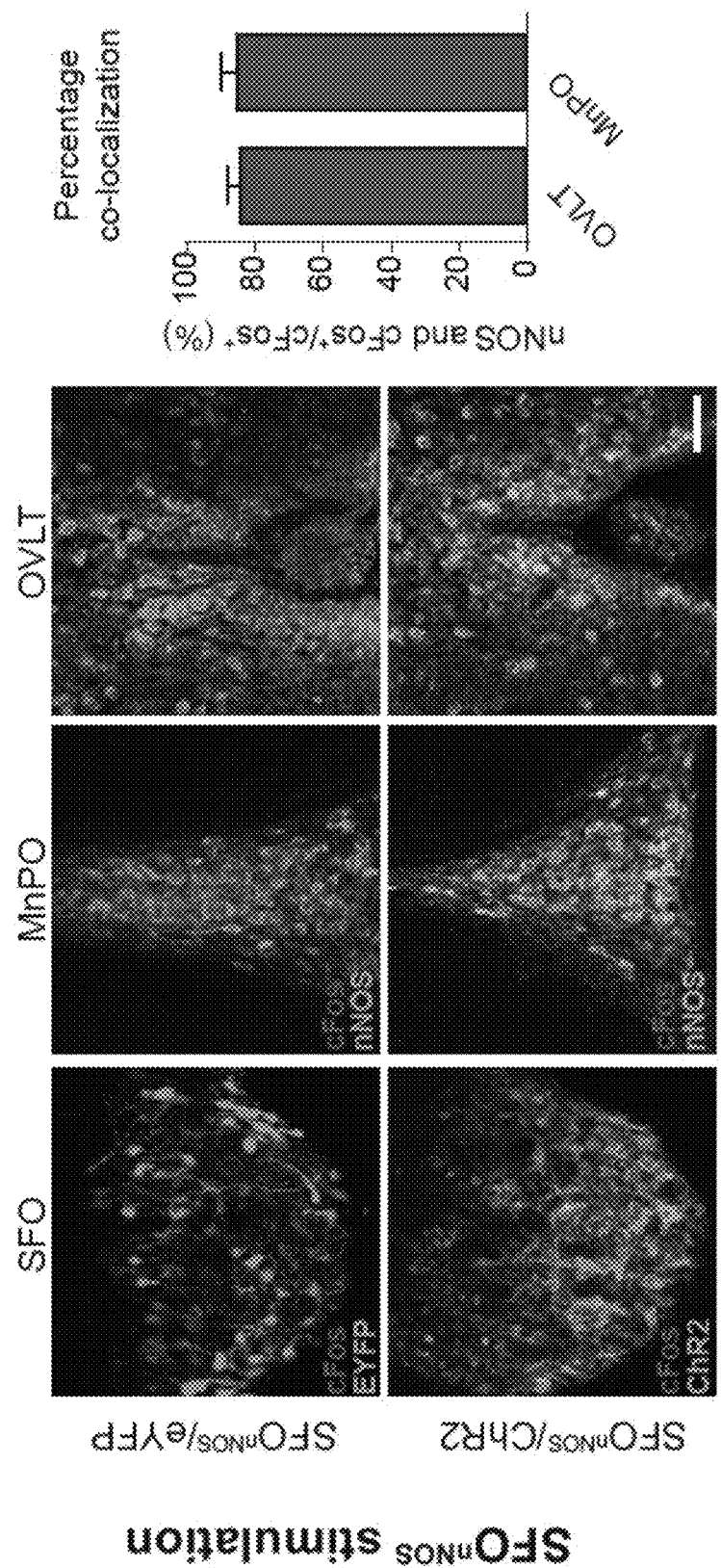
Figure 6F:
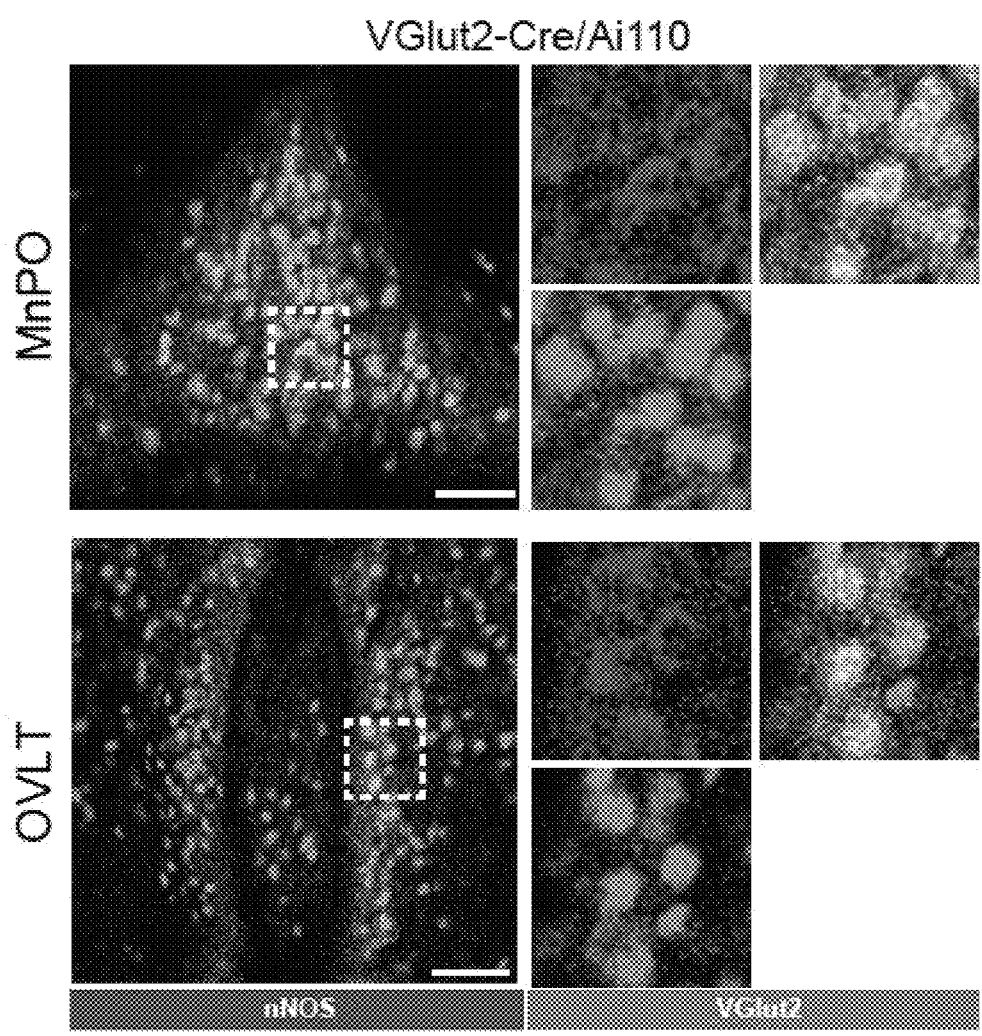
Figure 6G:
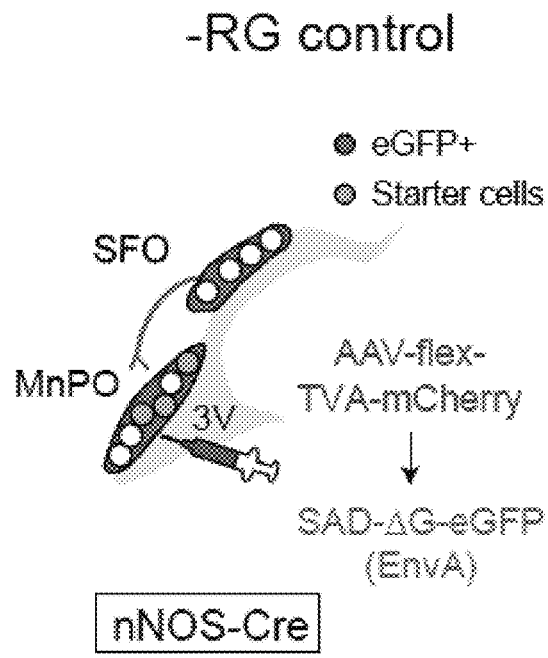
Figure 6H:
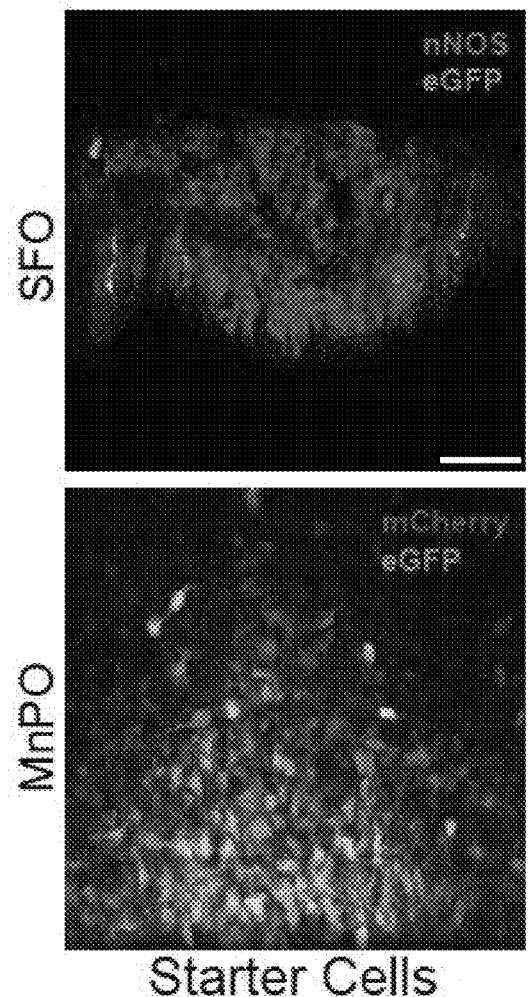

SFO$^{nNOS}$ neurons project their axons to other nuclei of the LT (OVLT and MnPO)[8],[21], as well as the paraventricular and the supraoptic nuclei that contain vasopressin-expressing neurons[10]. These axonal projections and their downstream neurons define a framework of circuit elements that control behavioral and hormonal outputs[22]. To identify genetically-defined SFO$^{nNOS}$ downstream populations that regulate drinking, we employed optogenetics combined with monoynaptic rabies tracing. Water-restriction induces robust c-Fos expression in the SFO and putative downstream regions (FIGS. 6A-E). In the MnPO and OVLT, essentially all the c-Fos signals overlapped with nNOS-expressing excitatory neurons (MnPO$^{nNOS}$ and OVLT$^{nNOPS}$; FIGS. 6A-C and FIG. 6F). Similar results were obtained when we specifically photostimulated SFO$^{nNOS}$ neurons by expressing channelrhodopsin (ChR2) using adeno-associated virus (AAV-DIO-ChR2) in nNOS-Cre mice (FIGS. 6D-E). Without being limited by theory, these data suggest that MnPO$^{nNOS}$ and OVLT$^{nNOS}$ neurons are putative downstream populations of SFO$^{nNOS}$ neurons. We next examined synaptic connectivity by retrograde monosynaptic tracing from MnPO$^{nNOS}$ and OVLT$^{nNOS}$ neurons using modified rabies virus (RV-SAD-AG-eGFP, FIGS. 1A-C)[23]. In both cases, we found strong RV-eGFP signals in the SFO co-localized with nNOS expression (70-80%), validating direct connections of the SFO$^{nNOS}$ population with its putative downstream neurons (FIG. 1D and FIGS. 6G-H). Moreover, photostimulation of ChR2-expressing MnPO$^{nNOS}$ or OVLT$^{nNOS}$ neurons selectively induced water drinking in satiated animals (FIGS. 6I-J). These studies demonstrated that SFO$^{nNOS}$ neurons send monosynaptic excitatory inputs to the MnPO$^{nNOS}$ and OVLT$^{nNOS}$ populations, each of which orchestrates water drinking.

Figure 1E:
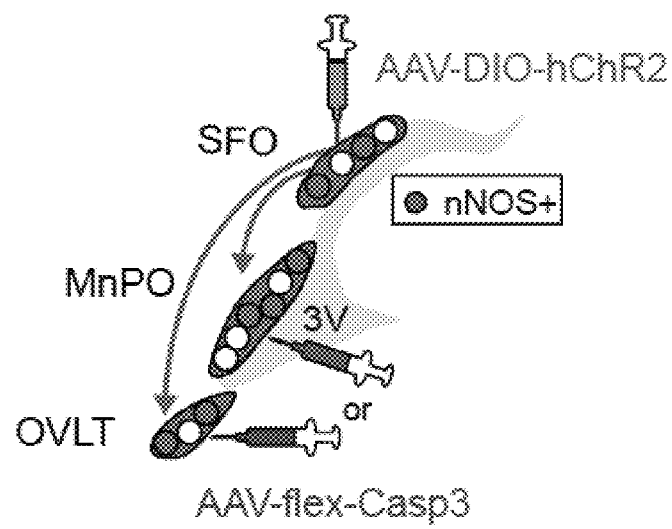
Figure 1F:
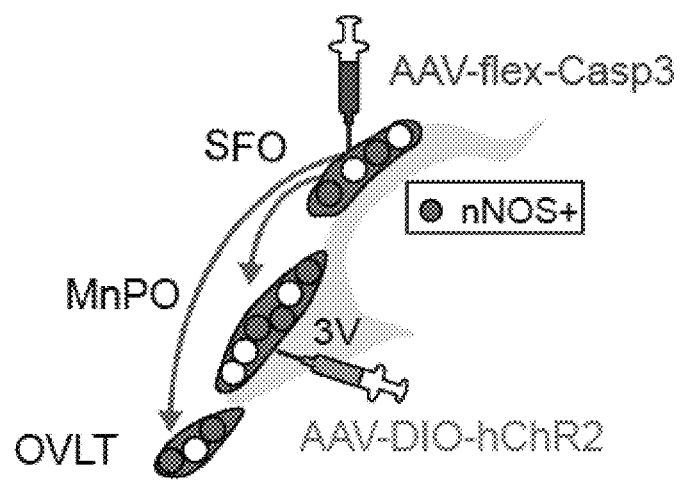
Figure 1G:
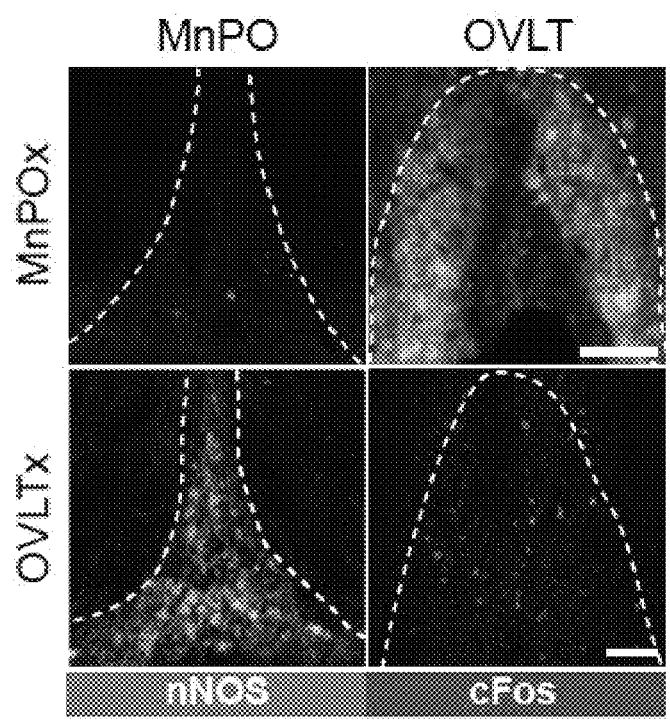
FIG. 1G shows that Casp3-TEVp eliminates nNOS-expressing neurons (green staining seen in lower left panel, but apparently absent in upper left panel) in the MnPO (93.2±4.4%, n=4) and OVLT (90.6±3.0%, n=6). c-Fos expression by the stimulation of $SFO^{nNOS}$ neurons is shown (red staining seen in upper right and lower left panels; sparse red staining seen in lower right panel).
Figure 1J:
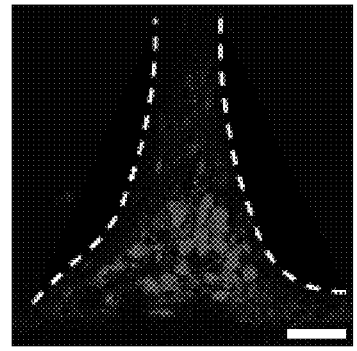
Figure 1K:
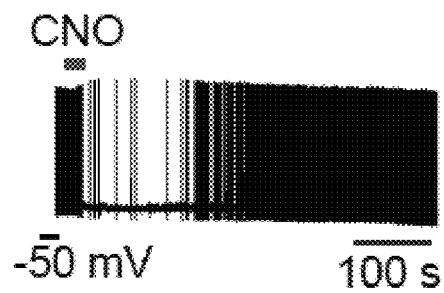
Figures 1L, 1M, 1N:
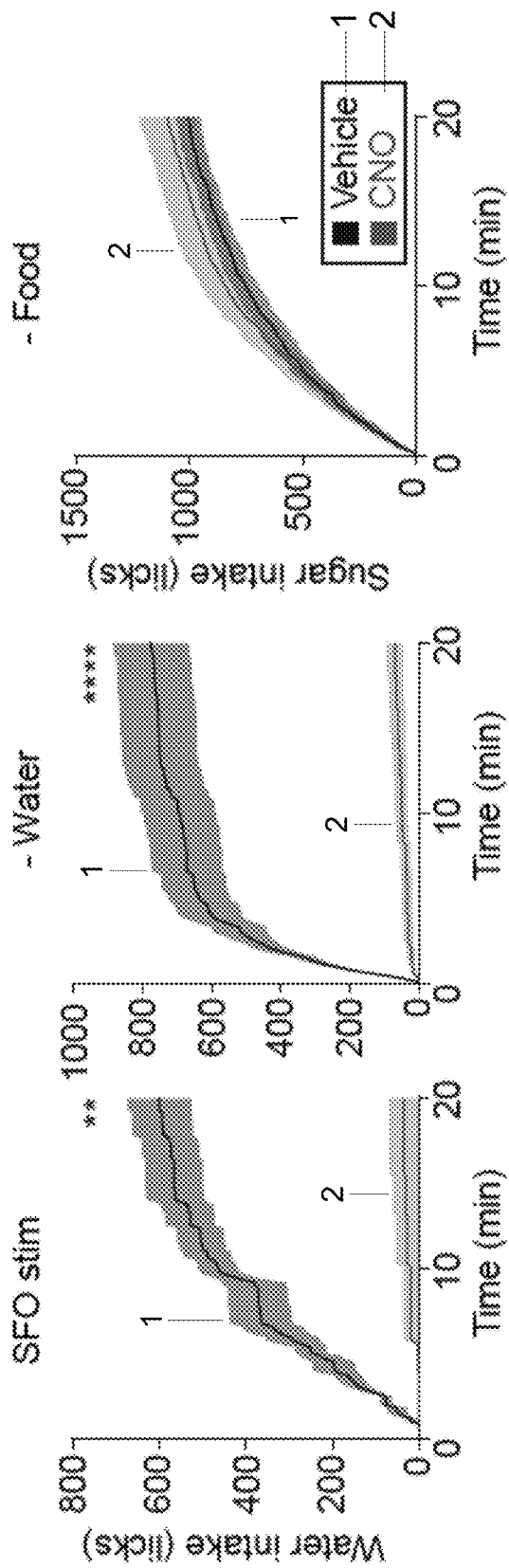
FIGS. 1L-N show cumulative water intake in $SFO^{nNOS}$-stimulated (FIG. 1L, n=5) or water-restricted animals (FIG. 1M, n=10 for CNO and n=9 for vehicle), and sucrose (300 mM) intake in food-restricted animals (FIG. 1N, n=10 for CNO and n=9 for vehicle).
Figure 1O:
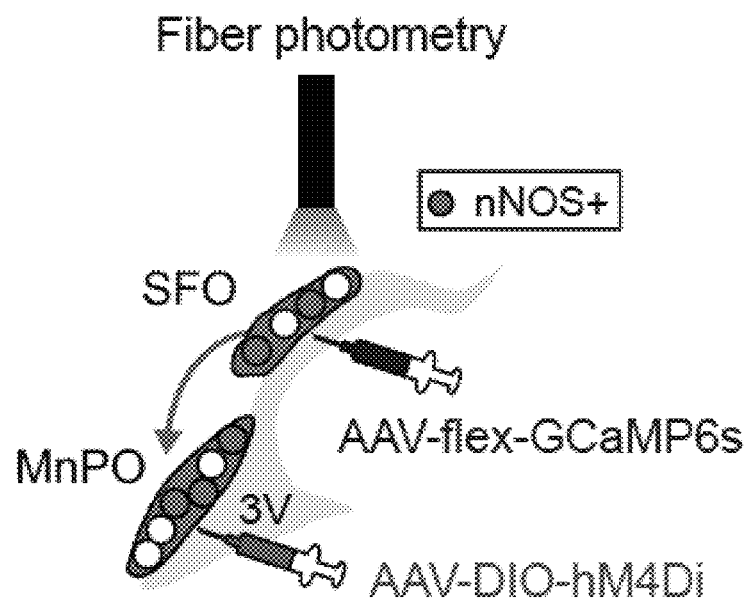
FIG. 1O shows fiber photometry of $SFO^{nNOS}$ neurons. GCaMP6s was virally expressed in $SFO^{nNOS}$ neurons for recording calcium dynamics while inhibiting $MnPO^{nNOS}$ neurons by hM4Di-mCherry.
Figure 1P:
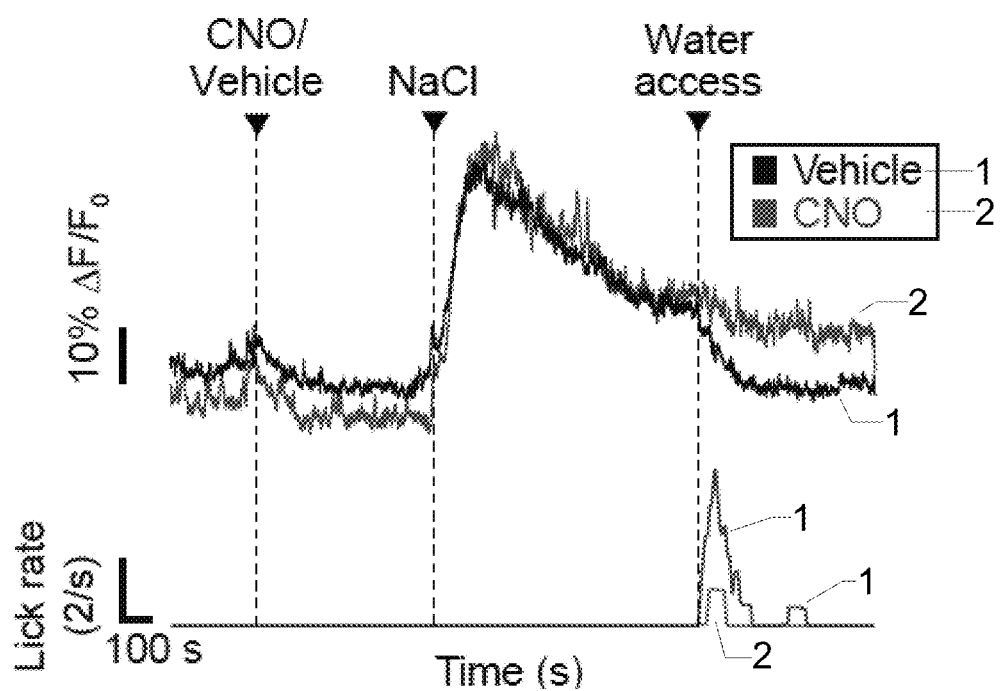
Figure 7C:
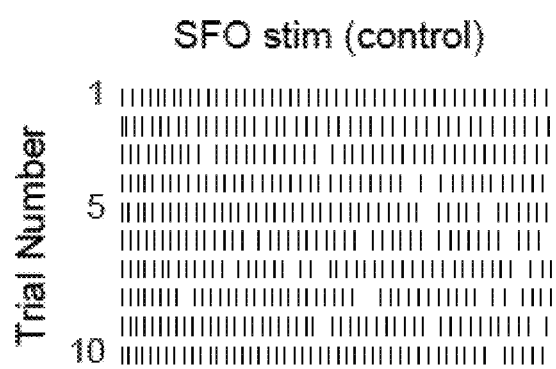
Figure 7D:
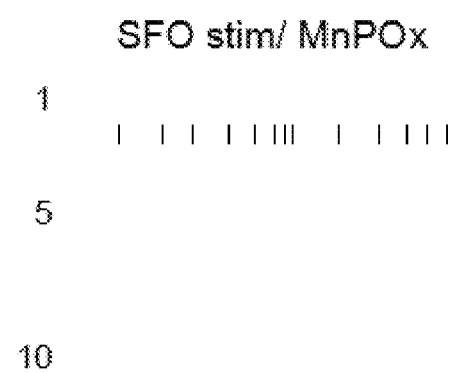
Figure 7E:
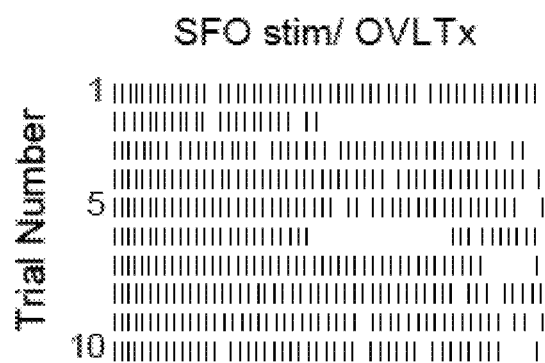
Figure 7F:
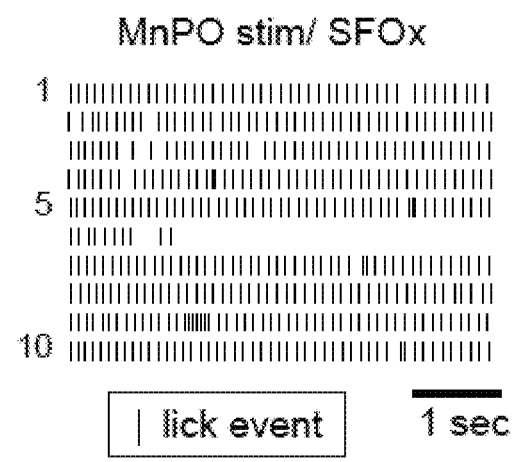
Figure 7L:
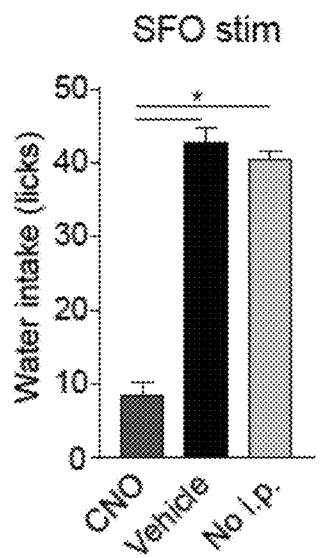
Figure 7L:
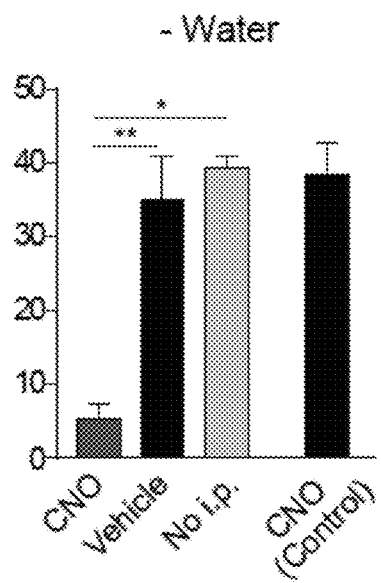
Figure 7L:
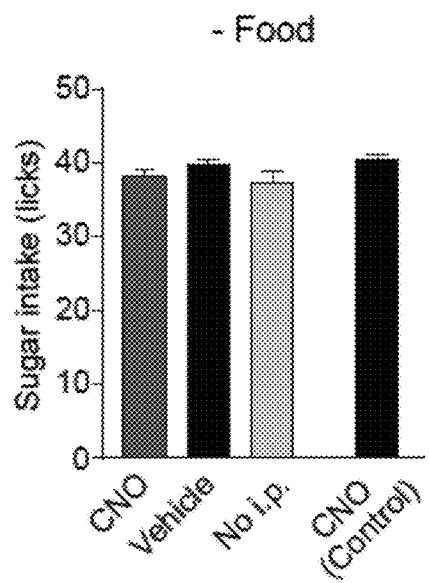
Figure 7L:
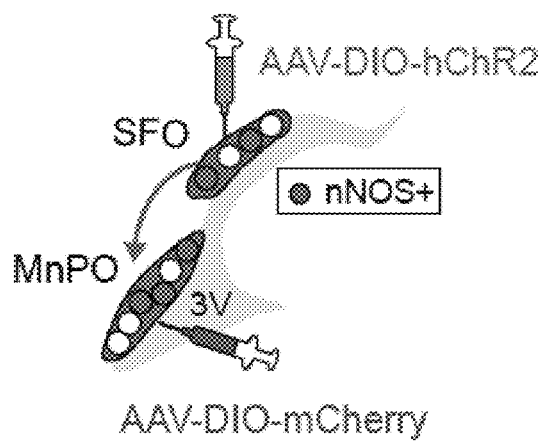
Figure 8B:
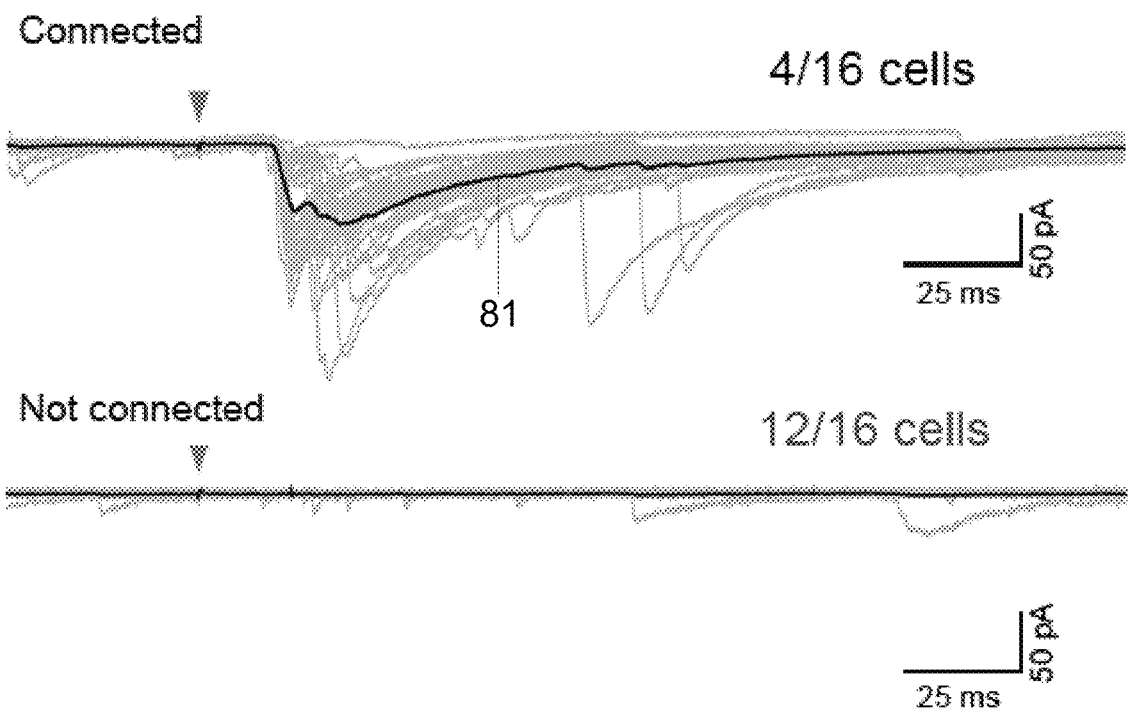
Figure 8C:
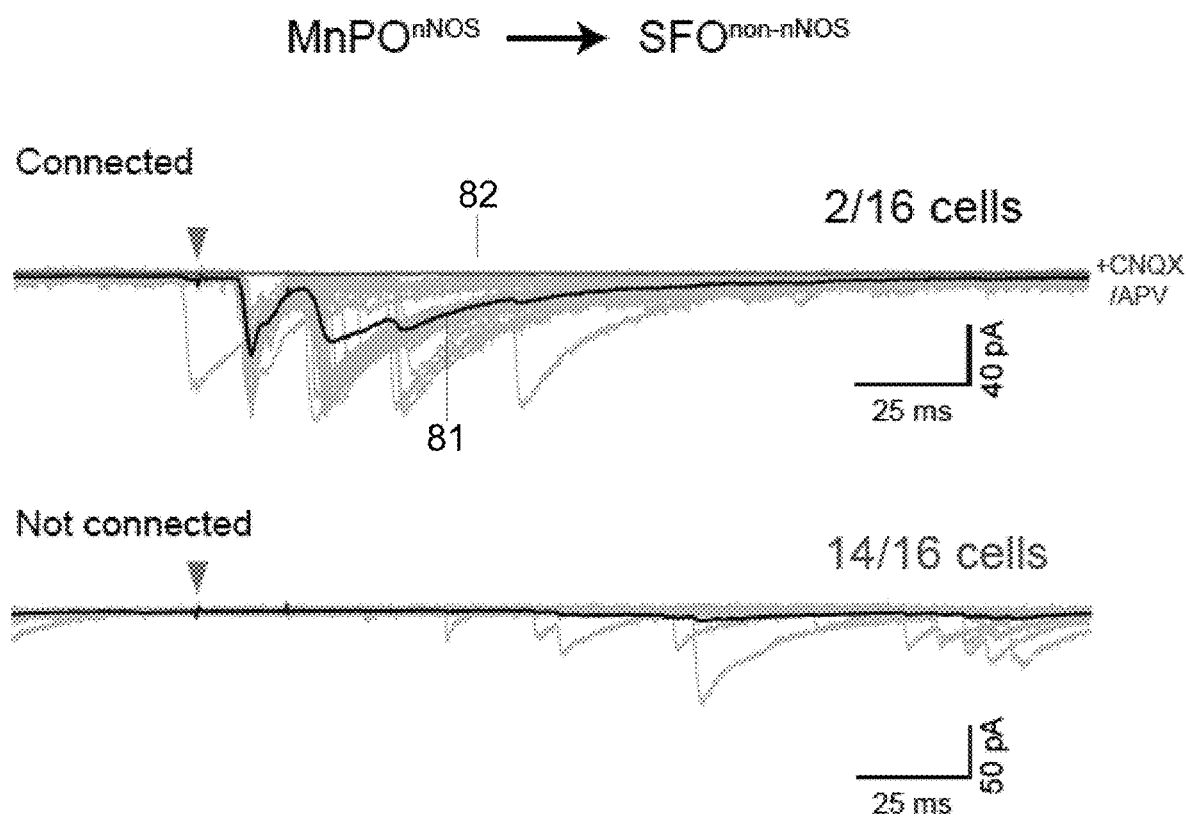
Figure 8D:
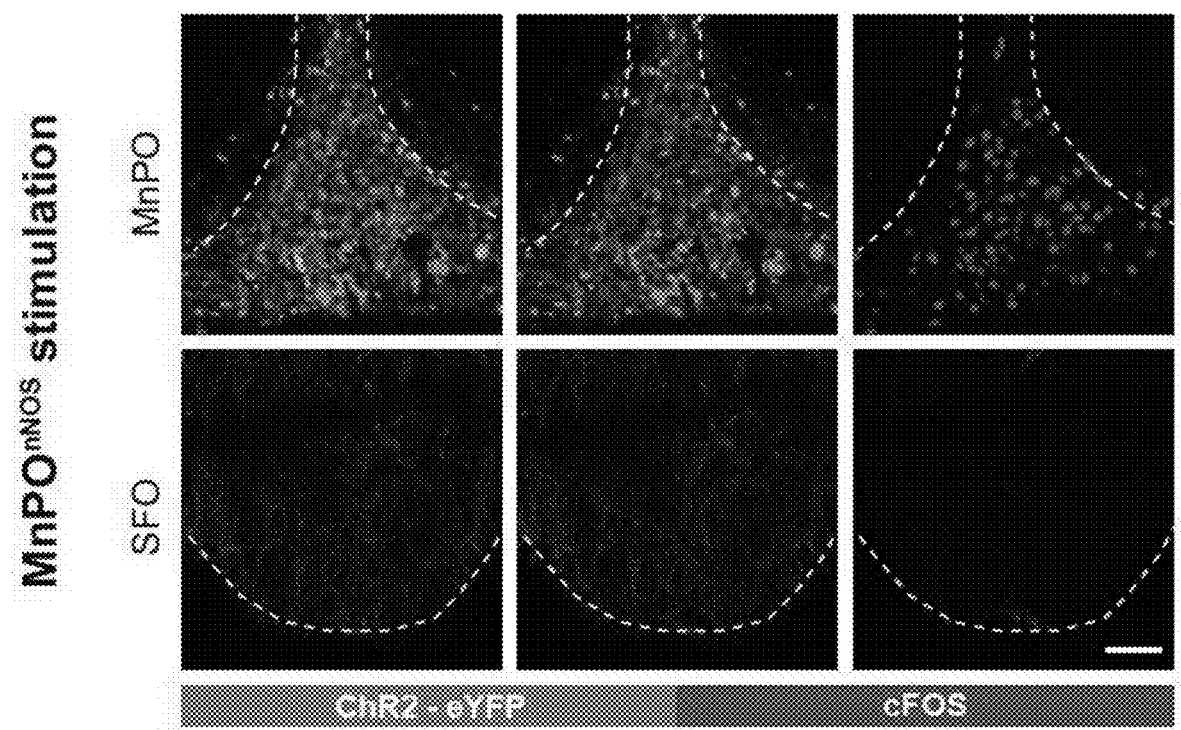
Figure 9A:
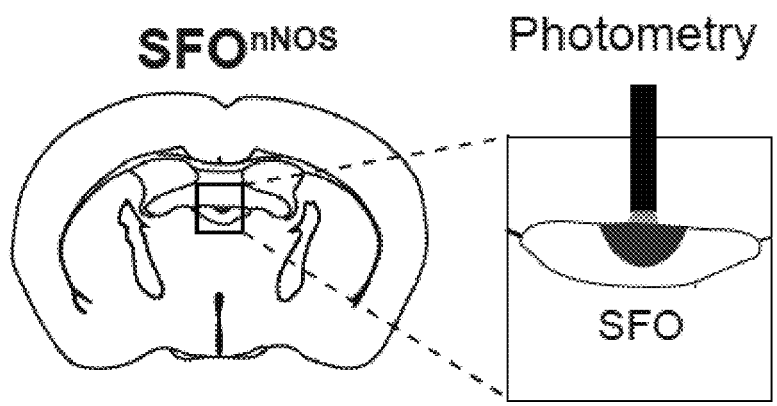
Figure 9B:
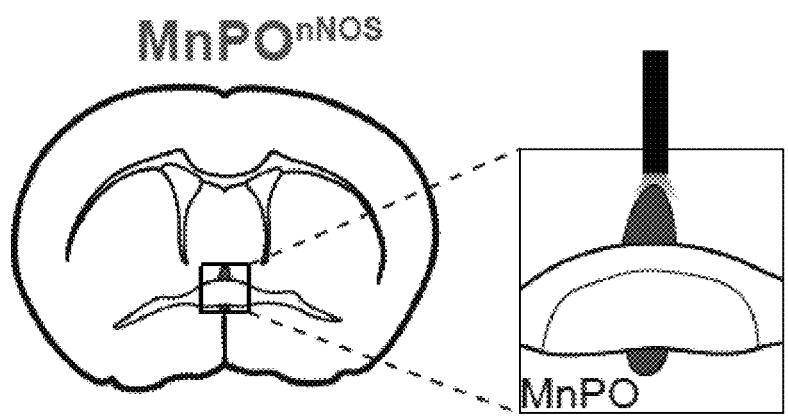
Figure 9C:
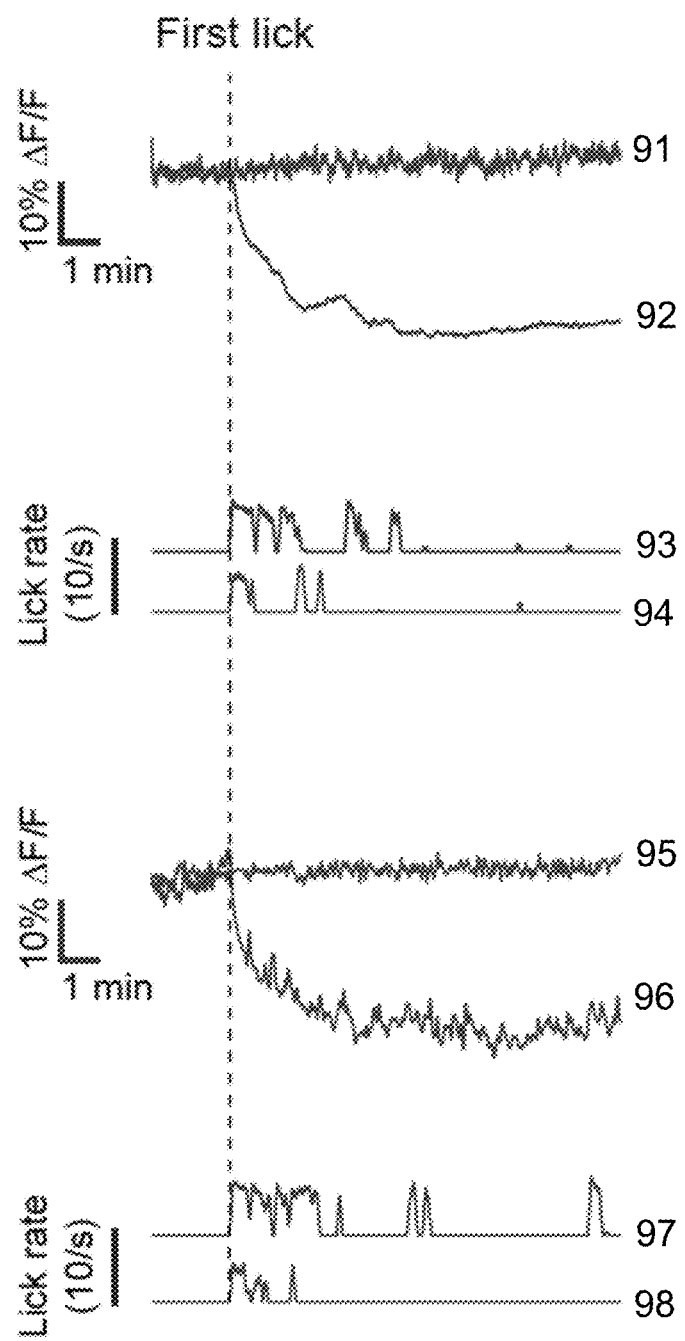
Figure 9D:
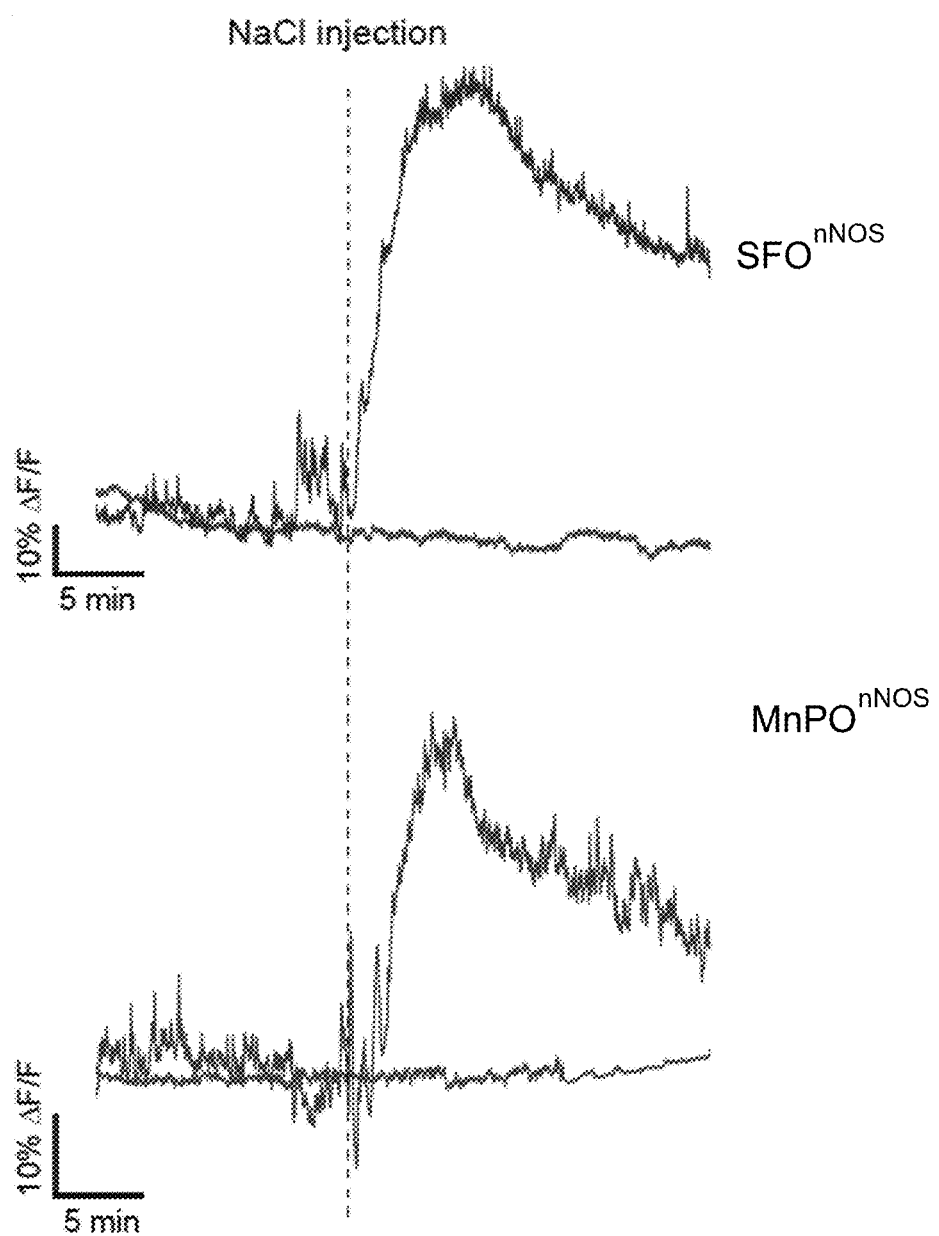

To further dissect the circuit architecture that processes the internal need for water, we performed neural epistasis analysis for the LT circuits by loss-of-function manipulation (FIGS. 1E-F). Without being limited by theory, we reasoned that if SFO$^{nNOS}$ and its downstream populations redundantly encode thirst in parallel, then the ablation of one population should have minor effects on drinking. Alternatively, if the circuit is organized in a hierarchical fashion where a specific population is required, eliminating such a downstream population is expected to abolish SFO$^{nNOS}$-stimulated drinking. To test these ideas, we expressed Caspase (AAV-flex-Casp3)[24] in the MnPO, OVLT or SFO of nNOS-Cre animals (FIGS. 1E-F). Expressing Casp3 resulted in specific and near-complete ablation of nNOS-expressing neurons of a given nucleus (FIG. 1G and FIGS. 7A-B). In OVLT$^{nNOS}$-ablated and control animals, photostimulation of SFO$^{nNOS}$ neurons triggered robust drinking (FIG. 1H and FIGS. 7C-F). In contrast, ablating MnPO$^{nNOS}$ neurons drastically suppressed SFO$^{nNOS}$-stimulated water intake (FIG. 1H and FIGS. 7C-F, MnPOx). We also found that the MnPO$^{nNOS}$ neurons play an important role for drinking evoked by OVLT$^{nNOS}$ neurons. Photostimulation of ChR2-expressing OVLT$^{nNOS}$ neurons induces robust drinking (FIGS. 7G-H). This drinking behaviour was significantly attenuated after ablating MnPO$^{nNOS}$, but not SFO$^{nNOS}$ neurons (FIGS. 7G-H). Without being limited by theory, these results suggest that MnPO$^{nNOS}$ neurons are essential neural substrates of the LT to produce the behavioral output. Thus, stimulating the MnPO$^{nNOS}$ population after killing their upstream SFO$^{nNOS}$ or both SFO$^{nNOS}$/OVLT$^{nNOS}$ neurons should trigger robust drinking (FIGS. 1E-F). As hypothesized, the ablation of these populations had no impact on drinking when MnPO$^{nNOS}$ neurons were directly photostimulated (FIG. 1H and FIGS. 7C-F, SFOx, SFOx/OVLTx). Similar results were obtained with chemogenetic acute silencing using hM4Di[25], a synthetic GPCR. In brain slices, a brief application of its ligand, CNO, strongly suppressed the firing of hM4Di-expressing MnPO$^{nNOS}$ neurons (FIGS. 1I-K). In awake animals, acute inhibition of MnPO$^{nNOS}$ neurons severely suppressed water consumption both in water-restricted and SFO$^{nNOS}$-stimulated animals (FIGS. 1L-N and FIGS. 7I-K). However, the same CNO injection did not decrease sugar (300 mM sucrose) consumption in food-restricted animals (FIGS. 1L-N and FIGS. 7I-O).

Importantly and unexpectedly, silencing MnPO$^{nNOS}$ neurons did not compromise the osmosensory function of the SFO$^{nNOS}$ population. We used fiber photometry[26] in awake-behaving animals that express the GCaMP6s calcium indicator in SFO$^{nNOS}$, and hM4Di in the MnPO$^{nNOS}$ neurons (FIG. 10). We showed that calcium increases in SFO$^{nNOS}$ neurons by NaCl— and mannitol-induced osmotic stress were unaffected after inhibiting MnPO$^{nNOS}$ neurons by CNO, whereas it intensely suppressed drinking responses (FIGS. 1P-T and FIGS. 7P-T). In support of these data, our electrophysiological recording demonstrated that most SFO neurons do not receive monosynaptic input from MnPO$^{nNOS}$ neurons (FIGS. 8A-D).

Taken together, our results show that thirst neurons in the LT form a hierarchical circuit organization, and that the MnPO$^{nNOS}$ population is required for processing signals from SFO$^{nNOS}$ neurons to coordinate drinking.

Example 2

This example shows that GLP1r-positive GABAergic neurons in the MnOP are a major source of inhibitory input to the SFO.

Figure 2A:
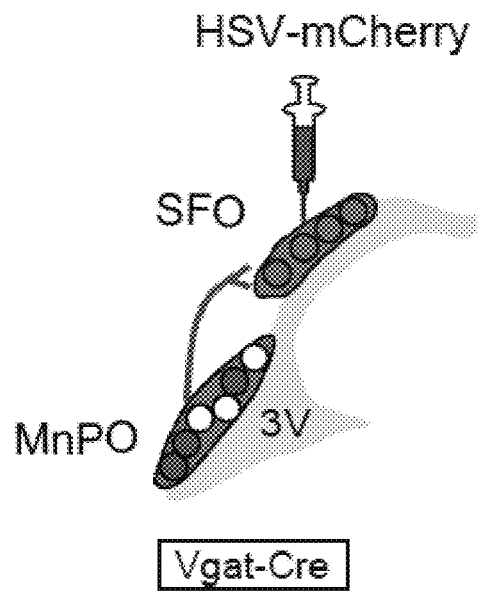
Figure 2B:
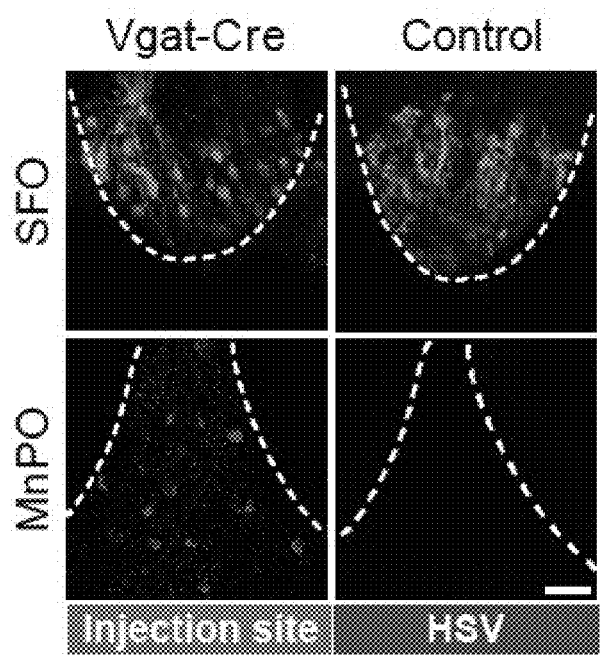
Figure 10A:
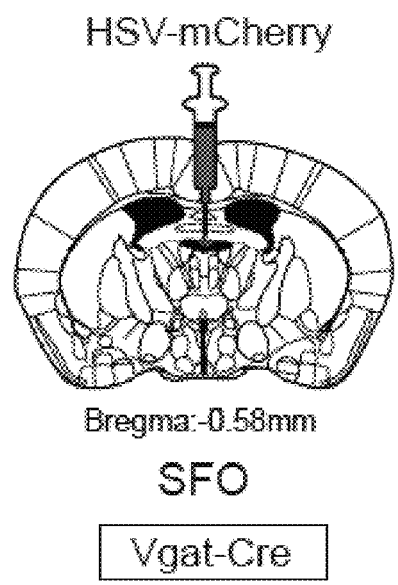
Figure 10B:
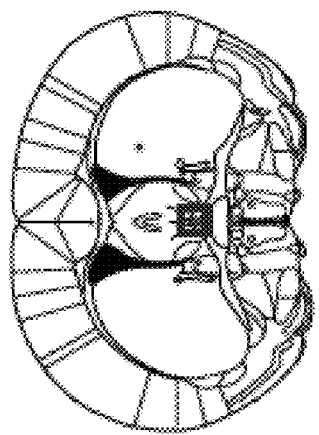
Figure 10B:
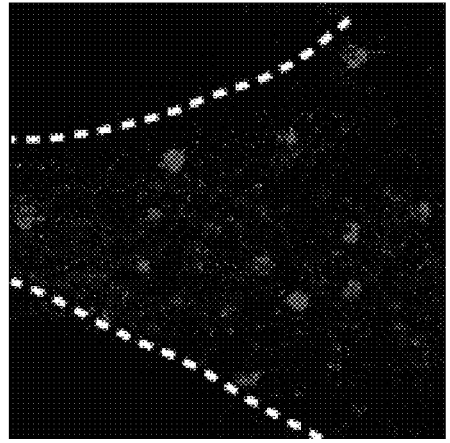
Figure 10C:
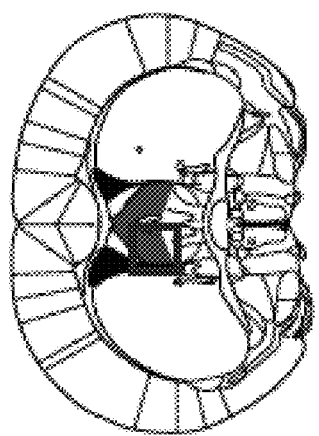
Figure 10C:
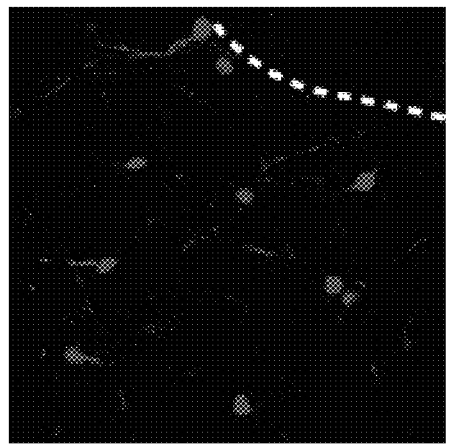
Figure 10D:
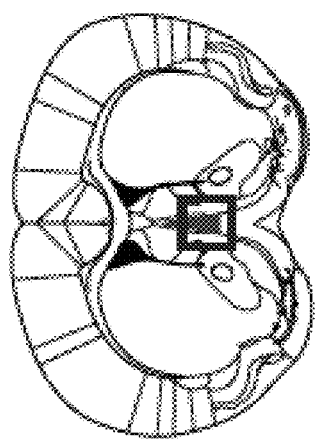
Figure 10D:
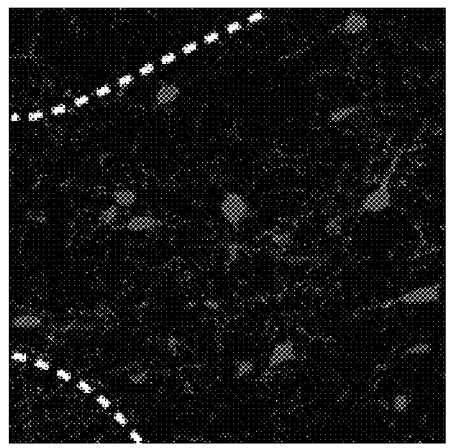
Figure 10K:
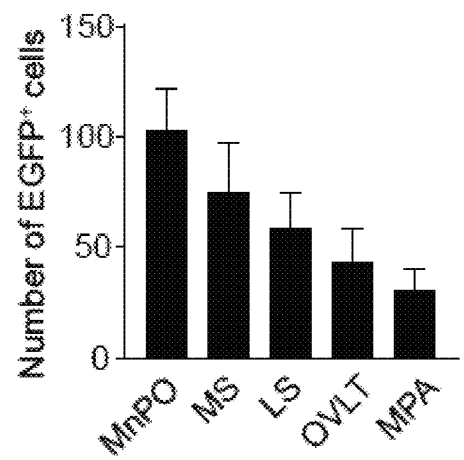
Figure 11A:
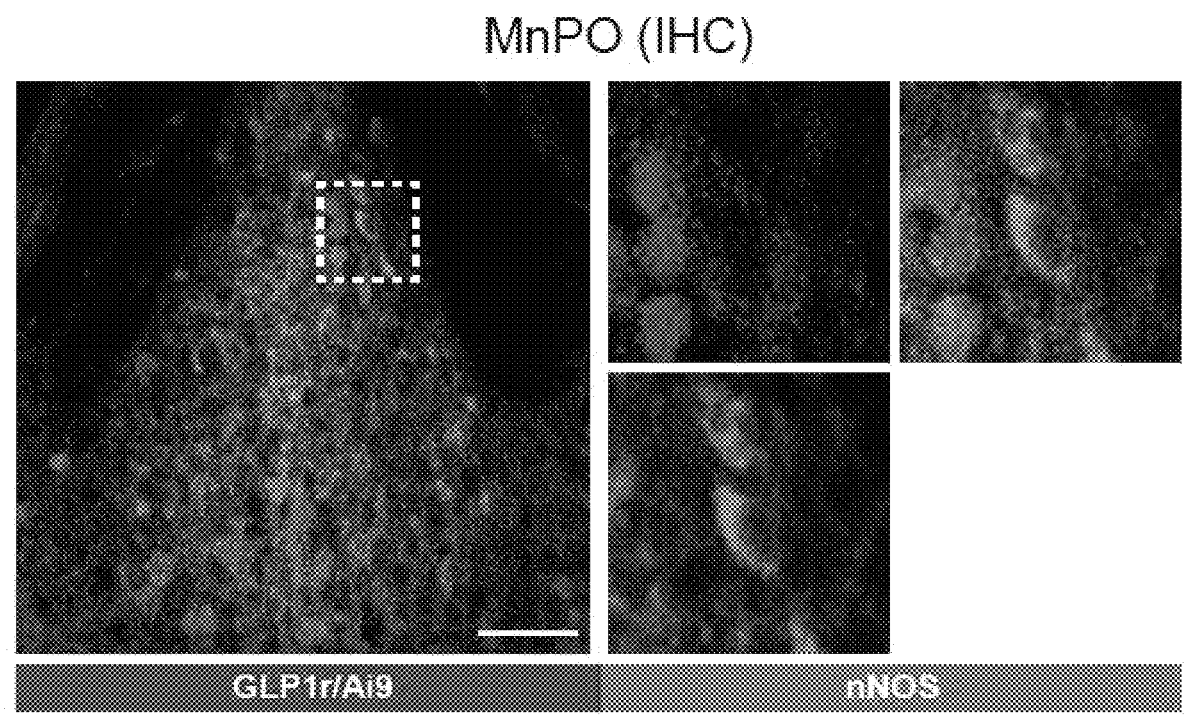
Figure 11B:
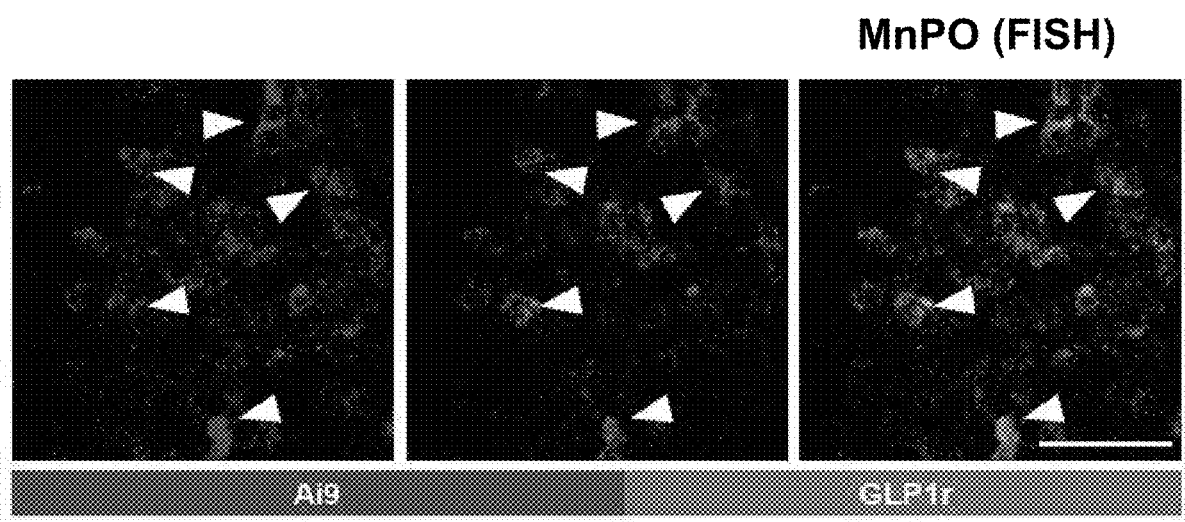
Figure 11C:
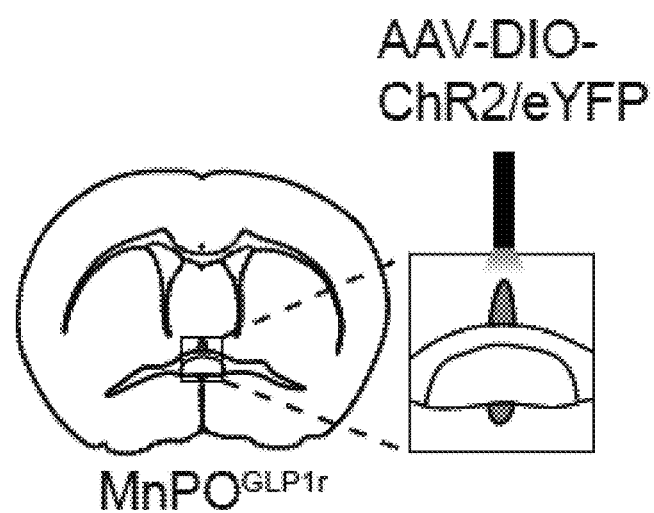
Figure 11F:
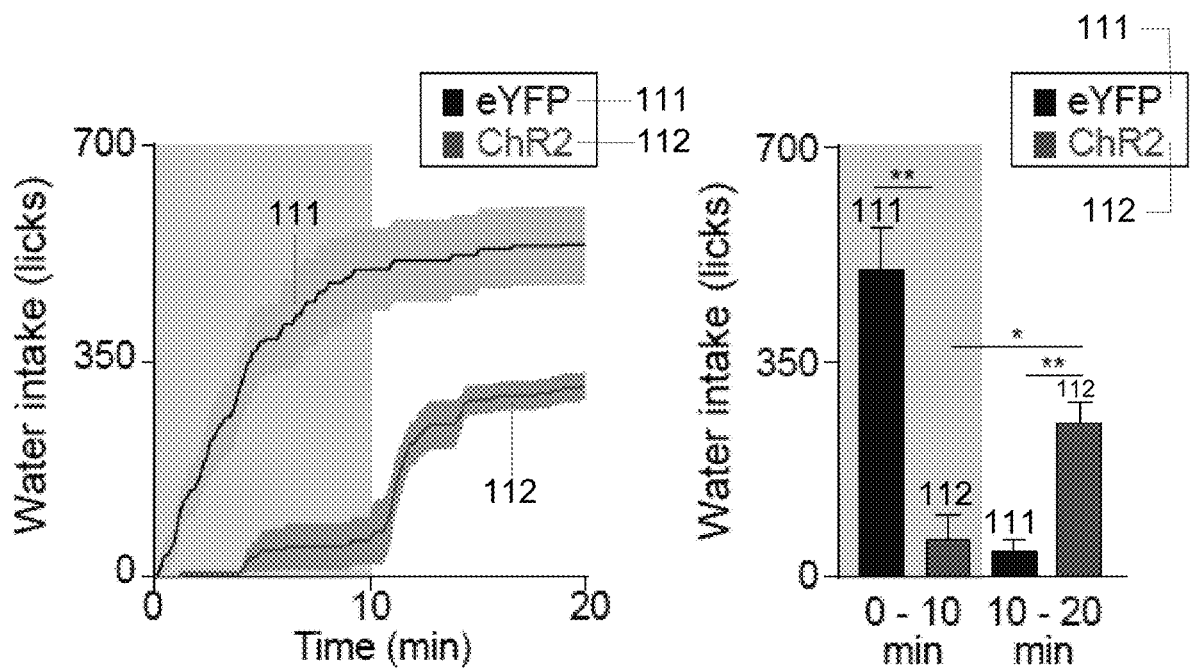
Figure 11F:
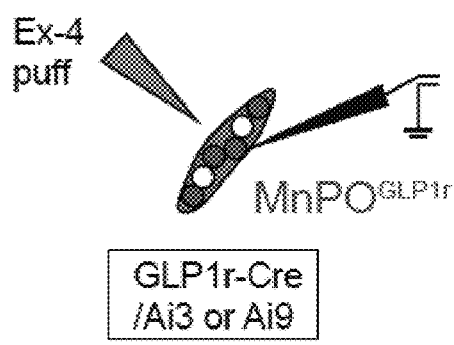
Figure 11G:
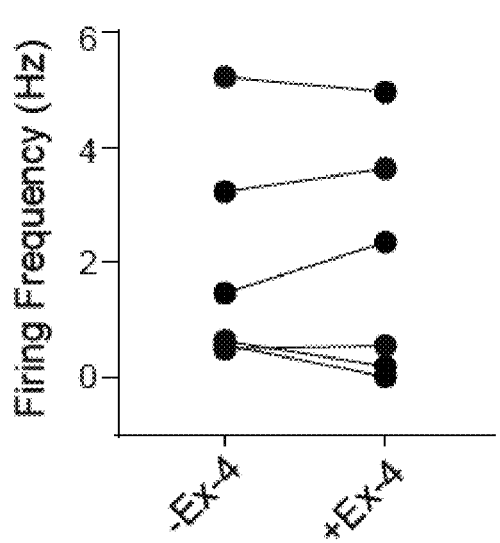
Figure 11H:
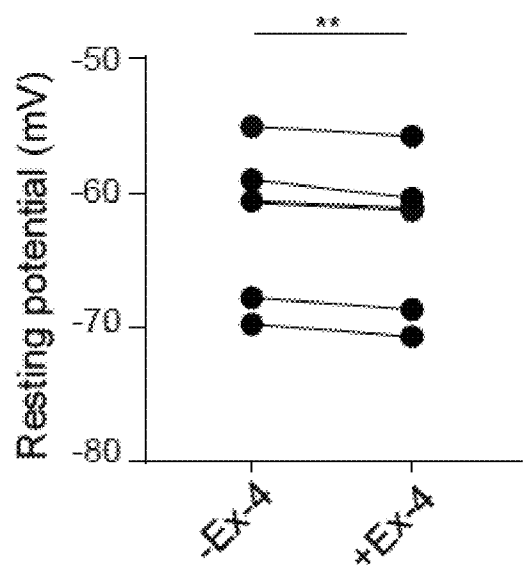
Figure 11I:
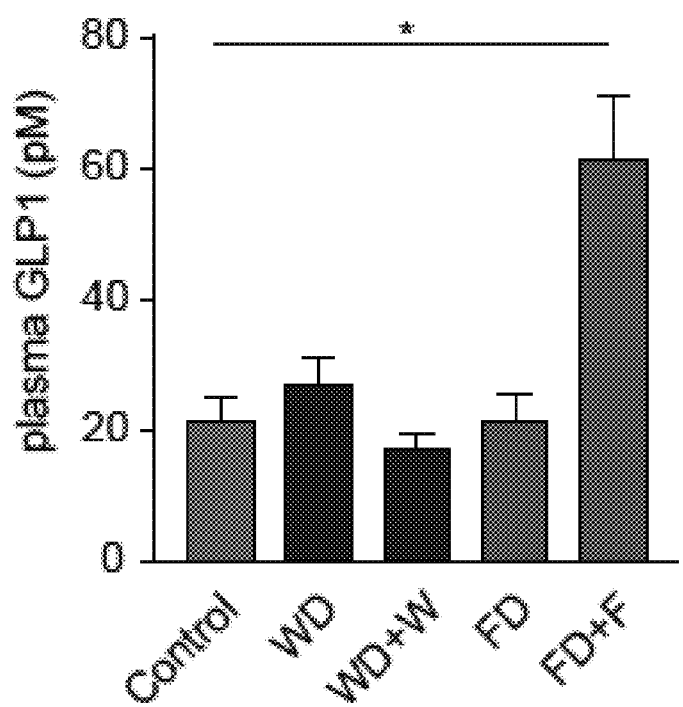
Figure 11J:
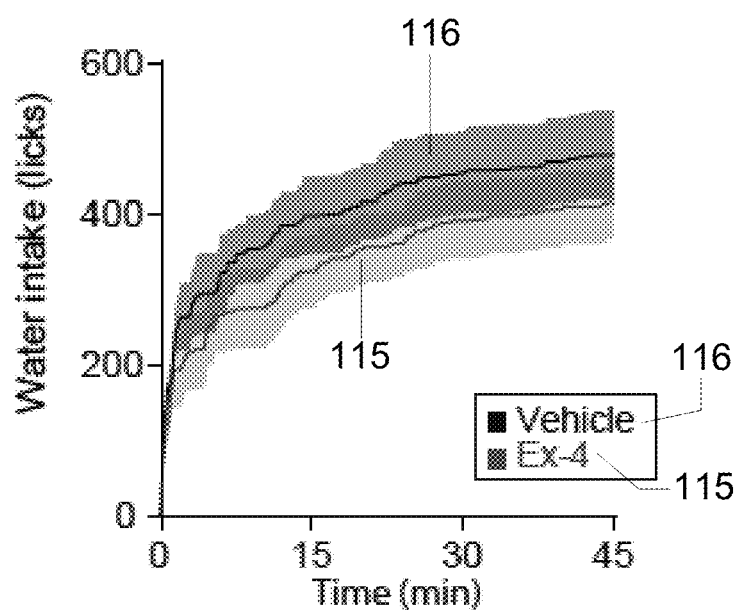
Figure 11K:
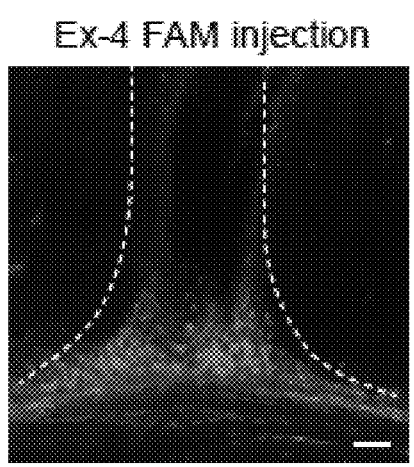

Thirst neurons of the LT mediate water drinking, but they also receive negative feedback regulation by drinking itself[1],[8],[13]. It has been shown that water intake rapidly suppresses the activity of SFO$^{nNOS}$ neurons[8]. We reproduced these results, and extended this observation to the downstream MnPO$^{nNOS}$ neurons (FIGS. 9A-F). This quick regulation of thirst circuits helps animals to optimize fluid ingestion[7],[13]. To dissect the neural basis of drinking-induced thirst inhibition, we functionally mapped the upstream inhibitory circuits of SFO$^{nNOS}$ neurons by two neural tracing approaches. First, we retrogradely labelled inhibitory neurons that project to the SFO by injecting herpes simplex virus encoding Cre-dependent mCherry (HSV-mCherry) into the SFO of Vgat-Cre animals (FIG. 2A). Among HSV-positive structures throughout the brain (FIGS. 10A-H), the MnPO contained the strongest HSV signals whereas the same injection into control animals showed no signals (FIG. 2B). Second, we performed monosynaptic RV tracing from SFO$^{nNOS}$ neurons (FIGS. 10I-K). Consistent with our HSV tracing, the MnPO contained most RV-positive neurons that minimally overlapped with nNos-expressing excitatory neurons (FIGS. 10I-K). Without being limited by theory, these complementary tracing results suggest that GABAergic neurons in the MnPO are a major source of inhibitory input to the SFO[20].

Figure 2C:
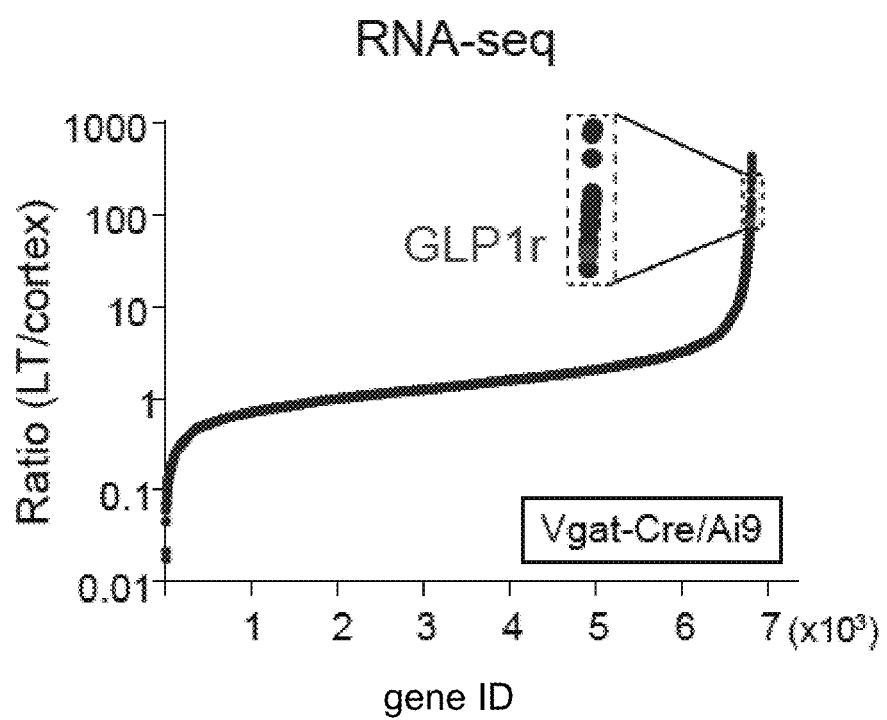
Figure 2H:
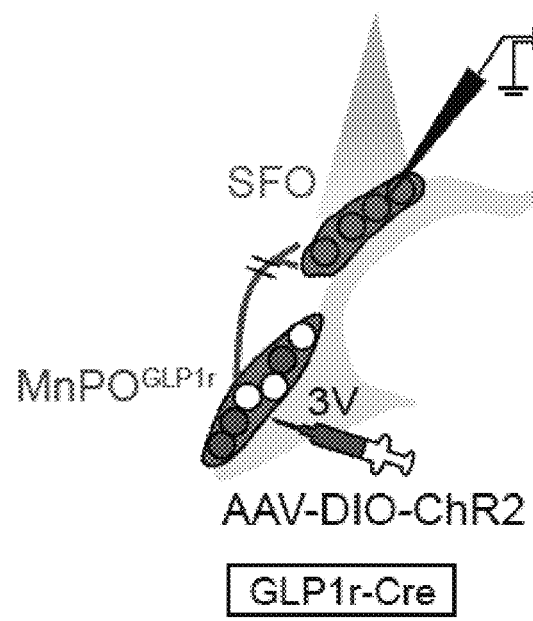
Figure 2I:
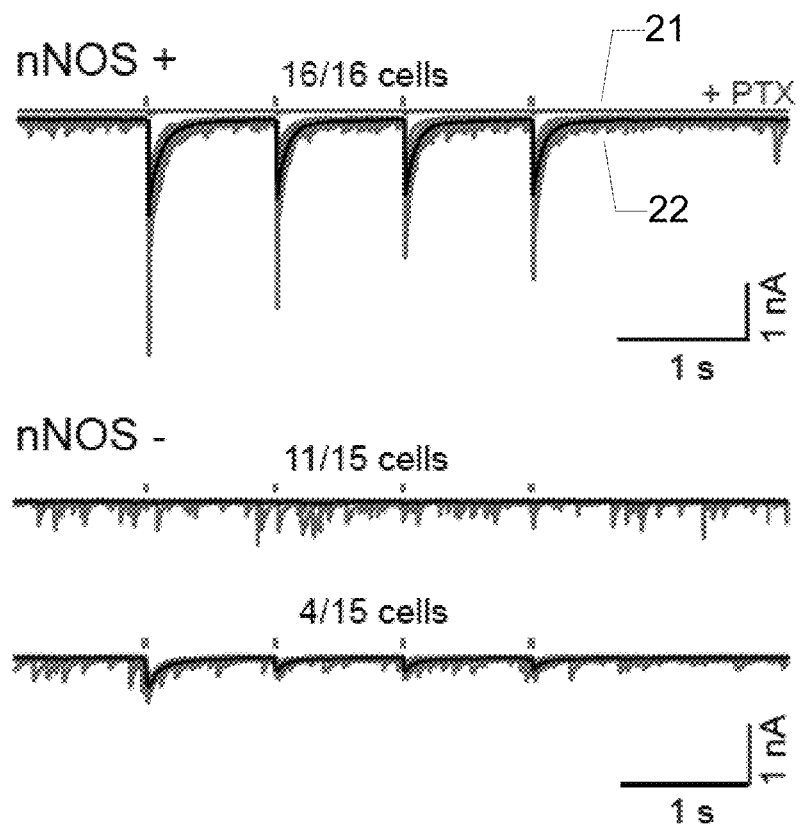
Figure 2J:
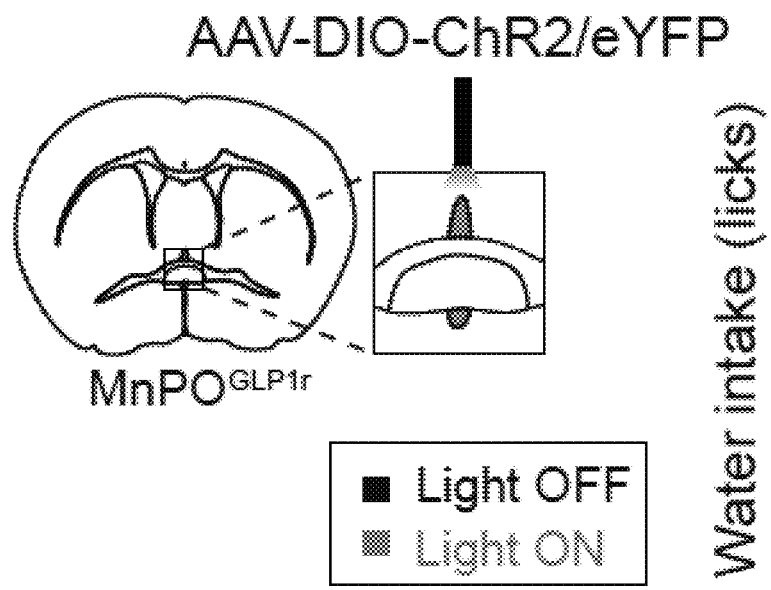
Figures 2K, 2L, 2M:
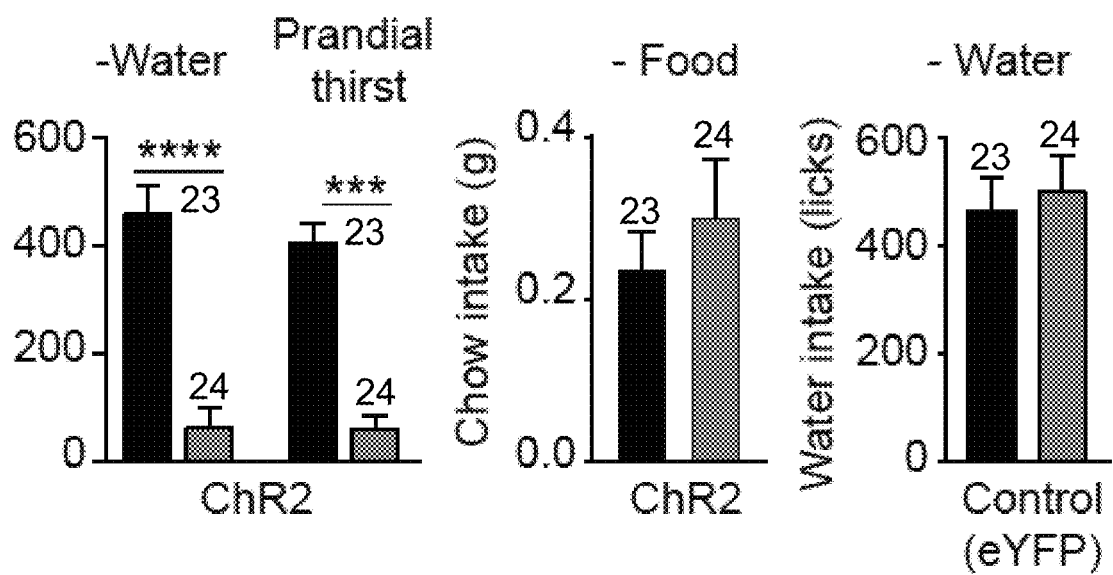

To gain a more specific genetic handle on these neurons, we performed RNA-seq analysis from the inhibitory population of the dorsal LT (containing the MnPO and SFO) and the cortex using Vgat-Cre/Ai9 mice. By comparing gene expression patterns, we found that GLP1r transcripts were highly enriched in inhibitory neurons from the LT by 100- fold compared to the cortex (FIG. 2C). In situ hybridization and immunohistochemical studies using GLP1r-Cre mice[27] confirmed that GABAergic MnPO neurons mostly overlapped with GLP1r-expressing neurons (FIGS. 2D-G and FIGS. 11A-B). We validated direct synaptic connections between the GLP1r-expressing MnPO (MnPO$^{GLP1r}$) population and SFO$^{nNOS}$ neurons in slice preparation by ChR2-assisted circuit mapping[28] (FIG. 2H). All recorded SFO$^{nNOS}$ neurons (16/16 cells) received GABAergic synaptic current from MnPO$^{GLP1r}$ neurons with an IPSC latency of 8.4 ms. However, SFO$^{non-nNOS}$ neurons rarely did so (4/15 cells with smaller IPSCs), indicating that the SFO$^{nNOS}$ population primarily receives monosynaptic inhibitory inputs from MnPO$^{GLP1r}$ neurons (FIG. 2I). Moreover, optogenetic stimulation of MnPO$^{GLP1r}$ neurons selectively suppressed water intake in thirsty animals (FIGS. 2J-M and FIGS. 11C-E). This acute inhibition was not observed by the application of a GLP1r agonist (FIGS. 11F-K).

Collectively, these data show that the MnPO$^{GLP1r}$ population plays a key modulatory role for thirst as a major source of inhibitory input to the SFO.

Example 3

This example shows that MnPO$^{GLP1r}$ neurons are rapidly and transiently activated during drinking behavior.

Figure 3A:
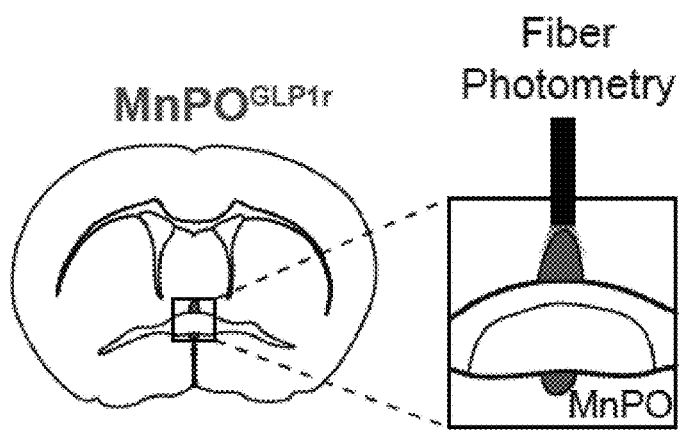
Figure 3B:
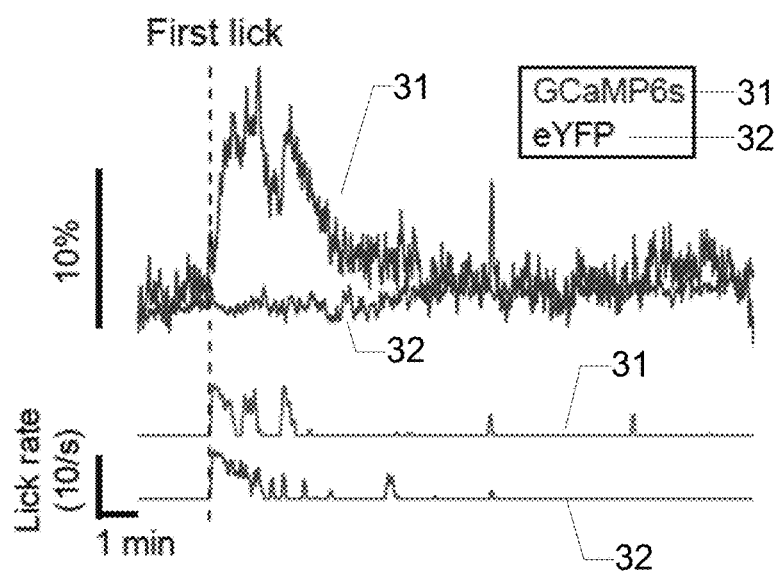
Figure 3C:
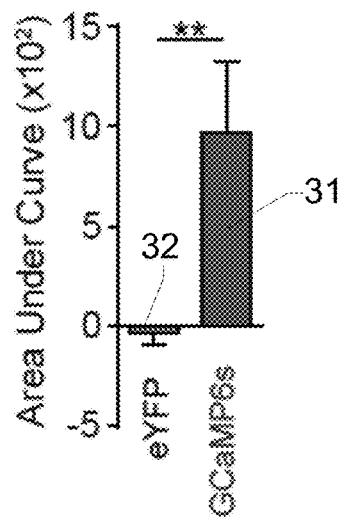
Figure 3G:
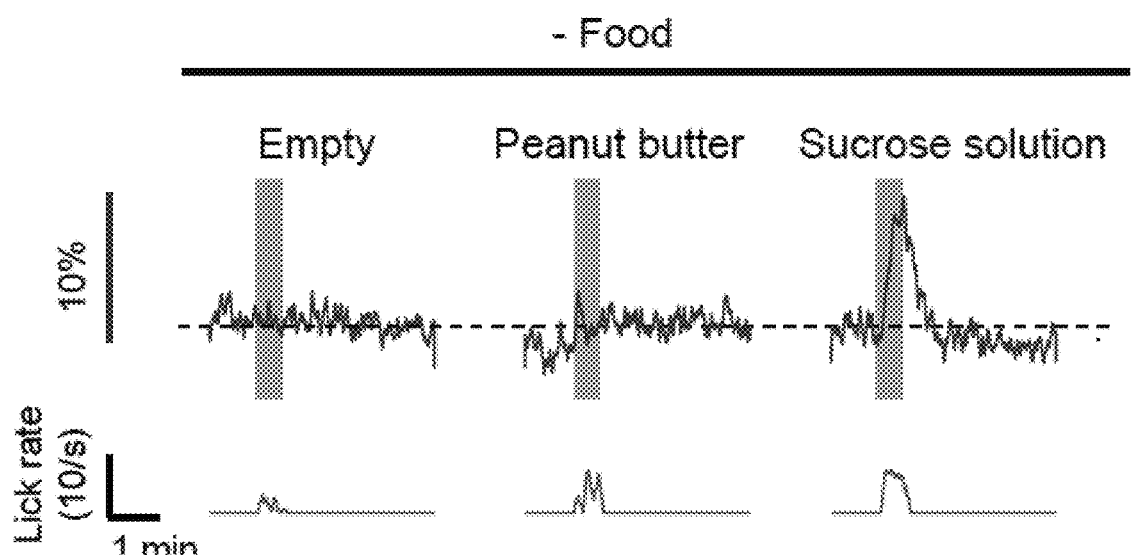
Figure 3H:
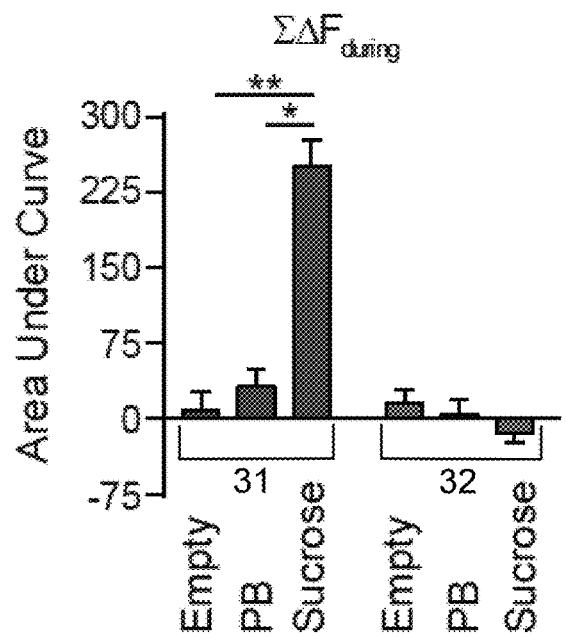
Figure 3I:
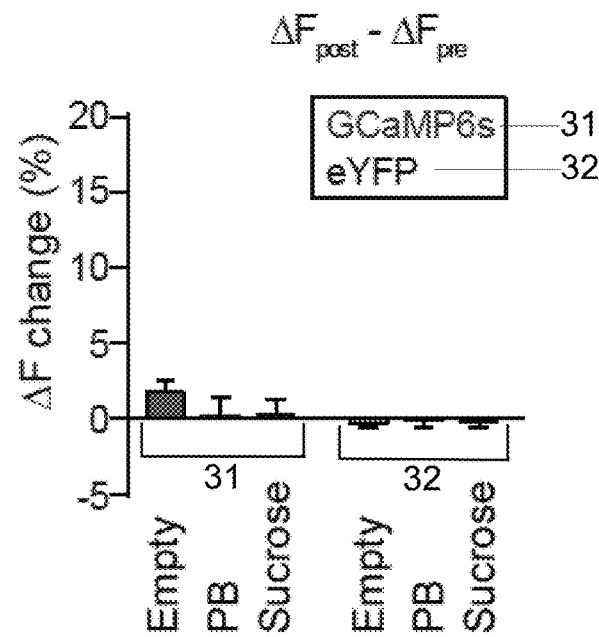

To examine the function of MnPO$^{GLP1r}$ neurons in drinking behavior, we measured in vivo calcium dynamics by infecting AAV-hSyn-flex-GCaMP6s in GLP1r-Cre mice (FIGS. 3A-C). We found that MnPO$^{GLP1r}$ neurons were acutely activated during water drinking, and their activity returned to the basal level when animals stopped drinking (FIG. 3B, upper trace). These neurons responded equally when animals licked water and isotonic saline, but not an empty spout (FIG. 3D, and FIGS. 12G-K). Interestingly and unexpectedly, the responses were also observed toward non-aqueous silicon oil, showing that the activation of MnPO$^{GLP1r}$ neurons is independent of fluid composition. We next tested the internal-state-dependency of these responses (FIG. 3G). Under food-restricted conditions, we found that MnPO$^{GLP1r}$ neurons still responded upon licking sucrose solution (300 mM, FIG. 3G and FIGS. 12G-K). However, solid peanut butter evoked no response despite its high palatability (FIG. 3G). Even without the instinctive need, SFO-induced drinking in water-satiated animals induced responses in MnPO$^{GLP1r}$ neurons (FIGS. 12L-O). These optical recording studies show that MnPO$^{GLP1r}$ neurons are purely activated by fluid consumption but not reward-seeking behaviour or licking action per se. Consistent with their connections to the SFO, the activity of the SFO$^{nNOS}$ population precisely mirrored the calcium dynamics of MnPO$^{GLP1r}$ neurons except that water intake evoked an additional persistent inhibition (FIGS. 12A-F). Without being limited by theory, this MnPO$^{GLP1r}$-independent water-specific inhibition of SFO$^{nNOS}$ neurons is likely due to osmolality sensing or water absorption in the gastrointestinal tract as proposed previouslyn[7]. These results demonstrate two significant and unexpected properties of thirst circuits: 1) MnPO$^{GLP1r}$ neurons are activated upon fluid ingestion independent of fluid composition or the animal's internal state, and 2) this population transmits inhibitory signals to SFO$^{nNOS}$ neurons that is time-locked to drinking.

In sum, the data show that MnPO$^{GLP1r}$ neurons were rapidly activated by fluid consumption and that responses were transient, i.e., responses did not persist after termination of drinking.

Example 4

This example shows that MnPO$^{GLP1r}$ neurons distinguish between eating and drinking behavior based on ingestive speed.

Figure 4G:
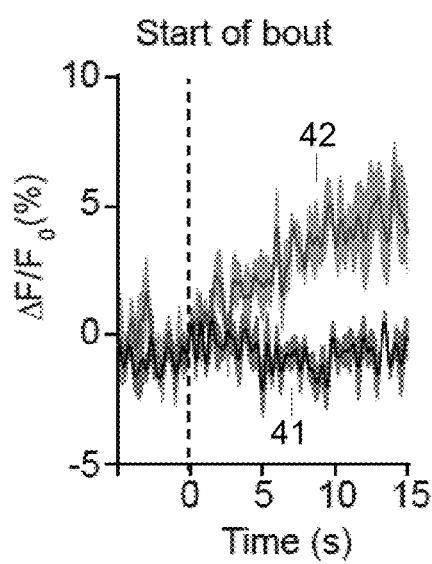
Figure 4H:
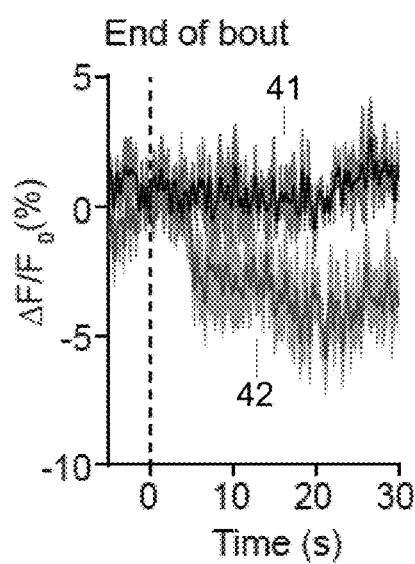
Figure 4J:
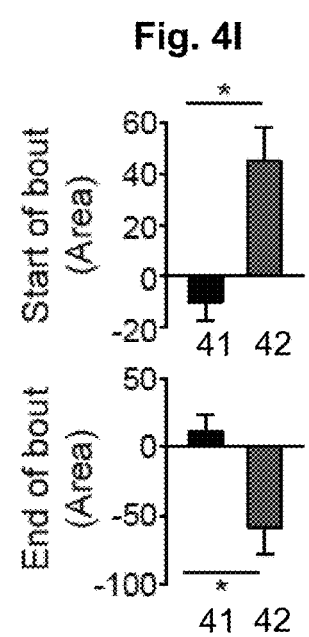

We further investigated the mechanisms by which MnPO$^{GLP1r}$ neurons exclusively represent fluid intake. To this end, we provided thirsty animals with water in two different forms, liquid and gel (HydroGel: 98% water+ hydrocolloids), while recording MnPO$^{GLP1r}$ activity (FIGS. 4A-B). In either form, thirsty animals ingested a similar amount of water within the 30-min session (FIGS. 4C-F). Intriguingly and unexpectedly, compared to the robust activation of MnPO$^{GLP1r}$ neurons by water-drinking, gel-eating behaviour failed to elicit any responses (FIGS. 4A-B). Their activity changes were well-correlated with the onset and offset of liquid water intake, but not with gel intake (FIGS. 4G-J). Similarly, eating normal chow did not stimulate this neural population (FIGS. 4K-L). Therefore, MnPO$^{GLP1r}$ neurons are able to distinguish between drinking and eating behaviors even if an animal consumes practically the same substance. Without being limited by theory, these results raise the concept that the MnPO$^{GLP1r}$ population facilitates satiety induced by drinking, but not specifically by water-intake.

Figures 4Q, 4R, 4S:
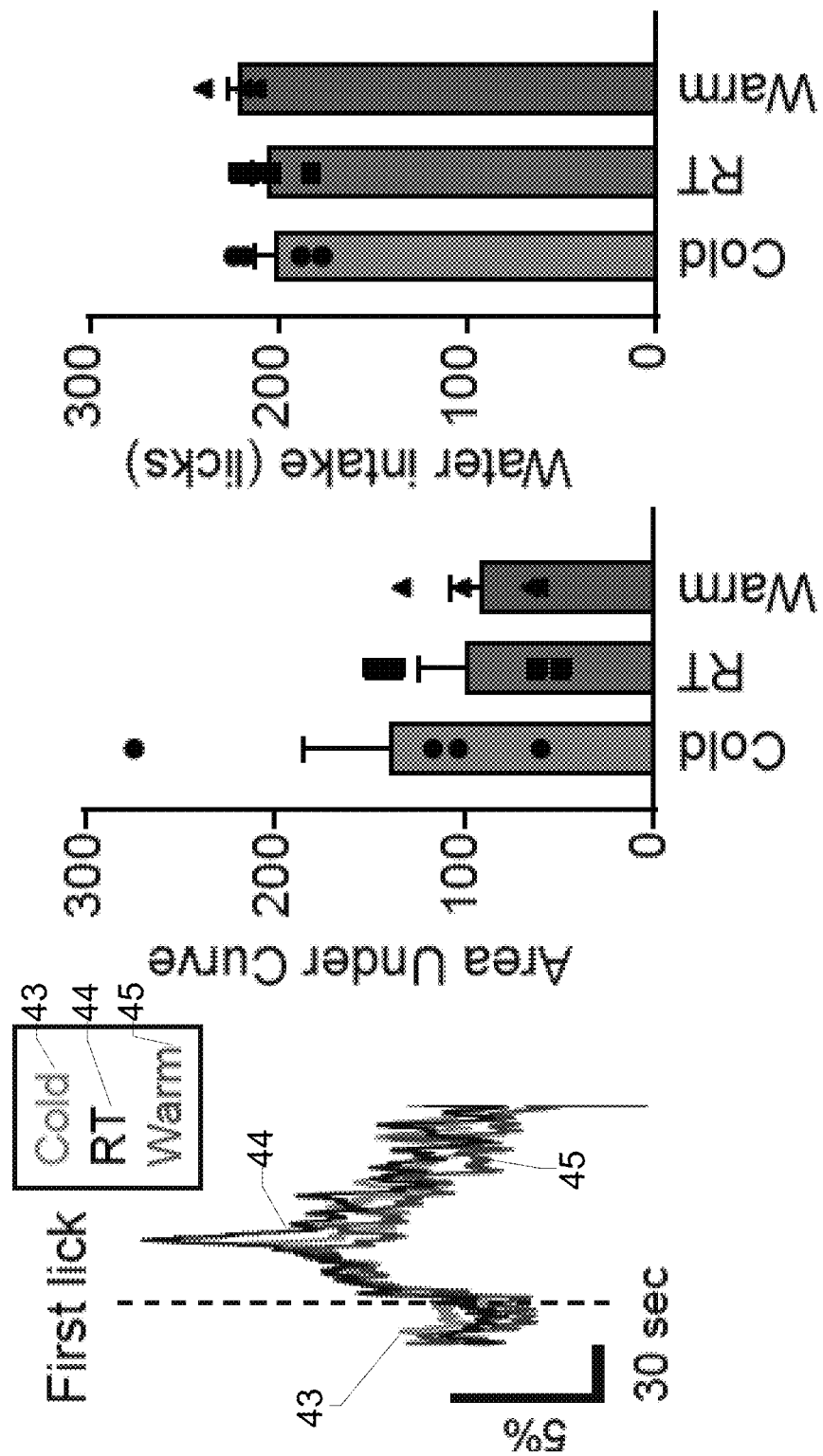

Because the ingestive rate (speed) was considerably different between drinking water and eating HydroGel (FIGS. 4C-F), we suspected that MnPO$^{GLP1r}$ neurons may monitor ingestive pattern to distinguish the mode of consumption. To examine this possibility, animals were given access to water for 30 s total at different rates; 2 s×15 times and 30 s×1 time (FIGS. 4M-P). As hypothesized, concentrated/continuous drinking evoked significantly bigger responses in MnPO$^{GLP1r}$ neurons than sparse drinking, regardless of the total amount of consumed water (FIGS. 4M-P). In addition, the temperature of fluid did not affect the responses (FIGS. 4Q-S). Without being limited by theory, because animals can ingest fluids much faster than solid substances, these data strongly support the idea that the MnPO$^{GLP1r}$ population distinguishes between drinking and eating based on ingestive speed. Consequently, concentrated (fast) fluid intake recruits MnPO$^{GLP1r}$-mediated inhibition signals, which in turn suppress the activity of SFO$^{nNOS}$ neurons. Without being limited by theory, these findings provide key mechanistic insights into rapid thirst alleviation as a result of drinking behavior.

In sum, the data show that MnPO$^{GLP1r}$ neurons population distinguish between drinking and eating based on ingestive speed, thus rapidly alleviating thirst.

Example 5

This example shows that inhibition of MnPO$^{GLP1r}$ neurons leads to over-drinking.

Given a function of the MnPO$^{GLP1r}$ population to monitor fluid intake, we next examined its physiological significance for drinking regulation. We addressed this question by acute chemogenetic loss-of-function manipulation (FIGS. 5A-C). While any fluid elicits transient MnPO$^{GLP1r}$→SFO$^{nNOS}$ inhibition, water evokes an additional inhibitory effect that persists after drinking episodes (compare FIGS. 12A-C water vs saline). Due to this water-specific signal, inhibition of MnPO$^{GLP1r}$ neurons by CNO had a minor effect on the total water intake (30 min) in water-restricted animals (FIGS. 13A-D). In contrast, drastic effects were observed for isotonic saline where MnPO$^{GLP1r}$-independent inhibitory signals are absent (FIGS. 5D-E). Compared to the vehicle control, inhibition of MnPO$^{GLP1r}$ neurons strikingly increased both the total amount and duration of saline intake (FIGS. 5F-G and FIGS. 13A-H). However, under satiated conditions, the same manipulation did not elevate water or saline intake, likely excluding the possibility that inhibiting MnPO$^{GLP1r}$ neurons directly stimulates appetite (FIGS. 5F-G). We observed the same over-drinking phenotype in mice where MnPO$^{GLP1r}$ neurons were ablated by Casp3 (FIGS. 13I-L). Without being limited by theory, our functional manipulation studies demonstrated that MnPO$^{GLP1r}$ neurons promote satiety of thirst by monitoring real-time fluid intake, malfunction of which leads to polydipsic overdrinking, especially for non-hypoosmotic fluids such as saline.

Together, this study identified genetically-defined thirst circuits in the LT that integrate the instinctive need and its consequent drinking behavior to maintain internal water balance (FIG. 5H). We showed that multiple downstream populations of SFO$^{nNOS}$ neurons are individually sufficient to induce water intake. Without being limited by theory, these data are reminiscent of the circuit organization for hunger where eating behavior is redundantly encoded by multiple output projections of AgRP neurons in the arcuate nucleus[29]. However, we further demonstrated that thirst neurons of the LT are hierarchically organized, and that the MnPO$^{nNOS}$ population is the behavioral output neurons. Previous lesion studies in rats and sheep have proposed a model that the MnPO serves as a central site that integrates inputs from osmosensory neurons of the SFO and OVLT[30]-[32]. Without being limited by theory, our findings well explain and further advance the concept of this model with cell-type-specific precision. While the necessity of the SFO may vary among species[8], the MnPO appears to consistently function as the key center for drinking across species[32]. Without being limited by theory, it is notable, however, that ablating excitatory neurons in a given nucleus may leave an imbalance of excitatory-inhibitory output to downstream brain areas, which could explain an inhibitory effect on drinking. In our analysis, MnPO$^{nNOS}$ neurons project to various areas including the hypothalamus and hindbrain (FIGS. 14A-I). Without being limited by theory, these results reveal a neural logic of thirst processing in the LT circuit, and provide a platform to dissect how appetite for water is integrated at downstream sites of MnPO$^{nNOS}$ neurons.

Notably and unexpectedly, MnPO$^{GLP1r}$ neurons selectively responded to drinking but not eating behavior. These inhibitory neurons provide rapid monosynaptic inhibition to thirst-driving SFO$^{nNOS}$ neurons. Without being limited by theory, our results strongly indicate that the MnPO$^{GLP1r}$ population facilitates thirst satiation by drinking rather than water absorption. Without being limited by theory, at a psychophysical level, these findings provide an explanation for the long-standing observation that thirst is quickly alleviated with the onset of drinking[5], [7]. At a physiological level, these results revealed a neural interface that adjusts the activity of thirst neurons based on real-time drinking behavior. Although systemic recovery of fluid balance relies on water absorption into the blood, thirst is modulated by multiple preabsorptive factors including oral, oropharyngeal, and gastrointestinal signals[1]. Without being limited by theory, it is unlikely that the MnPOGLP1r→SFO$^{nNOS}$ circuit mediates water-specific oral sensory information such as taste[33] because it responds to any fluid, including silicon oil. Instead, MnPO$^{GLP1r}$ neurons may function as a flow-meter by sensing gulping action in the oropharyngeal area, and provide liquid[7] specific rapid inhibition to thirst circuits. This notion is consistent with previous findings that drinking hyperosmotic saline[6], but not eating food[34], transiently suppressed vasopressin secretion. Without being limited by theory, in this model, MnPO$^{GLP1r}$ neurons serve as a central detector that discriminates fluid from solid ingestion, which promotes acute satiation of thirst through the SFO and other downstream targets (FIGS. 14 J-U). Subsequently, gastrointestinal mechanisms may selectively detect water over other fluids that induce persistent inhibitory effects on SFO$^{nNOS}$ neurons (FIGS. 12A-C). [0110] In sum, the data show that malfunction or inhibition of MnPO$^{GLP1r}$ neurons leads to polydipsic overdrinking due to the MnPO$^{GLP1r}$ population facilitating thirst satiation by drinking rather than water absorption.

REFERENCES

Each of the following references is incorporated by reference in its entirety herein.

1 Booth, D. J. R. a. D. Thirst: Physiological and Psychological Aspects. Chapters 5, 6, 9-12, and 19 (Springer-Verlog, 1991).
2 Bourque, C. W. Central mechanisms of osmosensation and systemic osmoregulation. Nature reviews. Neuroscience 9, 519-531, doi:10.1038/nrn2400 (2008).
3 McKinley, M. J. & Johnson, A. K. The physiological regulation of thirst and fluid intake. News Physiol Sci 19, 1-6 (2004).
4 Sternson, S. M. & Eiselt, A. K. Three Pillars for the Neural Control of Appetite. Annu Rev Physiol 79, 401-423, doi:10.1146/annurev-physiol-021115-104948 (2017).
5 Saker, P. et al. Regional brain responses associated with drinking water during thirst and after its satiation. Proceedings of the National Academy of Sciences 111, 5379-5384 (2014). 20
6 Seckl, J. R., Williams, T. D. & Lightman, S. L. Oral hypertonic saline causes transient fall of vasopressin in humans. Am J Physiol 251, R214-217 (1986).
7 Thrasher, T. N., Nistal-Herrera, J. F., Keil, L. C. & Ramsay, D. J. Satiety and inhibition of vasopressin secretion after drinking in dehydrated dogs. Am J Physiol 240, E394-401 (1981).
8 Zimmerman, C. A. et al. Thirst neurons anticipate the homeostatic consequences of eating and drinking. Nature 537, 680-684 (2016).
9 Zimmerman, C. A., Leib, D. E. & Knight, Z. A. Neural circuits underlying thirst and fluid homeostasis. Nature reviews. Neuroscience 18, 459-469, doi:10.1038/nrn.2017.71 (2017).
10 Oka, Y., Ye, M. & Zuker, C. S. Thirst driving and suppressing signals encoded by distinct neural populations in the brain. Nature, doi:10.1038/nature14108 (2015).
11 Simpson, J. B. & Routtenberg, A. Subfornical organ: site of drinking elicitation by angiotensin II. Science 181, 1172-1175 (1973).
12 Fitzsimons, J. Angiotensin, thirst, and sodium appetite. Physiological reviews 78, 583-686 (1998).
13 Stricker, E. M. & Hoffmann, M. L. Presystemic signals in the control of thirst, salt appetite, and vasopressin secretion. Physiology & behavior 91, 404-412, doi:10.1016/j.physbeh.2007.04.007 (2007).
14 Farrell, M. J. et al. Cortical activation and lamina terminalis functional connectivity during thirst and drinking in humans. Am J Physiol-Reg/301, R623-R631, doi:10.1152/ajpregu.00817.2010 (2011). 21

15 Denton, D. A., McKinley, M. J. & Weisinger, R. S. Hypothalamic integration of body fluid regulation. *Proc Natl Acad Sci USA* 93, 7397-7404 (1996).

16 Johnson, A. K. & Gross, P. M. Sensory circumventricular organs and brain homeostatic pathways. *FASEB journal: official publication of the Federation of American Societies for Experimental Biology* 7, 678-686 (1993).

17 McKinley, M. J. et al. The sensory circumventricular organs of the mammalian brain. *Advances in anatomy, embryology, and cell biology* 172, 1-122 (2003).

18 Betley, J. N. et al. Neurons for hunger and thirst transmit a negative-valence teaching signal. *Nature* 521, 180-185, doi:10.1038/nature14416 (2015).

19 Nation, H. L., Nicoleau, M., Kinsman, B. J., Browning, K. N. & Stocker, S. D. DREADD-induced activation of subfornical organ neurons stimulates thirst and salt appetite. *Journal of neurophysiology* 115, 3123-3129 (2016).

20 Abbott, S. B., Machado, N. L., Geerling, J. C. & Saper, C. B. Reciprocal Control of Drinking Behavior by Median Preoptic Neurons in Mice. *J Neurosci* 36, 8228-8237, doi:10.1523/JNEUROSCI.1244-16.2016 (2016).

21 Matsuda, T. et al. Distinct neural mechanisms for the control of thirst and salt appetite in the subfornical organ. *Nature neuroscience* 20, 230-241, doi:10.1038/nn.4463 (2017).

22 Miselis, R. R., Shapiro, R. E. & Hand, P. J. Subfornical organ efferents to neural systems for control of body water. *Science* 205, 1022-1025 (1979).

23 Wickersham, I. R. et al. Monosynaptic restriction of transsynaptic tracing from single, genetically targeted neurons. *Neuron* 53, 639-647, doi:10.1016/j.neuron.2007.01.033 (2007). 22

24 Yang, C. F. et al. Sexually dimorphic neurons in the ventromedial hypothalamus govern mating in both sexes and aggression in males. *Cell* 153, 896-909, doi:10.1016/j.cell.2013.04.017 (2013).

25 Roth, B. L. DREADDs for Neuroscientists. Neuron 89, 683-694, doi:10.1016/j.neuron.2016.01.040 (2016).

26 Lerner, T. N. et al. Intact-brain analyses reveal distinct information carried by SNc dopamine subcircuits. *Cell* 162, 635-647 (2015).

27 Richards, P. et al. Identification and characterization of GLP-1 receptor-expressing cells using a new transgenic mouse model. *Diabetes* 63, 1224-1233, doi:10.2337/db13-1440 (2014).

28 Petreanu, L., Huber, D., Sobczyk, A. & Svoboda, K. Channelrhodopsin-2-assisted circuit mapping of long-range callosal projections. *Nature neuroscience* 10, 663-668, doi:10.1038/nn1891 (2007).

29 Betley, J. N., Cao, Z. F., Ritola, K. D. & Sternson, S. M. Parallel, redundant circuit organization for homeostatic control of feeding behavior. *Cell* 155, 1337-1350, doi:10.1016/j.cell.2013.11.002 (2013).

30 Cunningham, J. T., Beltz, T., Johnson, R. F. & Johnson, A. K. The effects of ibotenate lesions of the median preoptic nucleus on experimentally-induced and circadian drinking behavior in rats. *Brain research* 580, 325-330 (1992).

31 McKinley, M., Mathai, M., Pennington, G., Rundgren, M. & Vivas, L. Effect of individual or combined ablation of the nuclear groups of the lamina terminalis on water drinking in sheep. *American Journal of Physiology-Regulatory, Integrative and Comparative Physiology* 276, R673-R683 (1999). 23

32 McKinley, M. J. et al. The median preoptic nucleus: front and centre for the regulation of body fluid, sodium, temperature, sleep and cardiovascular homeostasis. *Acta physiologica* 214, 8-32, doi:10.1111/apha.12487 (2015).

33 Zocchi, D., Wennemuth, G. & Oka, Y. The cellular mechanism for water detection in the mammalian taste system. *Nature neuroscience* (2017).

34 Thrasher, T. N., Keil, L. C. & Ramsay, D. J. Drinking, oropharyngeal signals, and inhibition of vasopressin secretion in dogs. *American Journal of Physiology-Regulatory, Integrative and Comparative Physiology* 253, R509-R515 (1987).

35 Oka, Y., Butnaru, M., von Buchholtz, L., Ryba, N. J. & Zuker, C. S. High salt recruits aversive taste pathways. Nature 494, 472-475 (2013).

36 Krashes, M. J. et al. An excitatory paraventricular nucleus to AgRP neuron circuit that drives hunger. Nature 507, 238-242, doi:10.1038/nature12956 (2014).

37 Kahles, F. et al. GLP-1 secretion is increased by inflammatory stimuli in an IL-6-dependent manner, leading to hyperinsulinemia and blood glucose lowering. Diabetes 63, 3221-3229, doi:10.2337/db14-0100 (2014).

38 Allen, W. E. et al. Thirst-associated preoptic neurons encode an aversive motivational drive. Science 357, 1149-1155, doi:10.1126/science.aan6747 (2017).

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method of using a composition (e.g., a method comprising administering a first nucleic acid and/or a second nucleic acid) is disclosed herein, the corresponding composition for use is also expressly contemplated. For example, for the disclosure of a method of inhibiting, ameliorating, reducing the severity of, treating, reducing the likelihood of, or preventing dehydration, adipsia, hypodipsia, and/or kidney disease disorder or damage in a subject in need thereof comprising administering a nucleic acid encoding a conditional ion modulator (or a vector comprising the first and second nucleic acids), the corresponding nucleic acid (or vector) for use in inhibiting, ameliorating, reducing the severity of, treating, reducing the likelihood of, or preventing dehydration, adipsia, hypodipsia, and/or kidney disease disorder or damage are also contemplated.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of stimulating fluid intake in a subject in need thereof, the method comprising:
   identifying the subject as in need of stimulating fluid intake; and
   stimulating depolarization of a polarized cell membrane in a first nitric oxide synthase (nNOS)-positive neuron of the median preoptic nucleus (MnPO),
      thereby stimulating the first nNOS-positive neuron, thereby stimulating fluid intake in the subject.

2. The method of claim 1, wherein stimulating depolarization of the cell membrane comprises at least one of a net influx of cations into a cytosol of the first nNOS-positive neuron, a net efflux of anions from the cytosol of the first nNOS-positive neuron, and/or stimulating a second nNOS-positive neuron of the subfornical organ (SFO).

3. The method of claim 1, wherein the subject suffers from dehydration, adipsia, hypodipsia, or a kidney disorder or kidney damage or kidney disease.

4. The method of claim 1, comprising stimulating depolarization of a polarized cell membrane specifically in nNOS-positive neurons among a population of neurons of the MnPO.

5. The method of claim 1, wherein stimulating depolarization of the cell membrane of the first nNOS-positive neuron comprises:
   administering a nucleic acid encoding a stimulatory conditional ion modulator to the subject, the stimulatory conditional ion modulator configured to induce a net influx of cations into the cytosol of the first nNOS-positive neuron and/or a net efflux of anions from the cytosol of the first nNOS-positive neuron in response to a stimulus or agonist,
   whereby the nucleic acid is under the control of a promoter that induces transcription of the nucleic acid in the first nNOS-positive neuron, whereby the conditional ion modulator is expressed in the first nNOS-positive neuron; and
   applying an agonist or stimulus to the first nNOS-positive neuron of the subject, causing the conditional ion modulator to induce the net influx of cations into and/or the net efflux of anions from the cytosol of the first nNOS-positive neuron.

6. The method of claim 5, wherein the stimulatory conditional ion modulator comprises a hM3DREADD and the agonist comprises clozapine-N-oxide, or
   wherein the stimulatory conditional ion modulator comprises a channelrhodopsin and the agonist comprises electromagnetic radiation.

7. The method of claim 5, wherein the nucleic acid is administered to the subject in an adeno-associated viral (AAV) vector.

8. The method of claim 1, wherein stimulating depolarization of the cell membrane comprises inhibiting a glucagon-like peptide-1 receptor (GLP1r)-positive neuron of the MnPO.

9. The method of claim 8, wherein inhibiting the GLP1r-positive neuron comprises:
   administering a nucleic acid encoding an inhibitory conditional ion modulator to the subject, the inhibitory conditional ion modulator configured to inhibit depolarization of a cell membrane of the GLP1r-positive neuron by inducing a net efflux of cations from a cytosol of the GLP1r-positive neuron and/or inducing a net influx of anions into the cytosol of the GLP1r-positive neuron in response to a stimulus or agonist, whereby the nucleic acid is under the control of a promoter that induces transcription of the nucleic acid in the GLP1r-positive neuron, whereby the inhibitory conditional ion modulator is expressed in the GLP1r-positive neuron; and applying an agonist or stimulus to the GLP1r-positive neuron of the subject, causing the inhibitory conditional ion modulator to induce the net efflux of cations from the cytosol and/or the next influx of anions into the cytosol of the GLP1r-positive neuron.

10. The method of claim 9, wherein the inhibitory conditional ion modulator comprises a hM4Di and the agonist or stimulus comprises clozapine-N-oxide (CNO).

* * * * *

UNITED STATES PATENT AND TRADEMARK OFFICE
CERTIFICATE OF CORRECTION

| | | |
|---|---|---|
| PATENT NO. | : 10,960,084 B2 | Page 1 of 2 |
| APPLICATION NO. | : 16/245801 | |
| DATED | : March 30, 2021 | |
| INVENTOR(S) | : Yuki Oka | |

It is certified that error appears in the above-identified patent and that said Letters Patent is hereby corrected as shown below:

On the Title Page

Column 1, Line 2, item [56], delete "motidational" and insert --motivational--.

In the Drawings

In sheet 26 of 72, FIG. 6A, Line 4 (Approx.), delete "restiction" and insert --restriction--.

In the Specification

Column 2, Line 41, delete "next influx" and insert --net influx--.

Column 4, Line 11, delete "left;)" and insert --left)--.

Column 4, Line 11, delete "SR)," and insert --SFO,--.

Column 7, Line 35, delete "rastor" and insert --raster--.

Column 10, Line 30, delete "respectively)." and insert --respectively.--.

Column 10, Line 49, delete "13 E-H," and insert --13E-H,--.

Column 11, Line 8, delete "14 J-U)" and insert --14J-U)--.

Column 16, Lines 58-59, delete "intreperitoneally," and insert --intraperitoneally,--.

Column 19, Line 44, delete "Gprasp 1," and insert --Gprasp1,--.

Column 20, Line 33, delete "Gpraspl," and insert --Gprasp1,--.

Signed and Sealed this
        Twenty-first Day of December, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)

Column 23, Line 46, delete "adispia," and insert --adipsia,--.

Column 23, Line 47, delete "dyfunction," and insert --dysfunction,--.

Column 23, Line 51, delete "adispia," and insert --adipsia,--.

Column 25, Line 21, delete "(Nat)," and insert --(Na$^+$),--.

Column 27, Line 61, delete "aarchaeorhodopsin." and insert --archaeorhodopsin.--.

Column 30, Line 6, delete "MnPO)." and insert --MnPO.--.

Column 31, Line 37, delete "1.".

Column 34, Line 21, delete "Ai10" and insert --Ai110--.

Column 34, Line 35, delete "AAVS-" and insert --AAV5- --.

Column 34, Line 38, delete "GCaMP6 s" and insert --GCaMP6s--.

Column 34, Line 39, delete "GC aMP6s" and insert --GCaMP6s--.

Column 36, Line 66, delete "20x." and insert --20X.--.

Column 36, Line 67, delete "FIG." and insert --FIGS.--.

Column 37, Line 51, delete "(-25° C.)" and insert --(~25° C.)--.

Column 37, Line 54, delete "KCl2.5," and insert --KCl 2.5,--.

Column 37, Line 62, delete "KCl4," and insert --KCl 4,--.

Column 38, Line 33, delete "ELISA" and insert the same on Column 38, Line 34 as a new Para heading.

Column 39, Line 12, delete "monoynaptic" and insert --monosynaptic--.

Column 41, Line 58, delete "previouslyn[7]." and insert --previously[1],[7].--.

Column 44, Line 6, delete "14 J-U)." and insert --14J-U).--.

Column 44, Line 31, delete "physio1" and insert --physiol--.

In the Claims

Column 51, Claim 9, Line 14, delete "next influx" and insert --net influx--.